(12) United States Patent
LaBelle et al.

(10) Patent No.: US 9,865,827 B1
(45) Date of Patent: Jan. 9, 2018

(54) ADAPTIVELY OPTIMIZED BIOLOGICAL COMPONENTS FOR BIOHYBRID DEVICES

(71) Applicants: Jeffrey T. LaBelle, Tempe, AZ (US); Vincent B. Pizziconi, Phoenix, AZ (US)

(72) Inventors: Jeffrey T. LaBelle, Tempe, AZ (US); Vincent B. Pizziconi, Phoenix, AZ (US)

( * ) Notice: Subject to any disclaimer, the term of this patent is extended or adjusted under 35 U.S.C. 154(b) by 0 days.

(21) Appl. No.: 14/715,504

(22) Filed: May 18, 2015

Related U.S. Application Data

(60) Continuation-in-part of application No. 13/466,120, filed on May 8, 2012, now Pat. No. 9,034,623, which is a continuation-in-part of application No. 12/215,502, filed on Jun. 26, 2008, now Pat. No. 8,173,407, which is a continuation-in-part of application No. 11/475,342, filed on Jun. 26, 2006, now abandoned, which is a division of application No. 10/658,541, filed on Sep. 8, 2003, now Pat. No. 7,067,293.

(60) Provisional application No. 60/408,775, filed on Sep. 7, 2002.

(51) Int. Cl.
*H01L 51/00* (2006.01)
*C12Q 1/24* (2006.01)
*H01L 31/055* (2014.01)
*C25B 1/00* (2006.01)
*H01L 51/44* (2006.01)

(52) U.S. Cl.
CPC ............ *H01L 51/0093* (2013.01); *C12Q 1/24* (2013.01); *C25B 1/003* (2013.01); *H01L 31/055* (2013.01); *H01L 51/44* (2013.01)

(58) Field of Classification Search
CPC .................................................. H01L 51/0093
See application file for complete search history.

(56) References Cited

U.S. PATENT DOCUMENTS 6,342,389 B1 * 1/2002 Cubicciotti .......... C07K 14/195
435/317.1

* cited by examiner

*Primary Examiner* — Rosanne Kosson

(57) ABSTRACT

Embodiments of apparatus, compositions, methods, systems, and articles of manufacture are disclosed relating to the optimization and production of biological components for use in biohybrid photosensitive devices and systems and other applications. In some embodiments, biologically derived components are disclosed having properties and/or characteristics that are optimized for applications of interest relative to corresponding components derived from naturally occurring organisms. In some embodiments, properties and/or characteristics of biological components are optimized by subjecting organisms and/or populations thereof to forced adaptation.

10 Claims, 19 Drawing Sheets

10 nm 10 nm $$\text{Photonic Figure of Merit} = \frac{\%T_{440} \text{ (Bchl c Soret)}}{\%T_{440} \text{ (Bchl c Soret)} + \%T_{460} \text{ (carotenoid)}} \times \frac{\%T_{795} \text{ (Bchl a Baseplate)}}{\%T_{740} \text{ (Bchl c oligomeric } Q_y\text{)}}$$

| | %T 795 Bchl a | %T 740 Bchl c | %T 460 carotenoid | %T 440 Soret |
|---|---|---|---|---|
| Well 1 | 0.9625 | 0.6067 | 0.6417 | 0.7034 |
| Well 21 | 0.9555 | 0.8044 | 0.5703 | 0.5985 |
| Well 22 | 0.9502 | 0.7948 | 0.565 | 0.5908 |
| Well 23 | 0.9553 | 0.8997 | 0.8599 | 0.8671 |
| Well 24 | 0.9569 | 0.9237 | 0.8731 | 0.8736 |
| Well 26 | 0.9566 | 0.8732 | 0.7793 | 0.7895 |
| Well 28 | 0.9541 | 0.6126 | 0.6421 | 0.7161 |

ADAPTIVELY OPTIMIZED BIOLOGICAL COMPONENTS FOR BIOHYBRID DEVICES

CROSS REFERENCE TO RELATED APPLICATIONS

This application is a continuation-in-part of U.S. application Ser. No. 13/466,120, filed May 8, 2012, issuance on May 19, 2015 as U.S. Pat. No. 9,034,623, which is a continuation-in-part of U.S. application Ser. No. 12/215, 502, filed Jun. 26, 2008, issued on May 8, 2012 as U.S. Pat. No. 8,173,407, which is a continuation-in-part of U.S. application Ser. No. 11/475,342, filed Jun. 26, 2006, abandoned, which is a divisional of U.S. application Ser. No. 10/658,541, filed Sep. 8, 2003 and issued Jun. 27, 2006 as U.S. Pat. No. 7,067,293, which claims priority from provisional U.S. patent application Ser. No. 60/408,775, filed Sep. 7, 2002. This application is related to U.S. application Ser. Nos. 11/475,356, 11/475,338, 11/475,343, abandoned, all filed Jun. 26, 2006, all U.S. divisional applications of U.S. application Ser. No. 10/658,541. Priority is claimed from each of the applications enumerated in this paragraph, all of which are in the name of the present inventors, and the full disclosures of each are incorporated herein by reference.

STATEMENT REGARDING FEDERALLY SPONSORED RESEARCH

Financial assistance for this project was provided by the U.S. Government through the National Science Foundation under Grant Numbers 9602258 and 9986614 and the United States Government may own certain rights to the invention(s) disclosed herein.

TECHNICAL FIELD

Disclosed herein are apparatus, compositions, methods, and articles of manufacture relating to the design and production of biological components and/or their incorporation in devices and systems, including biohybrid photosensitive devices and systems.

BACKGROUND

Hybrid devices wherein biologically derived components interact with non-biological components offer the opportunity, as yet largely unexploited, to bring the forces of evolution and natural selection to bear on problems of engineering. Recently, attempts to marry biology and engineering to create various biohybrid constructs have been steadily increasing. A limited number of novel biohybrid sensor applications have already been reported, and in some cases commercialized, that incorporate "smart" molecular-scale biological components. These have attracted considerable interest from both the biomedical and biotechnology communities worldwide. However, little has been done to date in developing integrated nanodevices and systems such as microanalytical systems incorporating novel, engineered nanobioconstructs and their analogues for use in integrated nanodevices and systems such as bio-optical hybrid sensors capable of very sensitive and selective nanoscale detection due to enhanced performance characteristics as determined by a prescribed biohybrid Figure of Merit (FoM). Potential applications include microsystem applications requiring low-level light detection capability (e.g. micro total analytical systems (μTAS) for immunoassay, genomics and proteomics), such as "point-of-care" diagnostic medicine, biotechnology, space bioengineering, energy harvesting and conversion, and countermeasures to biowarfare for defense, among others.

In general, the current state of the art for engineering design as taught by Koen (Koen, 1987) and many others (Otto and Wood, 2001), has not led to the achievement of device components, stand-alone devices, nor engineered systems that function or otherwise perform at a prescribed FoM and oftentimes typically perform at levels significantly below optimal FoM levels and theoretically achievable maximum FoM limits.

The well-known area of thermoelectric device design exemplifies the present ability of engineering design heuristics to achieve a desirable thermoelectric FoM (i.e., ZT) that significantly exceeds current ZT device values of ~1 although a ZT value of 4 is theoretically possible (Rowe, D. M., 1995). The present inability of those skilled in the art to achieve desired material and device FoMs characterizes virtually all engineering device design applications spanning diverse disciplinary fields and broad industry product segments.

In recent years, less effective and predictive empirical approaches have been used to devise novel hybrid devices that incorporate naturally derived biological materials and constructs, or mimetics thereof, that have resulted in enhanced device performance relative to their non-hybrid engineered counterpart. To date, however, the engineering method does not teach how to design, select, modify or otherwise alter smart, nanoscale energy-interactive materials, such as molecular-scale biophotonic components, derived from natural or biomimetic analog constructs, despite their intrinsically superior and potentially adaptable structural and performance characteristics. Nor does the engineering method show those skilled in this art how such nanoscale materials can be further embodied or employed as components, or as stand-alone devices, that are capable of producing robust and scalable energy-interactive biohybrid devices and systems that function at a desired FoM not yet achievable by conventional engineering means.

Photoactive semiconductors such as Si photovoltaic cells (as one example of a large scale device) have long been known. They have been employed in various devices and applications for years. Their varying responsivity to certain light wavelengths throughout the visible spectrum has been observed as well. On the biological side, thermophilic photosynthetic bacteria such as *Chloroflexus aurantiacus* (*C. aurantiacus*) and other species have been studied and reported upon. The photosensitive "light antenna" embodied in the chlorosomes of *C. aurantiacus* and in various other components of other organisms, have been studied and reported upon, as well. Perhaps as a result of inconsistency of results with photosynthetic bacteria, these organisms and their chlorosomes or other photosensitive components have not been incorporated into practicable devices. A need exists for improvement of the performance of photoactive devices throughout the light spectrum, and for techniques for harnessing the photosensitivity of photosynthetic bacteria in photoactive devices. More fundamentally, there is a need to identify inconsistencies in the photosensitivity (or other photonic or electroactivity) of biological specimens and to apply a method or methods to ameliorate or eliminate such inconsistencies and/or to optimize the performance of biological components for particular applications.

As one means of gathering knowledge about a system, Design of Experiment (DOE) analysis is a widely used statistical modeling approach, reported in detail elsewhere (Montgomery, 1991). A unique advantage of DOE, particularly as applied to complex adaptive systems, is its ability to elucidate not only the effect of the controlling variables, but also their complex interactions. Use of DOE analysis with biological or hybrid biological/non-biological devices and systems has not been encountered. In particular use of the powerful DOE approach in connection with forced adaptation in biological systems (such as bacteria) to move the systems toward a more consistent (i.e. dependable) performance and/or otherwise optimize the performance of biological components in biohybrid devices is not known. Figure of Merit (FoM) is another concept often used in engineering (among other fields such as economics, chemistry, astronomy, etc.). FoM is a measure of a device's performance. It is used in many contexts. However FoM as a design-driving measure, particularly with respect to adaptive biological organisms-based systems, devices and components is considered to be a radical departure from other uses of this concept. Further, as applied to biological organisms, parts thereof or systems made up of such organisms, control of multiple environmental variables is needed if the DOE approach is to be applied. The transfer function of a device, circuit or system is another engineering concept that is well understood. However, that concept has not ordinarily been applied to biological systems, if at all. A need exists to apply engineering concepts like DOE, FoM and the transfer function to the analysis, evaluation and design of biological, bioengineered and hybrid systems, components and devices.

SUMMARY

Disclosed here are embodiments of biohybrid devices, biological and non-biological components thereof, and methods relating thereto, including embodiments wherein biological components may be optimized by deliberate application of adaptive forces to guide the evolution of a population of organisms in a direction conducive to the expression of components having desired characteristics.

Biological entities may be employed as components in "bio-hybrid" devices and materials, in which they are combined with non-biological components. Biological light antenna structures may be usefully incorporated as components in biohybrid devices and materials whose function involves manipulation of light. Biological components may optionally be modified for an application of interest or to eliminate selected behavior, such as, for example, by removing reaction centers from biological light antenna structures to provide desired light transduction to photosensitive substrate purposes. The performance of biological components in such devices and materials may optionally be improved by force-adapting the components and/or the biological systems from which they are obtained, as disclosed herein, so as to produce desired behavior or performance that may differ from that of non-adapted components or systems. Force-adaptation may include manipulation of an environmental factor during growth, and selection based on desired criteria, as disclosed herein. The efficacy of the force-adaptation may optionally be enhanced by "intelligent" determination of environmental factor settings, guided by an objective function relating environmental factors and settings to a metric of performance characteristics of interest, such as an appropriate figure of merit.

An object of the present disclosure is to provide apparatus, compositions, methods, and articles of manufacture useful for the design, engineering, and optimization of biological components for particular applications, particularly in biohybrid devices.

An object of the present disclosure is to provide apparatus, compositions, methods, and articles of manufacture useful for designing, engineering, and/or producing biological components having particular characteristics, which may include performance characteristics, such as, for example, light absorption and/or emission characteristics, and/or any other characteristics that may be relevant to a particular application.

An object of the present disclosure is to provide photosensitive devices, including bio-hybrid devices, having improved light detection, absorption, transduction, or other characteristics, and to provide apparatus, compositions, methods, and articles of manufacture useful for producing such devices.

An object of the present disclosure is to provide apparatus, compositions, methods, and articles of manufacture useful for applying Design of Experiment principles to the design, optimization, and production of biological components.

An object of the present disclosure is to provide apparatus, compositions, methods, and articles of manufacture useful for designing, optimizing, and producing biological components conforming to an appropriate Figure of Merit and/or a desired transfer function.

An object of the present disclosure is to provide apparatus, compositions, methods, and articles of manufacture useful for determining an objective function useful in designing, optimizing, and producing biological components having particular desired characteristics.

An object of the present disclosure is to provide apparatus, compositions, methods, and articles of manufacture useful for force-adapting organisms and/or biological components so as to determine, optimize, and/or alter a characteristic thereof.

An object of the present disclosure is to provide force-adapted organisms and biological components having predetermined, optimized, and/or altered characteristics, and methods for producing them.

An object of the present disclosure is to provide bio-hybrid devices and materials that include biological components interacting with non-biological components to provide desired performance characteristics, and to provide methods for design and engineering of biological components for, and their incorporation in, bio hybrid devices and materials.

An object of the present disclosure is to provide apparatus, compositions, methods, and articles of manufacture useful for the synthesis, processing, design and manufacturing of high performance, scalable, adaptive and robust energy-interactive hybrid materials, devices and systems combining biological and non-biological technologies. Specifically, an exemplary embodiment adapts powerful engineering concepts to the engineering of biological components that are to be used in manufactured devices and systems, including hybrid devices and systems.

In a first aspect, there is provided a biohybrid apparatus including a plurality of light antenna structures disposed in or on a substrate.

In another aspect, an apparatus including light antenna structures optionally includes at least one RC− light antenna structure.

In another aspect, an apparatus including light antenna structures optionally includes at least one force-adapted light antenna structure, which may optionally be an RC− light antenna structure.

In another aspect, a biohybrid apparatus optionally includes a photoactive non-biological component disposed in the path of light emitted by at least one light antenna structure.

In another aspect, a biohybrid apparatus optionally includes light antenna structures disposed in or on a substrate and the substrate optionally includes or is integral with a photoactive non-biological component.

In another aspect, a biohybrid apparatus optionally includes light antenna structures that are disposed in an ordered array and/or that are directionally oriented.

In another aspect, a biohybrid apparatus optionally includes one or more light antenna structures that emit emitted light in response to light incident thereon, and the emitted light includes light that is Stokes-shifted with respect to the incident light.

In another aspect, a biohybrid apparatus optionally includes one or more light antenna structures extracted from force-adapted organisms and/or progeny of said organisms, or obtained from an expression system expressing a genetic sequence cloned or derived from force-adapted organisms.

In another aspect, a biohybrid apparatus optionally includes one or more force-adapted light antenna structures wherein the force-adaptation includes an enhancement of the emission by a light antenna structure of at least one wavelength of light in response to at least one wavelength of incident light, and/or wherein the force-adaptation includes an increase in the pigment content of the light antenna structures.

In another aspect, a biohybrid apparatus optionally includes a photoactive non-biological component, wherein energy is transmitted from at least one light antenna structure to the photoactive non-biological component by fluorescence resonant energy transfer (FRET).

In another aspect, a biohybrid apparatus optionally includes an RC– light antenna structures isolated or extracted from a force-adapted organism exhibiting a forced adaptation affecting at least one characteristic of the light antenna structures produced by said organism, which may be a characteristic comprising or affecting the response of the light antenna structures to light incident thereon.

In another aspect, a biohybrid apparatus optionally includes light antenna structures that are physically and/or chemically constrained in or on the substrate.

In another aspect, a biohybrid apparatus optionally includes light antenna structures that are synthetic equivalents or analogues of biologically derived light antenna structures.

In another aspect, a biohybrid apparatus optionally includes a photoactive non-biological component, which may be or include a photovoltaic component, a photodetector, a photodiode, a thermal detector, a metal-semiconductor-metal photodetector, and/or a complementary metal-oxide semiconductor (CMOS).

In another aspect, there is provided a method of making an apparatus, including subjecting a population comprising a plurality of organisms to forced adaptation whereby at least one organism expresses adapted light antenna structures altered in at least one characteristic; propagating said adapted light antenna structures in an organism or expression system; isolating or extracting adapted light antenna structures from said organism or expression system; and disposing in or on a substrate a plurality of adapted light antenna structures isolated or extracted from said organism or expression system.

In another aspect, there is provided a biologically derived material comprising at least one light antenna structure, made by a method of forced adaptation, the method including determining a relation relating at least one environmental variable to at least one characteristic of the biologically derived material, from said relation determining a value of the at least one environmental variable corresponding to a desired value of the at least one characteristic, growing a population of the organism subject to the at least one environmental variable at the value thereof so determined, and producing a biologically derived material from an organism manifesting the forced adaptation.

It will be apparent to persons of skill in the art that various of the foregoing aspects, and various other aspects disclosed herein, can be combined in a single device, method, composition, or article of manufacture, thus obtaining the benefit of more than one aspect. The disclosure hereof extends to all such combinations. The foregoing summary is intended to provide a brief introduction to the subject matter of this disclosure and does not limit or circumscribe the scope of the invention(s) disclosed herein, which are defined by the claims currently appended or as they may be amended, and as interpreted in the light of the entire disclosure.

DETAILED DESCRIPTION

Figure 1:
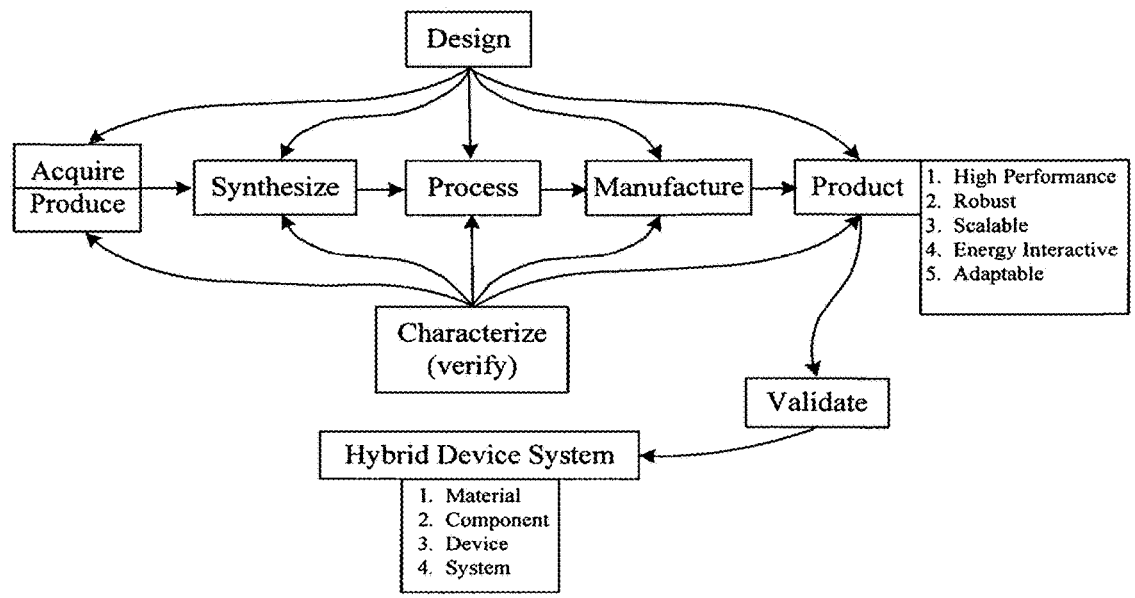
FIG. 1 is a conceptual block diagram illustrating elements in the design and development of a device, in particular a hybrid device of biological and non-biological content.
Figure 2:
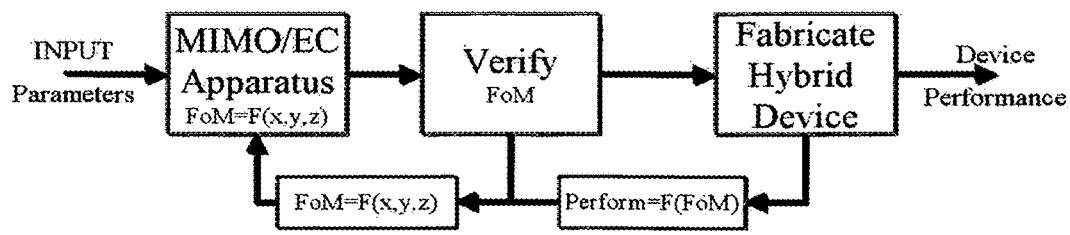
FIG. 2 is a conceptual flow chart of the design process for designing a hybrid device using a multiple input, multiple output environmental chamber and employing a figure of merit to gauge the performance of a biological component.

FIG. 1 exemplifies a novel method that will guide those skilled in the art to achieve the design and development of high performance hybrid materials and devices. As illustrated, several key steps are depicted in FIG. 1 that show one skilled in the art how to achieve desired and even optimal hybrid device designs that utilize smart, nanoscale constructs acquired, harvested or otherwise derived directly from complex living organisms. In an embodiment, a multiple input-multiple output apparatus, such as a multiple input-multiple output environmental chamber (i.e., MIMO/EC), and applicable computational algorithms, are employed to extract useful and exploitable hybrid device design heuristics. Use of this method will result in a desired and prescribed Figure of Merit in spite of the use of previously unknown or poorly defined or characterized nanoscale biological constructs and their function. In applied form, the novel engineering design method described herein will provide a means to identify or otherwise exploit intractable, or very difficult to identify, useful engineering specifications. An embodiment is shown in FIG. 2, an illustration of a novel method and apparatus for the design and development of high performance hybrid materials and devices. One application of the disclosures hereof is the enhancement of well-known photoactive semiconductor devices, such as Si photovoltaic cells using nanoscale biophotonic constructs that are either acquired, harvested or otherwise manipulated in their natural or adapted state using the methods and apparatus described herein to achieve desired FoM performance characteristics. Although commercially available Si photovoltaic cells have been employed in various devices and applications for years, their FoMs are typically low despite detailed knowledge of their structure and function and the ability to prescribe device performance specifications from use of selected light wavelengths throughout the visible spectrum, as well as, related device specifications associated with the engineering transfer function.

The transfer function of a component, device, or system is a useful engineering concept, directly related to the FoM, that is well known and understood by those skilled in the art. However, the use of a transfer function and related FoM concepts have not been generally applied and prescribed to biological constructs intended for use in the design of biohybrid devices and systems, if at all. Thus, an unmet and nonobvious need still exists to use well known engineering heuristics such as, the design of experiments (i.e., DOE), FoM and the transfer function for the analysis, design, and evaluation of bioengineered hybrid components, devices and systems.

To demonstrate the novelty and utility in the use of the hybrid device design heuristic to achieve high performance hybrid materials and devices (FIG. 2), an embodiment described herein improves the device performance of a stand-alone, commercial silicon photovoltaic device (SiPV) using a nanoscale bio-derived construct with generally unknown engineering specifications. However, the methods and apparati taught herein generally apply to the design and exploitation of any smart nanoscale or integrative nanoscale material, construct, or system, or mimics thereof, that is amenable to the FoM enhancement of a hybrid device or system.

A typical FoM of a SiPV device is generally less than 1 and typically only 0.28-0.32. Although a number of potentially useful hybrid design approaches can be employed to improve the SiPV FoM using the methods taught herein, the use of a nanoscale biophotonic construct having desired complementary energy transfer properties constitutes a potentially viable hybrid design approach. One such nanoscale biophotonic construct having potentially useful and exploitable engineering specifications to enhance the FoM of a photonic device, such as a SiPV device, is the nanoscale pigment-protein supramolecular construct known as a light antenna structure such as, for example, the structures that function as energy funnels in thermophilic photosynthetic bacteria such as *Chloroflexus aurantiacus* (*C. aurantiacus*) and other photosynthetic species. These highly quantum efficient photosensitive constructs (such as, for example, chlorosomes) are known to perform significant photonic energy shifts (red shift). In the case of the chlorosome associated with *C. aurantiacus*, input photonic energy at a wavelength of ~460-480 nm is typically shifted to ~800-820 nm with very little energy loss.

Typically SiPV devices are more sensitive to higher photonic wavelengths and generally most sensitive to the near infrared region (i.e. 800-900 nm) of the electromagnetic spectrum. Thus, in principle, the use of biologically-derived light antenna structures, as well as mimics or analogs thereof, could potentially enhance the FoM of a SiPV device if exploitable engineering specification(s), such as the transfer function or its associated FoM, could be identified, acquired, developed and subsequently employed successfully in a SiPV engineered hybrid device or system that meets a prescribed and verifiable FoM that validates the desired performance of the hybrid biophotonic device. However, the achievement of desired FoMs using hybrid device and system approaches is not obvious to those skilled in the art of device design and development, and empirical combinations of smart materials or components used in the design and manufacture of hybrid devices can oftentimes lead to device and system performances (i.e., FoM) inferior to non-hybrid device and system counterparts.

An embodiment described herein makes use of well-known design algorithms, such as the Design of Experiment (DOE), among many others known and appreciated by those skilled in the art. DOE analysis is a widely used statistical modeling design tool reported in detail elsewhere (Montgomery, 1991). A unique advantage of DOE, particularly as applied to complex adaptive systems, is its ability to elucidate not only the effect of the controlling or independent variables, but also their oftentimes complex interactions.

The use of DOE analysis in combination with a novel MIMO/EC apparatus can be used to identify, acquire or otherwise produce useful and exploitable engineering hybrid device and system specifications from complex biological constructs in their isolated or natural state or environment, or mimics thereof. In particular, the combined use of DOE with the MIMO/EC apparatus can provide a novel and powerful design heuristic to achieve desired engineering specifications of nanoscale-based constructs via their identification and/or modification from complex adaptive systems, such as viable organisms. The use of the DOE-MIMO/EC apparatus in this embodiment is most useful when it may be desirable to modify one or more properties of a complex adaptive construct through forced adaptation of a modifiable biological component of a viable complex system (such as bacteria). This produces the desired modification of a potentially useful property or characteristic of e.g. a nanoscale-based component that is useful to achieve a desired performance level (i.e. FoM) of a device or system in which that is not otherwise achievable by a non-hybrid.

In some embodiments, by varying the environmental conditions under which a biological component of, for example, a hybrid device, is grown, a transfer function for that component can be altered. Using the MIMO/EC of this disclosure, a biological component may be force-adapted in such a manner as to affect a modification of a transfer function that governs its outputs under given inputs. The desired transfer function can thus be engineered into a biological component, within bounds. In this context, a "transfer function" is a mathematical function relating the output or response of a system to its input(s). Devices, such as, for example, filters, that receive a signal and emit another signal in response thereto are often characterized in terms of a transfer function.

In an embodiment, the methods and equipment disclosed herein are used to engineer an exemplary hybrid photoactive component. That component combines a hitherto acceptable photoactive semiconductor device with a biological mechanism that has extremely high photoactive performance, to achieve performance unprecedented in devices of the type. This hybrid device uses a constituent of a photosynthetic bacterium to enhance the response of a semiconductor photoactive device across the intended spectrum of its use.

In an embodiment, with the methods and equipment disclosed herein, chlorosomes of the thermophilic green photosynthetic bacterium *Chloroflexus aurantiacus* (*C. aurantiacus*) are successfully coupled to a photoactive semiconductor device to derive enhanced performance across the relevant spectrum. In this embodiment, using design of experiment (DOE) methodology, adaptive biological units, such as cells, are force-adapted to achieve consistent performance in the characteristics of interest. In this, a multiple input-multiple output environment chamber (the above-mentioned MIMO/EC) affords the ability to force-adapt the bacteria from which these chlorosomes are gathered.

This embodiment is focused on exploiting biosystems at the nanoscale for their utility as functional 'device' components in a proposed biohybrid microdevice. More specifically, a design feasibility study was implemented to evaluate the efficacy of a naturally occurring nanoscale biophotonic, light adaptive antenna structure (the chlorosome) isolated from *C. aurantiacus*. The overall objective was to assess its utility as functional device component that would enhance the spectral performance characteristics of well-characterized photonic devices, such as, for example, solid-state photovoltaics.

The chlorosomes of *C. aurantiacus* are nanoscale, optical functional units having dimensions of approximately 100× 30×10 nm. They can transfer photonic energy at high quantum efficiencies (69-92%) and ultra-fast rates (picoseconds). They were fabricated into programmed arrays on solid substrates and fully characterized. These biological assemblies were subsequently integrated with the well-characterized photodetectors and evaluated for their potential to selectively enhance performance in the spectral regions where the photodetectors are inherently insensitive.

In broadest terms, a biohybrid device includes at least one biological component and at least one non-biological component disposed in a functional relation whereby the biological component delivers energy, material, or information to the non-biological component and thereby affects the functioning of the non-biological component, and/or the non-biological component delivers energy, material, or information to the biological component and thereby affects the functioning of the biological component. In an embodiment, a biohybrid device may include any number of biological components and non-biological components disposed in functional relation one to another, as may be appropriate or desirable for an application. In some embodiments a non-biological component may function to position or support one or more biological components and/or provide an interface to another device or to another non-biological component. Disclosed herein are apparatus, compositions, methods, and articles of manufacture for producing and optimizing biohybrid devices, and for producing and optimizing biological components for inclusion in biohybrid devices.

In an embodiment, a biological component may, as appropriate to a particular application of interest, be or include one or more entities, structures, or materials that may be of any biological origin, such as, for example, entities, structures, or materials extracted, isolated, obtained, or derived from living or dead organisms of any species; from populations of such organisms; from cells or cellular subunits or organelles or intracellular matter of such organisms; from matter excreted or emitted by such organisms; and/or from a cell culture, in vitro translation system, cell-free expression system, or other expression system. A biological component may be or include a discrete component and/or have distinct boundaries, or may be or include a bulk material having continuous properties. A biological component may be or include any synthetic or other equivalents or analogues of entities, structures, or materials of biological origin, such as, for example, components, entities, structures, or materials cloned, genetically engineered, synthesized, or produced in any other manner, derived from and having structure and composition equivalent to a component, entity, structure, or material of direct biological origin. A biological component may include one or more passive entities, structures, materials, or subcomponents of non-biological origin, such as, for example, to support or position biologically derived entities. A biological component may be of any structure, dimensions, geometry, spatial arrangement or other characteristics operable for an application of interest, and include one or more entities, structures, materials, or subcomponents of any biologically derived composition. A biological component may be made up of units of active biological material(s) (or equivalents or analogs of such material(s) if available). The units may be units harvested from a larger organism or organisms. Of particular interest are biological components having photoactive properties, such as, for example, light antenna structures.

In an embodiment, a non-biological component may be of any size, dimensions, geometry, composition, phase, or other properties, and having any function, operable for an application of interest. A non-biological component may include materials, subcomponents, or elements of biological origin, provided that the function of the non-biological component derives primarily from non-biological materials or elements. In some embodiments a photoactive biohybrid device includes one or more photoactive non-biological components that may be disposed in any relationship, geometric arrangement, or configuration wherein light energy emitted or transmitted by or through one or more biological components is received, absorbed, transmitted, transduced, or otherwise acted upon or influenced by the photoactive non-biological component(s). In some embodiments, one or more biological components transmits light energy to one or more photoactive non-biological components causing a change in state (such as an electrical characteristic change) of the photoactive non-biological component(s).

Figure 24:
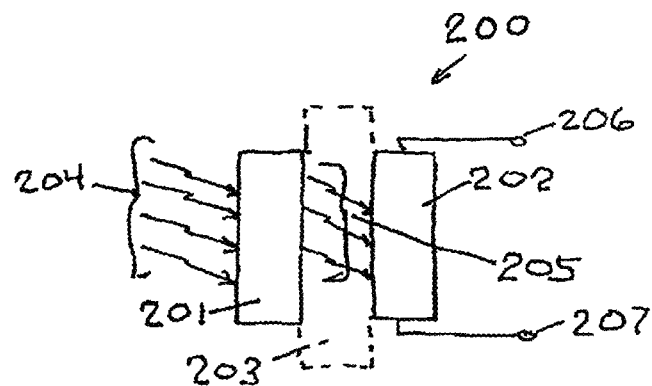
FIG. 24 is a schematic illustration of a generalized hybrid device in accordance with the disclosure hereof.
Figure 25:
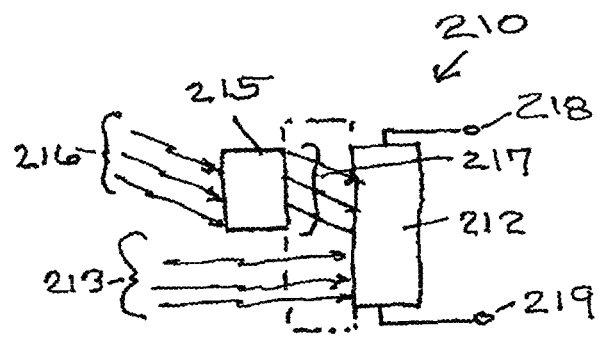
FIG. 25 is a schematic illustration of a further generalized hybrid device in accordance with the disclosure hereof.
Figure 26:
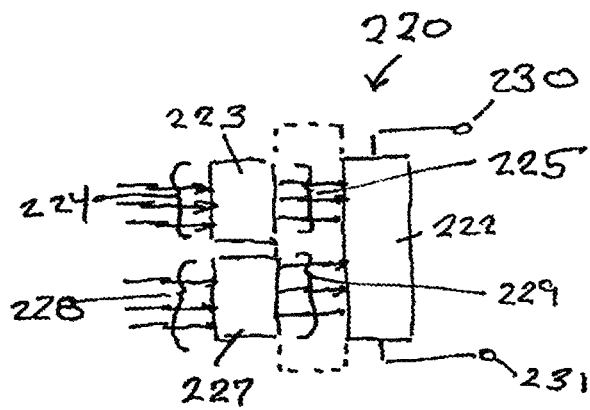
FIG. 26 is still another schematic illustration of another generalized hybrid device in accordance with the disclosure hereof.
Figure 27:
FIG. 27 is a schematic, generalized, enlarged, fragmentary cross-section view of a biological component such as those employed in the devices of FIGS. 24-26 and shows fluorescent units deployed in a matrix.
Figure 28:
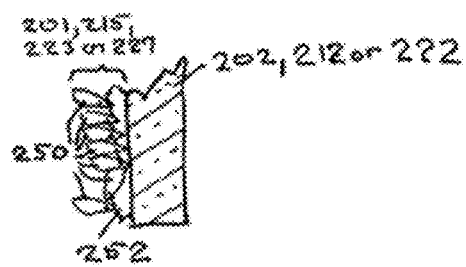
FIG. 28 is a further schematic, generalized, enlarged cross-section view of a biological component such as those employed in the devices of FIGS. 24-26, and shows fluorescent units adherent to the surface of a non-biological photoactive element.

As illustrated schematically in FIG. 24, in some embodiments a biological component 201 receives incident light 204, and emits emitted light 205 in response thereto, and a photoactive non-biological component 202 is disposed in the path of light 205 emitted by the biological component and responds thereto, such as, for example, by producing a voltage, current, or change in impedance between termini 206, 207. In some embodiments, an energy transmitting intermediate layer 203 or another material or component may separate the components 201 and 202. In some embodiments the biological component 201 and the non-biological component 202 may be in direct contact one with the other. In some embodiments as shown schematically in FIG. 25, a photoactive non-biological component 212 may be disposed to receive and respond to both incident light 216 from any source and light 217 emitted by a biological component 215. In some embodiments as shown schematically in FIG. 26, a photoactive non-biological component 222 may be disposed to receive and respond to light 225, 229 emitted by two or more biological components 223, 227, which may be in response to two or more incident light sources 224, 228. As these examples illustrate, a photoactive biohybrid device may include any number of biological components and any number of non-biological components disposed in any relation, configuration, or combination operable to allow direct or indirect transfer of light energy from one or more of the biological components and optionally from one or more other sources. As illustrated in FIG. 27, a biological component may be comprised of a matrix containing the biologically derived entities 250 such as, for example, light antenna structures, some or all of which may be disposed with their light emitting moieties (depicted by dots in FIG. 27) predominantly oriented to emit light in a preferred direction. In some embodiments a biological component 201, 215, 223, or 227 fluoresces, exhibiting what is termed a Stokes shift, the emission of light at a wavelength or wavelengths different from that of light illuminating and activating the biological component. As illustrated schematically in cross-section in FIG. 28, a biological component 201, 215, 223, 227 may include biologically derived entities, such as, for example, light antenna structures, that are directly adherent to a substrate 202, 212, 222, attached to the substrate (which may be or include, for example, a non-biological component or a passive support such as glass) via a linker 252, or in any other manner operable to constrain the biological components or entities from unwanted movement and/or, optionally, in a particular directional orientation, such as, for example with fluorescent or light-emitting regions (indicated by dots in FIG. 28) predominantly oriented toward the substrate, and/or with light-receiving regions oriented toward a light source. A biohybrid device may include any number of biological components and non-biological components which may be disposed in any operable arrangement and combination. The arrangements and combinations illustrated in FIGS. 24-26 are intended as illustrative examples, and it will be apparent to persons of skill in the art that many arrangements and combinations of components, light inputs, packaging, support structures, and other characteristics are possible according to the goals of a particular application. In some embodiments, biological components, such as, for example, light antenna structures, may be affixed to the surface of a non-biological component adhesively, by linking units known in the art as linkers, or in any other manner operable to position the biological components and non-biological components relative to each other in a desired manner.

In some embodiments or applications, a photoactive biohybrid device includes a biological component that is or includes an entity of generally nanoscale dimensions, that is, having a longest dimension in a range of approximately 1 nm, 10 nm, 50 nm, 100 nm, 300 nm, or 500 nm, such as, for example, a light antenna structure. In some embodiments, a large number of biological components are disposed in energy-transmitting relation to one or more non-biological components. In some embodiments, a biological component may be disposed on or in a substrate, which may be or include a non-biological component and/or may be of any material, composition, structure, dimensions, geometry, spatial arrangement or other characteristics operable for an application of interest. An example of a potentially useful substrate material is graphene, which has desirable optical transparency and electrical conductivity properties for some applications. In some embodiments a substrate on or in which a biological component is disposed may be transparent, translucent, or have other optical or photoactive characteristics deemed useful in an application of interest. In some embodiments, a substrate may have selected physiocochemical properties, alone or in combination, such as chemical, electrical, structural, heat transfer, or other properties deemed useful for an application of interest. In some embodiments a biological component may be disposed on a surface of a substrate, disposed between surfaces of one or more substrates, disposed in a chamber present in a substrate, disposed or trapped within a gel, matrix, or colloidal suspension substrate, disposed in a liquid substrate, or disposed in any other position or relationship to a substrate operable for an application of interest. In some embodiments there is provided a plurality of biological components constrained and/or otherwise withheld or suspended in a substrate comprising a gel, matrix, or colloidal suspension, which may, for example, be adapted for applying to a photoactive non-biological component or to another substrate, in the form of a thin film, paint, or coating.

In some embodiments, a biological component may be positionally constrained in any manner operable to confine the biological component in a position or spatial region with respect to a substrate and/or non-biological component. In some embodiments, a biological component may be positionally constrained physically or chemically, such as, for example, by electrostatic forces, by Vander Waals forces, by hydrophobic or hydrophilic interactions, by hydrogen bonding, by an adhesive material, by chemical bonding, by an affinity tag, by attachment to a linker, by adsorption, by surface effects and/or capillary action, by physical entrapment in a chamber or between surfaces, by entrapment in a matrix, gel, foam, or colloidal suspension, or by dissolution or suspension in a liquid. In some embodiments a biological component may be relatively immobilized, such as, for example, by chemical attachment to a solid surface. In some embodiments a biological component may be constrained on a surface with some lateral freedom of movement, such as, for example, by weak adsorption onto a surface. In some embodiments, a biological component may be constrained within a volume, such as, for example, by suspension in a liquid contained in a chamber or between surfaces. A biological component may include or be disposed integrally within a matrix or other material, such as, for example, a clear plastic employed to support or embed active biological units or a liquid such as water or a solvent supporting such units in a suspension such as a colloidal suspension.

In some embodiments, one or more biological components may be disposed in an ordered array, wherein a plurality of biological components are disposed in a manner that is non-random with respect to orientation, spacing, arrangement, or other characteristics. In some embodiments, an ordered array may include a plurality of biological components disposed in the same or similar directional orientation. In some embodiments, an ordered array may include a plurality of biological components disposed in a patterned arrangement such as a grid. Biological components may be oriented and/or disposed in an ordered array using any method or technique operable to obtain a desired disposition, such as, for example, orienting biological components directionally by adsorbing them to a surface having properties that preferentially attract a particular locus, moiety, or region of the biological components (such as by adsorbing biological components having an exposed hydrophobic region to a hydrophobic surface or adsorbing biological components having an exposed hydrophilic region to a hydrophilic surface); orienting biological components directionally by attaching them to a substrate via a linker or affinity tag disposed at a locus or moiety of the biological components; disposing biological components on a pre-patterned surface having regions to which biological components preferentially migrate and/or attach themselves; printing biological components in a pattern on a surface by ink jet type printing; or any other manner operable to produce an ordered array.

In embodiments where a biohybrid device or biological component includes light antenna structures, orienting the light antenna structures can be accomplished in a number of ways. In an embodiment described in detail in an example below, wherein a biological component includes RC– light antenna structures disposed on a glass substrate, because the light antenna structures of that example, when stripped of their reaction centers, have a hydrophobic portion or base plate at the light emitting end, a hydrophobic glass slide was used to support the light antenna structures, causing the hydrophobic portion of the light antenna structures to come to rest on the slide. Other techniques for manipulating nanoparticles such that their orientation can be assured are addressed in the literature. See, for example, Lavan, D. et al., "Approaches for biological and biomimetic energy conversion," 5251-55, PNAS, vol. 103, no. 14, 2006; Morris, C. et al., "Self-Assembly for Microscale and Nanoscale Packaging Steps Toward Self-Packaging," 601-11, IEEE Transactions on Advanced Packaging, vol. 28, No. 4, 2005; Yoshino, M. et al., Engineering surface and development of a new DNA micro array chip," 274-86, Wear 260, 2006; Kane, R. et al., "Patterning proteins and cells using soft lithography," Biomaterials 20, 2363-76, 1999. Each of the foregoing is incorporated herein by reference.

In some embodiments a non-biological component is photoactive. A photoactive component or material may be any component or material having any function or characteristic that is altered or affected by light or that affects, alters, processes, or transduces light. Photoactive components or materials may include components or materials that operate according to any modality useful in a particular application, such as, for example, photovoltaic, photoconductive or photoemissive components or materials. Photovoltaic materials are materials that produce an electrical potential upon exposure to light, and may include, for example, those listed in Table C. Photoconductive materials are materials that exhibit decreased electrical resistance when exposed to infrared rays, visible light or ultraviolet light. Photoconductive materials include, for example, cadmium selenide, cadmium sulfide, germanium, lead sulfide, selenium, silicon and thallous sulfide. Photoemissive materials are substances that emit electrons when exposed to infrared, visible light or ultraviolet radiation. Photoemissive materials include, for example, cesium, potassium, rubidium and sodium. In some embodiments, photovoltaic, photoconductive, photoemissive, or other photoactive materials may be chosen so that they are responsive (or have heightened responsivity) to illumination by light in the region of the spectrum emanating from a biological component. Photoactive components may also include charge coupled devices; photomultiplier devices; photodiode devices; photographic devices, films, and materials; devices that operate via fluorescence resonance energy transfer ("FRET"); pyroelectric photodetectors; photoactive chromophores; thermal or infrared detectors; photo transistors; and/or devices or materials that operate according to any other modality or mechanism operable to affect or respond to light, whether currently known or developed in the future. Photoactive components or materials may include components or materials that affect or respond to light having any energy, intensity, wavelength, combination of wavelengths, spectral density, or other characteristics attendant to an application of interest, including, for example, light in the visible range, the infrared range, the ultraviolet range, and or any combination thereof. In some embodiments, a non-biological component may include a photoactive semiconductor material or device, which may be composed in whole or in part of inorganic semiconductor materials, organic semiconductor materials, semiconductor materials of biological origin, composites such as metal-semiconductor-metal photodetector materials, complementary metal-oxide semiconductors (CMOS), or any other semiconductor materials having photoactive properties whether currently known or developed in the future. In some embodiments, the composition of a non-biological component includes a photoactive semiconductor material or device such as, for example, a silicon photovoltaic material or cell. In an embodiment, light emitted from a biological component and received by a photoactive non-biological component causes the photoactive non-biological component to exhibit its characteristic photoactive behavior, such as, for example, developing a voltage, exhibiting a change in resistance or emitting electrons. In some embodiments of photoactive biohybrid devices the light energy communicated from a biological component to a photoactive non-biological component may be transmitted other than by emission of photons, such as, for example, by the mechanism known as FRET (fluorescence resonant energy transfer).

In some embodiments where the biological component is light-emitting and the non-biological component is photoactive, the photoactive non-biological component is disposed so as to receive, directly or indirectly, light energy emitted by the biological component, such as, for example, by disposing the photoactive non-biological component directly in the path of light emitted by the biological component; or by conducting light from the biological component to the non-biological component via one or more gaps, transparent or translucent media (such as, for example clear plastic or glass), lenses, filters, mirrors, optical fibers, or other passive light-transmitting components; or by disposing a photoactive non-biological component including one or more FRET receptors in relation to FRET donors in a biological component in any manner operable to transmit energy by FRET; or in any other manner operable to communicate light energy from a biological component to a photoactive non-biological component.

In some embodiments, a biohybrid device includes a biological component that responds to light, such as, for example, by receiving incident light and emitting emitted light in response thereto, by receiving light and transducing the light energy to another form, by receiving light and emitting a chemical or other signal, or in any other manner; and a non-biological component that performs a function in response to material, energy, or information received from the biological component.

In some embodiments, a biological component is a light antenna structure or includes one or more light antenna structures, which may be RC− light antenna structures or force-adapted light antenna structures. As used herein, "light antenna structures" refers to biological components that are or include light-harvesting components obtained from light-harvesting antennas, which are "pigment-protein complexes that absorb light and transfer energy to the photosynthetic reaction centers" in photosynthetic organisms. Green, B. R. and Parson, W. (Eds.), Light-Harvesting Antennas in Photosynthesis, Advances in Photosynthesis and Respiration, vol. 13, Kluwer Academic Publishers (2003). These light harvesting components include at least a plurality of chromophores and/or pigments, which may be self-organizing, arranged on a protein or polypeptide scaffold, or otherwise disposed or arranged so as to operate cooperatively, in a manner operable to allow the gathering and "funneling" of light energy from the chromophores and/or pigments. In photosynthetic organisms, it is common for light-harvesting antennas to include or be coupled with reaction centers, where the light energy is used to drive photochemical or other reactions. "The more distal parts of the antenna system . . . maximally absorb photons at shorter wavelengths than do the pigments in the antenna complexes that are proximal to the reaction center . . . . [T]he excited states populated by short-wavelength photons are relatively high in energy. Subsequent energy transfer processes are from these high-energy pigments physically distant from the reaction center to lower-energy pigments that are physically closer to the reaction center. With each transfer, a small amount of energy is lost as heat, and the excitation is moved closer to the reaction center. The energy lost in each step provides a degree of irreversibility to the process, so the net result is that the excitation is 'funneled' into the reaction center, where some of the energy in it is stored by photochemistry." Blankenship, R., Molecular Mechanisms of Photosynthesis, p. 66, John Wiley & Sons 2002. In some embodiments a light antenna structure may consist of or include a plurality of light-harvesting molecules, structures, or components, together with other material, combined into a composite entity (such as, for example, the RC− chlorosomes disclosed herein), as would often be the case for structures extracted from organisms where it is impracticable and unnecessary to separate out individual molecular structures.

In some embodiments of biohybrid devices disclosed herein, it is desired to intercept the energy from biological light-harvesting apparatus before it is converted from light to some other form. This may be accomplished by employing biological components that include RC− (reaction center minus) light antenna structures. As used herein, "RC−" denotes light antenna structures that include light-harvesting antennas, or light harvesting components of light-harvesting antennas, that are normally coupled directly or indirectly to reaction centers in their natural state in the photosynthetic organisms from which they are derived, but from which the reaction centers have been removed, inactivated, or otherwise decoupled, so that light energy gathered by the light antenna structures is re-emitted as light energy. RC− light antenna structures offer several advantages over simpler photoactive entities such as lone pigments or chromophores, in that they gather and funnel light from a larger and relatively diffuse region and emit the light in a more localized manner, thereby facilitating directional orientation of the emitted light; and they emit light that is wavelength-shifted from the incident light, thereby enabling their use to process light so as to better conform to the responsive properties of photoactive non-biological components. As an alternative to the use of RC− light antenna structures, in some embodiments or applications of biohybrid devices, a biological component may include light antenna structures coupled to reaction centers and/or other associated biological entities, and a non-biological component may be disposed to respond to a charge separation or other electronic or chemical signal produced by the reaction centers or other entities.

Unless monochromatic, a light source typically produces light that represents a combination of various wavelengths that are present at various intensities. The combination of specific wavelengths present and their intensities is referred to herein as the "spectral content" of the light, and may be represented as a function or graph of intensity vs. wavelength. In some embodiments, a biological component, such as, for example, an RC– light antenna structure, has characteristic absorption and emission bands; that is, a wavelength or wavelength range at which it absorbs light and a wavelength or wavelength range at which it emits light, respectively, when operated under ideal or optimal conditions. Table B shows absorption and emission wavelengths for various photosensitive biological entities listed in Table A. In some embodiments, a biological component includes light antenna structures that emit emitted light in response to light incident thereon, and the spectral content of the emitted light differs from the spectral content of the incident light, such as, for example, where the emitted light is Stokes-shifted with respect to the incident light. In some embodiments, the emitted light more closely conforms to desired spectral characteristics than does the incident light. This enables the advantageous use of such components to improve the performance of photoactive non-biological components, by receiving incident light whose spectral content does not match the ideal input characteristics of the photoactive non-biological component and transforming it into emitted light that more closely conforms to the ideal input characteristics. For example, in some embodiments, a photoactive non-biological component may respond optimally to light in a range of wavelengths different from the wavelengths predominantly present in the available incident light. The characteristic spectral sensitivities of various representative photoactive non-biological materials are enumerated in Table C, right-hand column. A biological component including a light antenna structure may receive the available incident light and emit light in which the intensities of the wavelengths to which the photoactive non-biological component ideally responds are relatively increased in comparison to the incident light. In some embodiments of biohybrid photoactive devices, it is preferable that the biological components be arranged in light communicating relation with the photoactive non-biological component located so as to receive light emitted by the biological component. Also, it may be advantageous in an embodiment to employ biological components that, when illuminated with light predominantly in one region of the spectrum, emit, and optionally communicate to a photoactive non-biological component, light whose intensity is relatively increased in another, different region of the spectrum to which the photoactive non-biological component preferentially responds.

A biohybrid device according to the disclosure hereof may be packaged, encapsulated, supported, and/or provided with interfaces for interfacing with other devices or components, in any manner compatible with its purpose and functioning and employing any of the many materials, techniques, and modalities familiar to persons of skill in the art of packaging of devices. A photoactive biohybrid device should preferably be packaged using transparent materials or otherwise in a manner that facilitates exposure of its light-receiving elements to light. Packaging should preferably protect the components of the device, particularly the biologically derived components, from exposure to potentially damaging environmental conditions or substances. In some embodiments, biohybrid devices may be packaged in modules or subcomponents to enable user-determined configurations or combinations. For example, biological components such as light antenna structures may be disposed on a film or sheet for later use or application in association with a photoactive non-biological component or other device. In some embodiments there is provided a plurality of biological components constrained on or in a film or sheet, which may, for example, be adapted to be applied by another manufacturer, installer, or end user to a photoactive non-biological component such as a photovoltaic cell. A film or sheet may include any of the many materials recognized by persons of skill in the art as film or sheet materials, and operable for constraining and/or supporting biological components as described here and deemed useful in an application of interest. A film or sheet may have any dimensions, geometry, and/or optical or other properties found useful for an application of interest, which properties may be isotropic or may differ according to direction or other spatial disposition. In some embodiments, a film or sheet is flexible, generally transparent, and has a thickness less than 0.5 mm. In some embodiments, biological components such as light antenna structures may be applied to a substrate as a thin coating, having a thickness greater than or on the order of the major length axis of the biological component. In some embodiments it will be found useful to employ as substrates materials that are transparent, reflective, or absorptive of light at one or more wavelengths and/or ranges of wavelengths. Examples of film or sheet materials that may be employed as substrates or layers thereof according to the disclosure hereof include any of the many materials known in the art of photographic film making, window coatings, video display screens and protectors, adhesive or other tapes, and other applications involving the use of thin substrates as supports or carriers for functional entities that require structural backing or support. Examples of such materials include, without limitation, cellulose nitrate, cellulose acetates, polyester, acetate-based resin, polyester-based resin, polyether-sulphone-based resin, polycarbonate-based resin, polyamide resin or polyimide resin, polyolefine-based resin or acrylic-based resin, polyether-based resin or polyvinyl chloride, styrene-based resin or norbornane-based resin, mylar, carbon composites, glass, and graphene. A film or sheet may include a single layer or a plurality of layers, which may have differing compositions, dimensions, geometry, and or optical, physicochemical, or other properties.

In some embodiments a biological component is force-adapted by subjecting an organism or adaptive system to adaptation-inducing environmental conditions so as to produce desired characteristics in the biological component that differ from those of a biological component derived from an organism or adaptive system that has not been subjected to such conditions. In the context of this disclosure, an adaptive system may be or include one or more organisms, populations of organisms, expression systems, or other sources from which a biological component is derived. Adaptation-inducing environmental conditions may be any conditions to which an organism or adaptive system is subjected, which may be conditions determined by ascertaining a relation between the environmental conditions and the desired characteristics and employing that relation to determine values of the environmental conditions corresponding to the desired characteristics. In some embodiments, the environmental conditions are operable to produce an adaptation whereby biological components derived from the adaptive system have desired characteristics that differ from those produced by a wild type or unadapted organism or adaptive system. As used herein, an adaptation may be any change in phenotype, genotype, characteristics, or responsiveness of an organism or adaptive system or any material or component obtained therefrom in response to applied environmental conditions, whether attributable to a genetic change, a change in transcription, translation, signaling, or by any other mechanism whether known or unknown. Environmental conditions may include any conditions to which an organism or adaptive system is subjected and operable to produce an adaptation, including, by way of example only, physical conditions such as, for example, temperature, pressure, volume of container, quantity of nutrients provided, freedom of movement, and light exposure and spectral content and intensity thereof; chemical conditions such as, for example, acidity, media composition, and concentration of any chemical substance; temporal conditions, such as, for example, the frequency, repetition, duration, and/or scheduling of any environmental conditions or changes therein; and/or mechanical conditions, such as, for example, stirring, mixing, centrifugation, shearing, or vortexing.

In some embodiments the methods, apparatus, and compositions disclosed herein may be employed to produce an orthogonal force-adaptation; as used herein, an orthogonal force-adaptation is an adaptation affecting a characteristic other than the tolerance of the organism to the environmental condition(s) producing the adaptation. For example, producing organisms tolerant of high temperature by growing populations at high temperature would not, by itself, involve an orthogonal adaptation, but if it were determined that growing populations of photosynthetic bacteria at high temperature would produce light antenna structures capable of Stokes-shifting a larger proportion of blue light incident upon them, the latter would be an orthogonal adaptation. Similarly, for example, antibiotic resistance produced by growing a population of bacteria in the presence of the antibiotic would be a forced adaptation, but not an orthogonal adaptation; however, if growing bacteria in the presence of an antibiotic caused an adaptation whereby light antenna structures produced by the bacteria had a higher pigment content than in the original population, the latter would be an orthogonal adaptation.

In general, the environmental conditions under which an organism or adaptive system undergoes a desired force-adaptation may be determined in any manner and by any method operable to reveal a condition or set of conditions effective to produce the adaptation in question, including, for example, trial and error. It is preferable to determine an objective measure for evaluating whether and/or to what degree a desired adaptation has occurred. Such a measure may include a direct measure of a characteristic of the organism or adaptive system; in some embodiments such a measure may preferably be or include a figure of merit. In some embodiments, such a measure may include a measure of a characteristic of a biological component obtained from the organism or adaptive system, and/or a characteristic of the performance of such a component. In some embodiments such characteristics may be characteristics of the biological component and/or of its performance when incorporated in a biohybrid device.

Figures 21A, 21B, 21C:
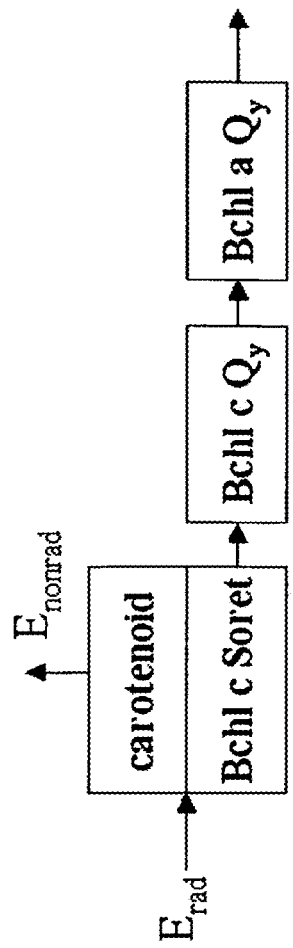
FIG. 21 shows a formula for the photonic figure of merit devised for *C. aurantiacus* (FIG. 21(a)); a tabulation of the measures going into that formula for seven specimens (FIG. 21 (b)); and a block diagram illustrating the interaction of the major contributing factors to the figure of merit (FIG. 21(c))

In some embodiments, a figure of merit ("FoM") is devised that quantifies the degree to which the characteristics of a biological component conform to desired characteristics. A figure of merit may be expressed in terms of a relation or function whose input(s) are measurable or estimable properties of a biological component, and the output, the figure of merit, is a quantity determined therefrom. The figure of merit may be expressed in any manner appropriate to the characteristics being described, such as, for example, as a scalar quantity, a vector, or a textual or other descriptor. In some embodiments, the figure of merit quantifies characteristics relating to the performance of a biological component when incorporated into a device. In some embodiments wherein a biological component includes one or more light antenna structures, a useful figure of merit is a quantity indicative of the abundance in the structures of pigments that contribute to the desired Stokes shift or other desired behavior, relative to the abundance of pigments that do not contribute or that quench or otherwise detract from the desired behavior. The relative abundances of particular pigments may be estimated or approximated by measuring the absorbance by the light antenna structures of the specific light wavelengths whose absorbance is attributable to particular pigments of interest. Thus a figure of merit may be or include one or more ratios (or reciprocals thereof) of absorbance by the light antenna structures at a wavelength characteristic of the absorbance of a desired pigment to the absorbance by the same light antenna structures at a wavelength characteristic of the absorbance of an undesired pigment. A figure of merit of this kind is shown in FIG. 21a for RC– chlorosomes, and elaborated in greater detail in the examples below. It will be apparent to persons of skill in the art that a figure of merit based on ratios of absorbances as just described can readily be devised for use in force-adapting and/or evaluating any light antenna structure, given a basic understanding of which pigments contribute to desired behavior.

In some embodiments, an objective function is determined embodying a relation between environmental conditions applied to an adaptive system, and the characteristics of a biological component derived therefrom. "Objective function" is used herein to mean any function, relation, or model relating one or more inputs of a system with one or more outputs. In the present context, the adaptive system may be an organism, population of organisms, expression system, or other source from which a biological component is derived, the inputs may be environmental conditions to which the system is subjected, and the output may be a measure of characteristics of a biological component, which may be expressed in terms of a figure of merit. An objective function may be determined by multiple-input, multiple-output experimental techniques, or may be determined analytically, by other experimental methods, or in any other way operable to determine, estimate, or model the relation between the inputs and outputs of interest. Multiple-input, multiple-output techniques may be employed wherein a plurality of replicates or instances of the adaptive system are subjected to differing values of inputs, such as environmental conditions, while holding other conditions constant across all replicates or instances; outputs, such as the characteristics of biological components derived from each such replicate or instance, are measured, and a relation between inputs and outputs may be determined therefrom by fitting a suitable function, by devising a computational model, or by any of the many methods known to persons of skill in the art for modeling relations between the inputs and outputs of a system.

In some embodiments, adaptation-inducing environmental conditions may be determined by ascertaining an objective function relating environmental conditions to characteristics of interest of a biological component, and determining from the objective function particular environmental conditions corresponding to desired characteristics. Given desired characteristics, which may be expressed as a figure of merit value, adaptation-inducing environmental conditions corresponding thereto may be determined by inverting the objective function, by numerical solution of the objective function, or by any of the many other methods known to persons of skill in the art for determining or estimating function inputs corresponding to a given output.

In some embodiments a force-adapted light antenna structure is obtained as follows: a population of organisms capable of producing light antenna structures, such as, for example, photosynthetic bacteria, is divided into a plurality of subpopulations, such as, for example, nine approximately identical subpopulations. A plurality of environmental conditions is selected for variation, such as, for example, temperature, light intensity, and media volume. A range of values for each of the selected environmental conditions is chosen and a plurality of specific values of each is selected, such as, for example, three distinct temperatures, three distinct light intensities, and three distinct media volumes, as illustrated by way of example in FIG. 22. The subpopulations are grown under each possible combination of the selected factors; for example, with three environmental factors and three selected values of each, 27 distinct combinations are possible. A further subpopulation may be grown under normal conditions as a control. In some embodiments the subpopulations are grown in a MIMO/EC device as illustrated in FIG. 23 and described in detail in the examples below. After a suitable period of growth, light antenna structures are obtained from each population and a characteristic of their performance is measured. For example, a figure of merit as disclosed herein is measured for light antenna structures from each subpopulation, or light antenna structures from each subpopulation are incorporated into biohybrid devices and device performance is measured. The combination of environmental conditions producing the most favorable performance values may then be applied to a production population and light antenna structures may be produced for incorporation into biohybrid devices. In some embodiments, an objective function is derived relating the values of the applied environmental conditions to the measured performance, and a set of values of environmental conditions that optimizes the objective function is determined and applied to the production population. It will be apparent that the set of values of environmental conditions that optimize the objective function may include values that lie between or outside the values actually used in the experiments. It should be noted that the variation of a plurality of environmental conditions together provides an important advantage, since the relationship of a given environmental condition to performance may typically not be independent of the values of other environmental conditions.

In embodiments, there is provided a method of producing a force-adapted population including organisms expressing force-adaptively optimized extractable biological components. In embodiments, a method may include providing a population of organisms expressing an extractable biological component having a characteristic desired to be optimized; segregating the population into a plurality of subpopulations; selecting one or more environmental variables; evaluating a measure of the characteristic desired to be optimized in each sub-population after subjecting each subpopulation during growth to values of each of the selected environmental variables, each sub-population being subjected to a different selection of such values; and/or selecting from the plurality of sub-populations a preferred sub-population in which the characteristic desired to be optimized is altered in comparison to naturally occurring organisms of the same species. In embodiments, a method may include propagating a preferred subpopulation or force-adapted population, optionally while maintaining or repeating the environmental conditions imposed on the preferred subpopulation or force-adapted population so as to maintain the stability of the desired adaptation in the population.

In some embodiments, a biological component may include light antenna structures and/or light-harvesting antennas and/or light-harvesting components thereof that may be produced, isolated, extracted, or derived from photosynthetic or photosensitive organisms, such as, for example, those enumerated in Table A, first column, and which may include photoactive materials such as those indicated in Table A, columns 2 through 11. Table B gives the wavelengths of absorbed and emitted light of the photoactive materials identified in Table A either in an appropriate solvent, in the case of the chlorophylls, or standing alone in the cases of the carotenoids and bilins.

In some embodiments, a photoactive non-biological component may be composed in whole or part of one or more of the materials enumerated in Table C, column 1, whose typical spectral sensitivities are indicated in Table C, right-hand column. Table D lists exemplary pairings of photosensitive biological materials from Table A with photoactive non-biological materials from Table D, wherein the wavelength of light emitted by the photosensitive biological material more closely corresponds to the spectral sensitivity of the non-biological material than does the maximum absorption wavelength region of the photosensitive biological material. In biohybrid device embodiments according to these pairings, incident light in the maximum absorption wavelength region of the photosensitive biological material as indicated is absorbed by light antenna structures containing the photosensitive biological material, and re-emitted at a longer wavelength that better matches the spectral sensitivity of the non-biological photoactive material with which it is paired. Thus, A biohybrid device may be constructed based on any one or more of the pairings shown, by incorporating RC– light antenna structures containing the indicated photosensitive biological material together with a photoactive non-biological component comprising the paired photoactive non-biological material, to produce a biohybrid device that exhibits the characteristic photoactivity of the non-biological component when illuminated with light in the spectral region to which the non-biological component is insensitive or has less than desired sensitivity. In some embodiments, biological components may include light antenna structures and/or light-sensitive materials derived from one or more organisms and/or light harvesting structures or components, such as those enumerated in Table A, in combination to produce emitted light having a desired spectral content in response to incident light. (The Table A listing of photoactive biological materials is not exhaustive. Suitable photoactive biological materials other than those listed may be known or may be developed from species not yet known, and the scope of this disclosure extends to all such materials.)

In each of the organisms identified in Table A, the photoactive protein or protein pigment is present in an antenna structure. The methodology for isolating the unit that forms part of that antenna structure containing the identified photoactive pigment or pigment protein is well documented in the literature. One or more of the publications listed below under Isolation, Separation and Harvesting Techniques for Light Antennas and Subunits sets forth techniques for isolating fluorescent units identified as useful in practicing various embodiments of the disclosure hereof. Each publication listed is incorporated herein by reference.

In some embodiments, isolating the chosen structure entails first isolating the antenna structure, and then removing from that antenna structure one or more of the reaction centers that ordinarily absorb light at wavelengths emitted by the antenna structure to produce protons. By removing the reaction center(s), light that would otherwise be absorbed by the reaction center(s) can be emitted. Other structure that does not contribute to the Stokes shift phenomenon, or that interferes with the emission of light by the light antenna structures, may be removed and discarded as well.

TABLE A

Photosynthetic Pigments and Pigment Proteins Utilized in Light Antenna Structures from Various Biological Organisms*

| Organism | Chl a | Chl b | Chl c | Chl d | B Chl a | B Chl b | B Chl c, d, e | B Chl g | Carote-noids | Bilins |
|---|---|---|---|---|---|---|---|---|---|---|
| Purple Bacteria | | | | | + | + | | | + | |
| Green Sulphur Bacteria | | | | | + | | + | | + | |
| Green Nonsulphur Bacteria | | | | | + | | + | | + | |
| Heliobacteria | | | | | | | | + | + | |
| Cyanobacteria | + | + | + | + | | | | | + | + |
| Green Algae | + | + | | | | | | | + | |
| Diatoms | + | | + | | | | | | + | |
| Brown Algae | + | | + | | | | | | + | |
| Dinoflagellates | + | | + | | | | | | + | |
| Cryptomonads | + | | + | | | | | | + | + |
| Red Algae | + | | | + | | | | | + | + |
| Plants (e.g. maize) | + | + | | | | | | | + | |

Chl a = Chlorophyll a; Chl b = Chlorophyll b; Chl c = Chlorophyll c; Chl ad = Chlorophyll d B Chl a = Bacterial Chlorophyll a; B Chl b = Bacterial Chlorophyll b; B Chl c = Bacterial Chlorophyll c; B Chl d = Bacterial Chlorophyll d.
*Ref: Molecular Mechanisms of Photosynthesis, R. Blankenship. Blackwell Scientific, 2002.

TABLE B

Spectroscopic Properties of Chlorophylls and Bacteriochlorophylls in Vitro and of Pigments*

| Pigment | Solvent | Absorption (max) [nm] | Emission† |
|---|---|---|---|
| Chl a | diethyl ether | 662, 578, 430 | 670 |
| Chl b | diethyl ether | 644, 549, 455 | 652 |
| Chl c | pyridine | 640, 593, 462 | 648 |
| Chl d | diethyl ether | 668, 447 | 696 |
| B Chl a | diethyl ether | 773, 577, 358 | 781 |
| B Chl b | acetone | 791, 592, 372 | 800 |
| B Chl c | diethyl ether | 659, 429 | 667 |
| B Chl d | diethyl ether | 651, 423 | 659 |
| B Chl e | acetone | 649, 462 | 657 |
| B Chl g | acetone | 762, 566, 405, 365 | 770 |
| Carotenoids (Range) | | 400-500 | 550-675 |
| Billins (Range) | | 550-650 | 560-660 |
| Billproteins (Range) | | 540-660 | |

* Ref:
Molecular Mechanisms of Photosynthesis, R. Blankenship, Blackwell Scientific, 2002.
† Estimated.

TABLE C

Materials Used for Photovoltaics (PVs)

| Engineered Material | Eff* (%) approx | Use* | Spectral Sensitivity** |
|---|---|---|---|
| Inorganic PV Materials* | | | |
| Amorphous Silicon | 10 | Most Common Form of Thin Film PV | UV & IR Low; Highest (550-650) |
| Cadmium Telluride (CdTE) | 17 | Sig & Growing Share of Thin Film PV Market | UV Low; Highest @ IR ~900 nm |
| Cu—In—Ga—Se | 20 | Growing Share of Thin Film Market | UV Low; Highest 600-800 nm |
| Poly(micro) Crystalline Silicon | 20 | Widely USed | Highest @~500-600 nm |
| Monocrystalline Silicon | 25 | Most Common PV Material In Use Today | UV Low; Vis Mod; High (750-1000) |
| Indium Phosphide | 22 | In Lab R&D Only | UV & IR Low; Highest @600-800 nm |
| Gallium Arsenide (GaAs) | 25 | Not Widely Used Yet | UV Low; Highest @ 900-1200 nm |
| GaAs/InP/Ge Hybrid | 35 | Lab R&D Only | |
| Organic PV Materials # | 4 to 8 | Currenlty Under Commercialization | Peak QE Range: 400-650 |
| Doped Pentacene Homojunction | 2.4 | | 36% @ 650 nm |
| spiro-OMeTAD† | 2.56 | Dye-Sensitized Solar Cell Technology | 38% @ 520 nm |

TABLE C-continued

Materials Used for Photovoltaics (PVs)

| Engineered Material | Eff* (%) approx | Use* | Spectral Sensitivity** |
|---|---|---|---|
| MDMO-PPV-PCBM†† | 2.5 | | 50% @ 470 nm |
| Cu phthalocyanine/C60 | 3.6 | | 18% @ 620 nm |

*Efficiencies from cited reference: 'Positioning-Thin Film Photovoltaics for Success' A Nanomarkets White Paper March 2008; www.nanomarkets.net

**Estimated

From ref: Organic Photovoltaic Films, Materials Today, May 2002, p23

†2,20 7,70-tetrakis(N,N-di-p-methoxyphenyl-amine)-9,90-spirobifluorene (spiro-MeOTAD)

††MDMO-PPV (poly)|2-methyl,5-(3*,7** dimethyl octyloxy)]-p-phenylene vinylene): PCBM ([6,6]-phenyl C61 butyric acid methyl ester)

TABLE D

Biohybrid Combinations of Engineered PV Components and Bioderived Light Antenna Components

| Biohybrid Example | Biophotonic Abs nm | Exemplary Bioderived Component B | Biophotonic Emiss [max] | Pairing Engineered Component A | Engineered Abs [nm] | Relative Output Rel to Eng Mat |
|---|---|---|---|---|---|---|
| 1 | 470/740/750 | Chlorosomes (from different species) | 772/805/808 | Monocrystalline silicon | 750-1000 | Efficiency > 25% |
| 2 | 670 | LHCI | 730 | Monocrystalline silicon | 750-1000 | Efficiency > 25% |
| 3 | 470/670/740 | Chlorosome + LHCI | 730 + 808 | Monocrystalline Silicon | 750-1000 | Efficiency > 25% |
| 4 | | FMO Protein(BChl a) | 785 | Monocrystalline silicon | 750-1000 | Efficiency > 25% |
| 4 | See below | Phycobilisomes (all) (alone or in comb) | 537 – 660 | Amorphous Silicon | 550-650 | Efficiency > 10% |
| 4a | 565 (495) | R-Phycoerythrin | 575 | Amorphous Silicon | 550-650 | Efficiency > 10% |
| 4b | 545 | B-Phycoerythrin | 575 | Amorphous Silicon | 550-650 | Efficiency > 10% |
| 4c | ~495 (545) | Y-Phycoerythrin | ~563 | Amorphous Silicon | 550-650 | Efficiency > 10% |
| 4d | 615 | C-Phycocyanin | 647 | Amorphous Silicon | 550-650 | Efficiency > 10% |
| 4e | 617 (555) | R-Phycocyanin | 637 | Amorphous Silicon | 550-650 | Efficiency > 10% |
| 4f | 652 | Allophycocyanin | 660 | Amorphous Silicon | 550-650 | Efficiency > 10% |
| 4g | 566 | Phycoerythrin 566 | 617 | Amorphous Silicon | 550-650 | Efficiency > 10% |
| 4h | 575 | Phycoerythrocyanin | 625 | Amorphous Silicon | 550-650 | Efficiency > 10% |
| 5 | 375/800/850 | LH2 | ~800 | Indium Phosphide | 600-800 | Efficiency > 22% |
| 6 | 470/710/750 | Chlorosomes | 772/805/808 | Indium Phosphide | 600-800 | Efficiency > 22% |
| 7 | 773, 577, 358 | FMO Protein | 785 | Cu—In—Ga—Sc | 600-800 | Efficiency > 20% |
| 8 | 644, 549, 455 | Chl b | 648 | Doped Pentacene Homojunc | 650 | Efficiency > 2.4% |

Note:
utilizing methods taught in specification, biophotonic structures can be engineered to acquire different biophotonic and other desired properties, e.g. absorbance and emission values, to obtain desired figures of merit that exceed engineered materials alone when put into exemplary pairings such as depicted in above biohybrid examples Table E relates species, light antenna structure, and pigment and/or pigment protein with wavelengths of absorbed light and emitted light.

TABLE E

Biophotonic Light Antenna Structures and Light Absorption Emission Values

| Light Antenna Structure | Pigment or Pigment-Protein Complex | Absorption (Max) [nm] | Emission† [nm] | Specie |
|---|---|---|---|---|
| PERIPHERAL MEMBRANE | | | | |
| Phycobilisomes [Bilins + Biliproteins] | Bilins phycocyanobilin phycoerythrobilin | 550-650 | | Cyanobacteria/Red Algae |
| " | Biliproteins | 540-660 | 560-660 | |
| " | R-Phycoerythrin | 565 (495) | 575 | Red Algae |
| " | B-Phycoerythrin | 545 | 575 | Cyanobacteria/Red Algae |
| " | Y-Phycoerythrin | ~495 (545) | ~563 | Cyanobacteria |
| " | C-Phycocyanin | 615 | 647 | Cyanobacteria/Red Algae |
| " | R-Phycocyanin | 617 (555) | 637 | |
| " | Allophycocyanin | 652 | 660 | Cyanobacteria/Red Algae |
| " | Phycoerythrin 566 | 566 | 617 | |
| " | Phycoerythrocyanin | 575 | 625 | |
| | | | | Green Sulphur Bacteria |
| Chlorosome | B chl c, d, e | 659, 429/651, 423/649, 462 | 808 | *Chloflexus Aurantiacus* |
| Chlorosome | BChl c, a, Carot, Quin | 470/750 | 772 & 805 | *Chlorobium tepidum* |
| FMO Protein | B Chl a | 773, 577, 358 | 785 | *Fucus Serratus* |
| LH2 Complex | B Chl a, Carotenoid | 850, 800, 750-470 | 890 | *Rhodopseudomonas Acidophila* |
| | | | | Green Sulphur Bacteria |
| Peridinin-Chlorophyll Protein (PCP) | B Chl a & Carotenoid | 660, 535, 437, 350 | 679, 675 | Dinoflagellates |
| LH2 Complex | BChl/Carot/prot subunits | 800-850 (375) | ~860 | Purple Bacteria |
| INTEGRAL MEMBRANE Fused | | | | |
| PS1 RC Complexes | chlorophyll; B-carotene | 430-660 | ~700 | Plants, Algae, Cyanobacteria |
| Green Sulp Bact RC Complex | Bchl a; carotenes | 450-850 | ~860 | Green Sulphur Bacteria |
| Heliobact Bact RC Complex Core | Bchl a; carotenes | 450-850 | ~860 | Heliobacterial |
| CP43 & CP47 Complex PS2 | Chl a & œ-Carotene | 660, 450, 430 | ~700 | Plants, Algae, Cyanobacteria |
| LH1 Complex | B Chl a & œ-Carotene | 875 (380) | ~860 | Anoxygenic Bacteria |
| Accessory | | | | |
| LHCI Complexes of PS1 | Chl a & Chl b | 676, 470 | 715-735 | Plant (Maize) |
| LHCII of PS 2 | Chl a & Chl b | 675, 650 | 679 | Plants & Algae |
| LH2 Complex | | 832 (~375) | 800 | Purple Bacteria |
| PS 2 | Chl a PSI & PSII | 450 | 710 | Algae (Diatom-*PTricornutum*) |

†estimates
FMO = Fenna-Mathews-Olson LH1 = Light Harvesting 1 Complex; LH2 = Light Harvesting 2 Complex PSI = Photosystem I; PSII = Photosytem II LHCI = Light Harvesting Complex I; LHCII = Light Harvesting Complex II; Bacterial RC = Bacterial Reaction Center
*References:
Molecular Mechanisms of Photosynthesis, R Blankenship, Blackwell Scientific, 2002.
Photosynthesis (Third Edition), David W Lawlor, BIOS Scientific Publishers, 2001.
Probing Photosynthesis, Mechanisms Regulation & Adaptation, M Yanus, U Parthre, O Nohanty Eds), Taylor & Fancis, 2000.
Chlorophylls and Bacteriophylls, B Grimm, R J Porra, W Rudiger, H Scheer, Eds., Springer, 2006.

In some embodiments, the biological component includes light antenna structures that contain photoactive pigments and/or pigment proteins disposed in nanoscale structures of various shapes, and the light antenna structures may be directional in their light absorbing and emitting abilities, such as, for example, preferentially absorbing light at a first locus or region and/or from a first direction, and emitting predominantly from a second locus or region and/or in a second direction. In such embodiments it is preferable that light antenna structures be disposed in a position and orientation such that their light-absorbing moieties are oriented toward the incident light and their light-emitting moieties are oriented so as to emit light predominantly in the direction in the direction in which it is desired for the biological component to emit light.

By incorporating in a biohybrid device two or more biological components, such as, for example, RC– light antenna structures, having different characteristic absorption and emission wavelengths, a component or device can be engineered having a composite response optimized for compatibility with the response characteristics of an arbitrary photoactive non-biological component. This can be accomplished by determining the preferred output wavelengths or wavelength ranges at which maximum intensity is desired (such as, for example, the wavelengths to which a photoactive non-biological device is optimally responsive); determining the wavelength or wavelength ranges of predominant intensity in the incident light to which the device is intended to respond; selecting two or more biological components each having, to the extent feasible, characteristic absorption wavelengths or wavelength ranges corresponding to one or more of the intensity peaks of the incident light, and each having characteristic emission wavelengths or wavelength ranges corresponding to one or more of the preferred output wavelengths or wavelength ranges; determining a combination and proportions of the two or more biological components whose emissions in response to incident light, optionally combined in appropriate proportion with incident light, combine to produce light having combined spectral content having maximum intensities at the preferred output wavelengths or wavelength ranges. Given a sufficient repertoire of biological components having different absorption and emission characteristics, it is possible to produce emitted light having any arbitrary spectral content. In practice, the ability to do so will be limited by the availability of biological components having the necessary emission and absorption wavelengths; however, the characteristics of biological components can be made to better conform to desired characteristics by employing the forced adaptation methods and techniques as disclosed herein.

The schematic representations of FIGS. 24-26 may be used to illustrate the advantageous combination of components to engineer a desired spectral content. First, referring to FIG. 24, any biological component 200, such as, for example, an RC− light antenna structure, may be repeated many times so as to produce a desired intensity of its characteristic emitted wavelength or wavelength range in the emitted light 205. In another embodiment as illustrated schematically in FIG. 25, a non-biological photoactive component 212 receives the full spectrum of illuminating light 213. The biological component 215 receives the full spectrum of illuminating light 216 and emits light 217. The non-biological photoactive component is responsive to (or has heightened responsivity to) light in a range of wavelengths within the full spectrum of the illuminating light 213 as compared to other wavelengths, but is comparatively nonresponsive to (or less responsive to) light in another range of wavelengths within the full spectrum of the illuminating light 213. The biological component 215 is responsive to light within the range of wavelengths to which the non-biological component 212 is nonresponsive (or has low responsivity) and emits and illuminates the non-biological component with light 217 at wavelengths to which the non-biological component is responsive (or has comparatively higher responsivity). As a result the overall device of FIG. 25 acts as a photoactive device responsive to a wider spectral range than a device employing only the non-biological component 212 as the sole photoactive element, or a device as illustrated in FIG. 24 in which all incident light is absorbed and reemitted by the biological component.

In some embodiments, a plurality of biological components of differing characteristics may be employed in combination with the non-biological component 212 to employ even more regions of the spectrum to which the non-biological element 212 is not responsive or is less responsive, as schematically illustrated in FIG. 26. In an embodiment a device 220 includes a non-biological or engineered photoactive component 222, a first photoactive biological component 223 is responsive to light 224 in a first region of the spectrum to emit light 225 in a second region of the spectrum different from the first region of the spectrum by which it is illuminated. The second region of the spectrum includes wavelengths at which the non-biological component 222 responds photoactively or has heightened photoactive responsivity as compared to other wavelengths. A second photoactive biological component 227 is of a photoactive biological material different from the photoactive biological material of the component 223. In an embodiment of the device 220, the component 227 is responsive to light 228 in a third region of the spectrum to emit light 229 in a region of the spectrum different from the third region of the spectrum by which it is illuminated. The light 229 emitted by the second biological component 227 is in a region of the spectrum at which the non-biological component is photoactively responsive or has heightened photoactive responsivity. That may be the same as the second region of the spectrum at which light is emitted by the first biological component 223, or the light emitted by the second biological component 227 may be in a region of the spectrum overlapping or different from the spectrum of the light emanating from the first biological component 223. In this embodiment of the device 220, then, the device is photoactive, or has improved photoactivity, in the manner of the photoactive non-biological component 222, but at several regions of the spectrum at which the component 222 is not photoactively responsive or has lower than desired photoactive responsivity.

In a second embodiment of the device 220 of FIG. 26, the two photoactive biological components 223 and 227 may be active in the same or overlapping regions of the spectrum of the light illuminating them 224, 228, but may emit light in differing regions of the spectrum at which the non-biological component 222 is comparatively more highly photoactive to take advantage of a photoactivity profile of the material of the component 222 that has several peaks at several different wavelengths, that is has heightened responsivity at various different wavelengths. Additional biological components of characteristics different from the component 223 and 227 may also be employed with the non-biological component 222 so as to extend the range of wavelengths that are received and shifted by the biological components to activate the photoelectric or other properties of the non-biological component 222 or to provide further illumination of the photoactive element 222 in further regions of the spectrum where the particular photoactive material has heightened responsivity. Again encasement of the device 220 is possible as long as the biological components can be illuminated. This device too can be realized on the nanoscale or can be scaled up by the use of many of the active elements making up the biological components 223 and 227. Also, as with the devices 200 and 210 of the FIGS. 24 and 25, multiple devices 220 may be incorporated in a much larger overall device.

In embodiments as depicted in FIGS. 24, 25 and 26 the photoactive non-biological components 202, 212, 222 may be of any kind or modality, such as, for example, a photovoltaic cell wherein a voltage V is developed across the output electrode pairs 206 and 207, 218 and 219, or 230 and 231 in response to illumination of the non-biological component by light in the proper range of wavelengths. The fluorescent units making up the biological components 201, 215, 223 and 227 may be any combination or arrangement of such units derived from one or more of the organisms of Table A or in any other manner as disclosed herein.

In some embodiments, a biohybrid device includes a plurality of biological components that are or include light antenna structures, disposed in or on a substrate. The light antenna structures may be biologically derived as disclosed herein, and may include one or more RC– light antenna structures and/or force-adapted light antenna structures, or may include light antenna structures that are both RC– and force-adapted.

Figure 11:
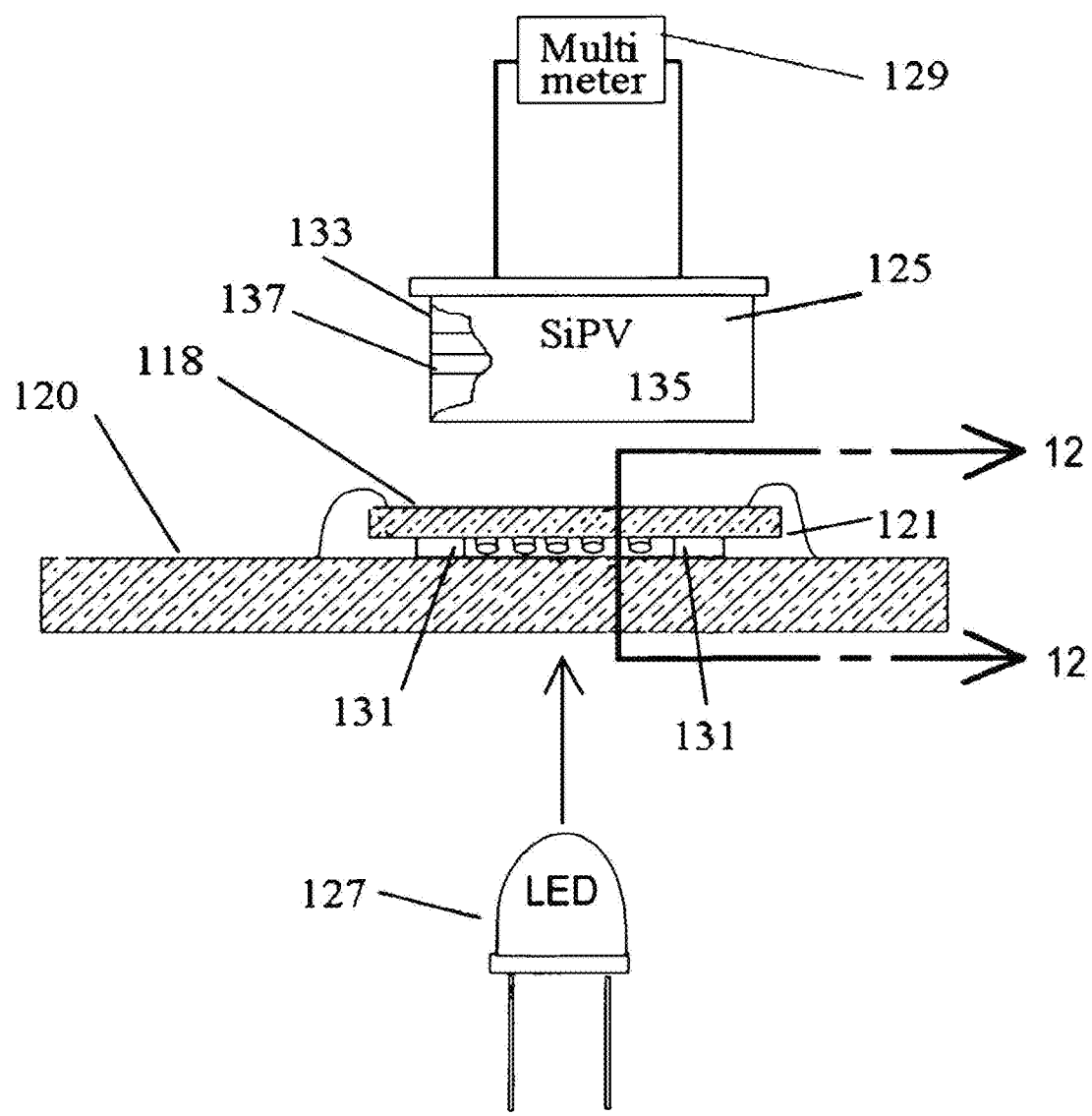
FIG. 11 is a diagrammatic illustration, partly in section, of a hybrid photovoltaic device in accordance with the disclosure hereof.
Figure 12:
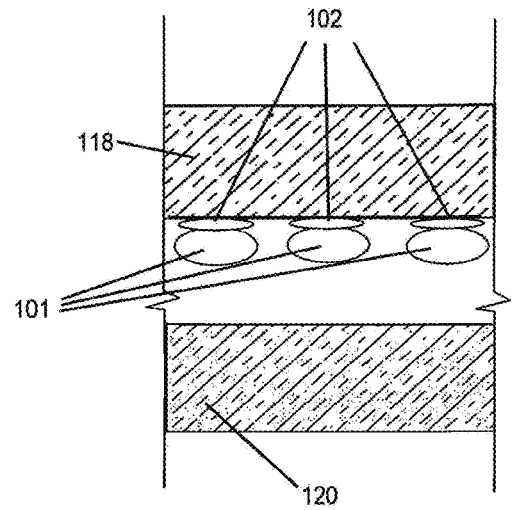
FIG. 12 is an enlarged fragmentary cross-sectional view along the line 12-12 of FIG. 11 and shows the chlorosomes like that of FIG. 6 adherent to a transparent plate.

In some embodiments, a biohybrid device may additionally include one or more photoactive non-biological components disposed in any manner such that light emitted by light antenna structure(s) is made to impinge upon a photosensitive region or component of the photoactive non-biological component. For example, as shown in FIGS. 11 and 12, a photosensitive non-biological component such as a photovoltaic cell 125 may be placed with its photosensitive region in the path of light emitted by one or more light antenna structures 101. In some embodiments, the light antenna structures may be disposed in an ordered array, such as, for example, in an orientation whereby their light-emitting moieties are predominantly oriented so as to emit light in a desired direction. In some embodiments, a plurality of light antenna structures are disposed in an orientation and/or position such that light emitted by at least one of the light antenna structures is preferentially oriented in the direction of the photosensitive region or component of a photoactive non-biological component. In some embodiments, the incident light includes light in the visible range.

In some embodiments of a biohybrid device including light antenna structures, the light antenna structures respond to incident light by emitting emitted light that differs in spectral content from the incident light, such as, for example, where light at a first wavelength is emitted by one or more of the light antenna structures in response to light incident thereon at a second wavelength different from the first wavelength. In some such embodiments, light emitted by one or more of the light antenna structures in response to light incident thereon is Stokes-shifted with respect to the incident light.

In some embodiments of a biohybrid device including light antenna structures, one or more of the light antenna structures is force-adapted. In some such embodiments, the force-adapted light antenna structures are extracted or derived from force-adapted organisms and/or progeny of such organisms, such as, for example, from populations of photosynthetic organisms that have been subjected to environmental conditions that produce an adaptation resulting in an improved performance of the biohybrid device. In some such embodiments, the force-adapted light antenna structures are extracted or derived from an expression system expressing a genetic sequence cloned or derived from force-adapted organisms. In some embodiments, the force-adaptation may relate to any characteristic affecting the performance of the light antenna structures in a biohybrid device, such as, for example, a force-adaptation producing an enhancement of the emission by a light antenna structure of at least one wavelength of light in response to at least one wavelength of incident light; a force-adaptation producing an increase in the pigment content of the light antenna structures and/or a change in the relative proportion of particular pigments; and/or a force-adaptation producing a change in the size of the light antenna structures.

In some embodiments of a biohybrid device, a substrate in or on which biological components such as light antenna structures are disposed may be a solid substrate, such as, for example, glass. A substrate may be or include an optically transmissive medium. In some embodiments biological components may be disposed in a gel, colloidal suspension, matrix, or liquid medium.

In some embodiments light energy is transmitted from a biological component such as a light antenna structure to a non-biological component by fluorescence resonant energy transfer (FRET). In some embodiments a biohybrid device includes a plurality of light antenna structures, at least one of which includes at least one FRET donor and responds to incident light by producing an excited state in the FRET donor.

In some embodiments of a biohybrid device including one or more RC– light antenna structures, at least one of the RC– light antenna structures is an RC– chlorosome. In some such embodiments, at least one RC– light antenna structure is isolated or extracted from a force-adapted organism exhibiting a forced adaptation affecting at least one characteristic of the light antenna structures produced by said organism. In some such embodiments, the at least one characteristic is a characteristic indicative of or affecting the response of the light antenna structures to light incident thereon.

In some embodiments of a biohybrid device including one or more light antenna structures, the light antenna structures are adsorbed in or on the substrate. In some such embodiments the light antenna structures are immobilized or positionally constrained in or on the substrate by electrostatic interactions, by van der Waals forces, by hydrophobic interactions, by hydrogen bonds, by physical entrapment, by chemical bonds, by affinity tags, by linkers, or in any other manner operable to constrain the light antenna structures as appropriate for an application of interest. In some embodiments, the light antenna structures are immobilized or positionally constrained with respect to a photoactive non-biological component.

In some embodiments of a biohybrid device including one or more RC– light antenna structures, the RC– light antenna structures are derived from light antenna structures of biological origin by removing therefrom a reaction center, and/or other matter not required for emission of Stokes-shifted light in response to incident light.

In some embodiments of a biohybrid device including one or more RC– light antenna structures the light antenna structures are synthetic equivalents or analogs of biologically derived light antenna structures.

In some embodiments a biohybrid device includes a photoactive non-biological component, which may be or include a photovoltaic component, a photoconductive component, a photoemissive component, a photodetector, photographic material, a charge coupled device, a photodiode, a photomultiplier, a pyroelectric photodetector, a photoactive chromophore, a phototransistor, a thermal detector, a complementary metal-oxide semiconductor (CMOS), a metal-semiconductor-metal photodetector, or any other device or material operable to produce a signal or change in any characteristic in response to light. In some embodiments a biohybrid device includes a photoactive non-biological component disposed to receive light emitted by the light antenna structures, and the light emitted by the light antenna structures corresponds more closely to the optimal response range of the photoactive non-biological component than does the light incident on the light antenna structures.

A method of making a biohybrid device according to the disclosure hereof may include disposing a plurality of light antenna structures, which may include one or more RC– light antenna structures and/or one or more force-adapted light antenna structures, in or on a substrate. The method may include disposing, in or on a substrate, light antenna structures that are isolated or extracted from organisms that have been force-adapted to alter at least one characteristic of the light antenna structures expressed by the organisms or from progeny of the organisms. A method may include disposing a photoactive non-biological component in the path of light emitted by said light antenna structures.

A method of making a biohybrid device according to the disclosure hereof may include: subjecting a population including a plurality of organisms to forced adaptation whereby at least one organism expresses adapted light antenna structures altered in at least one characteristic; propagating the adapted light antenna structures in an organism or expression system; isolating or extracting adapted light antenna structures from the organism or expression system; and disposing in or on a substrate a plurality of adapted light antenna structures isolated or extracted from the organism or expression system. In such a method, subjecting a population comprising a plurality of organisms to forced adaptation may include growing the population under environmental conditions resulting in at least one heritable change in at least one organism and selecting from the population a subpopulation that includes the at least one organism or its progeny. In a method of making a biohybrid device according to the disclosure hereof, propagating the adapted light antenna structures in an organism or expression system may include propagating the adapted light antenna structures in progeny of an organism manifesting the forced adaptation, and/or may include propagating the adapted light antenna structures in organisms expressing the adapted light antenna structure as a result of gene transfer or cloning from said at least one organism or its progeny, and/or may include propagating the adapted light antenna structures in a cell-free expression system.

A method of making a biohybrid device according to the disclosure hereof may include disposing a photoactive non-biological component in the path of light emitted by force-adapted light antenna structures disposed in or on a substrate. In a method of making a biohybrid device according to the disclosure hereof, force-adapted light antenna structures isolated or extracted from an organism or expression system may be treated to remove or deactivate reaction centers associated with the adapted light antenna structures.

A biohybrid device according to the disclosure hereof may include an apparatus made according to any of the methods disclosed herein. Any such apparatus may include a photoactive non-biological component, which may be a photodetector, disposed in the path of light emitted by one or more force-adapted light antenna structures.

A method of producing a biologically derived material and/or biological component according to the disclosure hereof may include producing a forced adaptation in an organism by: in a plurality of populations of the organism each including a plurality of individuals of the organism in an initial state, subjecting each population to a different value of at least one environmental variable; evaluating at least one characteristic of at least one biologically derived material and/or component obtained from at least one organism in each population; determining a relation relating the at least one environmental variable to the at least one characteristic; from that relation determining a value of the at least one environmental variable corresponding to a desired value of the at least one characteristic, where the desired value differs from the value of the at least one characteristic of the at least one biologically derived material and/or component obtained from the organism in its initial state; and growing a population of the organism subject to the at least one environmental variable at the value thereof so determined. Such a method may further include producing a biologically derived material and/or component from at least one organism manifesting the forced adaptation.

In a method of producing a biologically derived material and/or biological component including evaluating at least one characteristic of at least one biologically derived material and/or component obtained from at least one organism in a population, the at least one characteristic of at least one biologically derived material and/or component may be or include a measure of the performance of the biologically derived material and/or component in a hybrid device that includes the biologically derived material and/or component and a non-biological component. In a method of producing a biologically derived material and/or biological component, evaluating at least one characteristic of at least one biologically derived material and/or component obtained from at least one organism in a population may include determining a figure of merit relating to the characteristic. In a method of producing a biologically derived material and/or biological component including evaluating at least one characteristic of at least one biologically derived material and/or component obtained from at least one organism in a population, the at least one characteristic of at least one biologically derived material may be or include a characteristic of said biologically derived material other than the response of said biologically derived material to the at least one environmental variable.

In a method of producing a biologically derived material and/or biological component, a relation relating at least one environmental variable to at least one characteristic of at least one biologically derived material and/or component may be an objective function. In a method of producing a biologically derived material and/or biological component including determining a value of at least one environmental variable corresponding to a desired value of at least one characteristic of at least one biologically derived material and/or component obtained from at least one organism, an organism expressing or manifesting a forced adaptation may be obtained from a population of the organism grown subject to the at least one environmental variable at the value thereof so determined, may be progeny of at least one organism obtained from a population of said organism grown subject to the at least one environmental variable at the value thereof so determined, and/or may be an organism expressing a genetic sequence derived from at least one organism obtained from the population of said organism grown subject to the at least one environmental variable at the value thereof so determined.

In a method of producing a biologically derived material and/or biological component including producing a forced adaptation in an organism, the organism may be a prokaryote, a photosynthetic bacteria, *Chloroflexus aurantiacus*, or any other organism capable of being force-adapted to produce a biologically derived material and/or component of interest, which may include an RC– chlorosome and/or any other light antenna structure.

In some embodiments according to the disclosure hereof, a biologically derived material may include at least one light antenna structure, made by a method of forced adaptation, the method including determining a relation relating at least one environmental variable to at least one characteristic of the biologically derived material, from said relation determining a value of the at least one environmental variable corresponding to a desired value of the at least one characteristic, growing a population of the organism subject to the at least one environmental variable at the value thereof so determined, and producing a biologically derived material from an organism manifesting the forced adaptation.

In some embodiments of a biologically derived material and/or component made by a method of forced adaptation including determining a relation relating at least one environmental variable to at least one characteristic of the biologically derived material and/or component, the characteristic of at least one biologically derived material and/or component may include a measure of the performance of the biologically derived material in a hybrid device comprising the biologically derived material and/or component and a non-biological component. In some embodiments of a biologically derived material and/or component made by a method of forced adaptation including determining a relation relating at least one environmental variable to at least one characteristic of the biologically derived material and/or component, the at least one characteristic of the biologically derived material may be or include a figure of merit relating to such characteristic, and/or the relation relating the at least one environmental variable to the at least one characteristic may be or include an objective function.

In some embodiments of a biologically derived material and/or component made by a method of forced adaptation including determining a value of at least one environmental variable corresponding to a desired value of at least one characteristic of the biologically derived material, an organism manifesting the forced adaptation may be obtained from a population of the organism grown subject to the at least one environmental variable at the value thereof so determined, and/or may be progeny of at least one organism obtained from a population of said organism grown subject to the at least one environmental variable at the value thereof so determined, and/or may express a genetic sequence derived from at least one organism obtained from the population of said organism grown subject to the at least one environmental variable at the value thereof so determined.

In some embodiments of a biologically derived material and/or component made by a method of forced adaptation including determining a value of at least one environmental variable corresponding to a desired value of at least one characteristic of the biologically derived material, the at least one characteristic of the biologically derived material may be or include a characteristic of the biologically derived material other than the response of the biologically derived material to the at least one environmental variable.

In some embodiments of a biologically derived material and/or component made by a method of forced adaptation including determining a value of at least one environmental variable corresponding to a desired value of at least one characteristic of the biologically derived material, an organism manifesting the forced adaptation may be a prokaryote, a photosynthetic bacteria, *Chloroflexus aurantiacus*, or any other organism capable of being force-adapted to produce a biologically derived component of interest, which may include an RC− chlorosome and/or any other light antenna structure.

Figure 30:
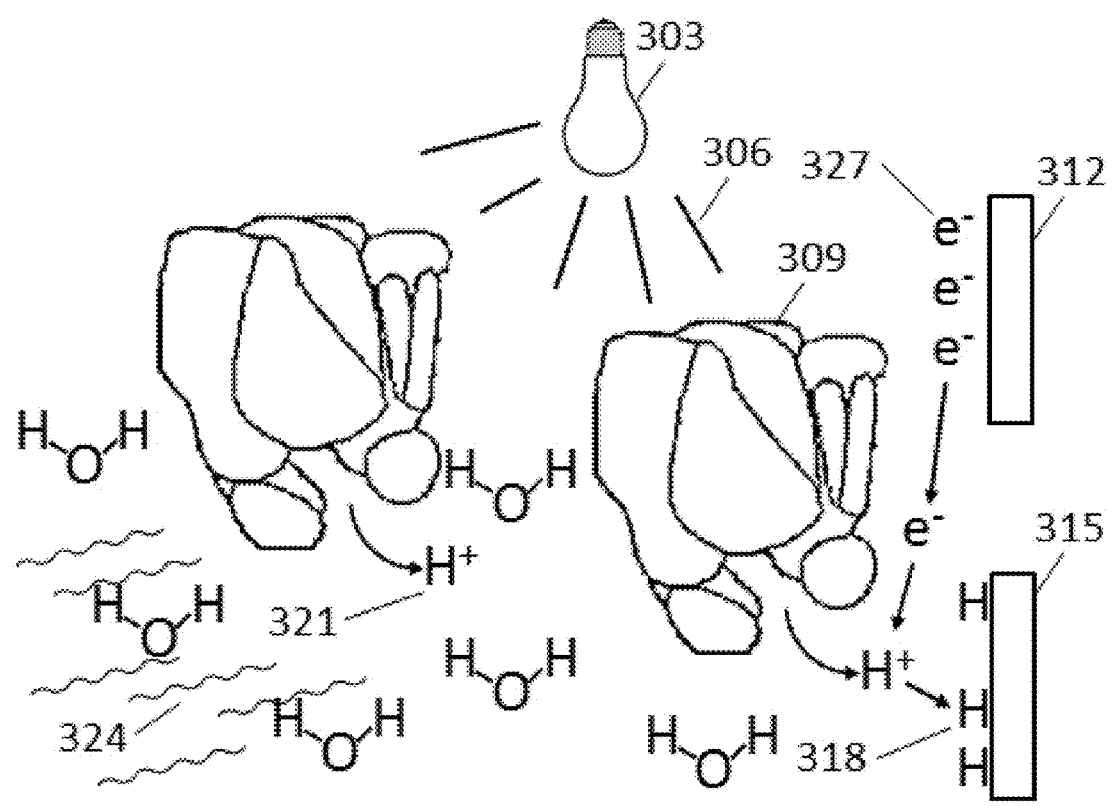
FIG. 30 is a schematic depiction of an embodiment of a device employing a biological component to produce hydrogen ions.

In embodiments, there is provided a device, as illustrated schematically in FIG. 30, wherein a plurality of biological components 309 such as, for example, light antenna structures, in association with photosynthetic reaction centers ("RC+"), as disclosed herein, are disposed in chemical and/or ionic communication with an aqueous solution 324. The biological components induce the production of H+ hydrogen ions 321 upon exposure to light 306, thereby lowering the pH of the aqueous solution. As used herein, chemical and/or ionic communication includes any arrangement or configuration wherein the light antenna structures and/or their associated moieties are accessible to dissociated or other elements or compounds, such as ions and/or water molecules in the solution, and H+ ions produced by the action of the light antenna structures and/or their associated moieties are generated into the solution. Optionally in embodiments, there is provided an electron source 312 in ionic communication with the aqueous solution which supplies electrons 327, resulting in the production of atomic or molecular hydrogen 318 upon combination of the electrons with the H+ ions. Optionally in embodiments, a hydrogen uptake component 315 is provided to extract, receive, transfer, and/or store the hydrogen produced. The biological components 309 may include any of the biological components disclosed herein operable to produce a lowering of pH upon exposure to light, such as, for example, the light antenna structures and associated moieties described in Example 13. In embodiments, a light source 303 may be provided, or light from a natural source such as the sun may be used. An electron source may include any device or component operable to supply electrons, such as, for example, a biohybrid photoactive device as disclosed herein. An uptake component may include any device, component, or material operable to extract, receive, transfer, and/or store hydrogen from an aqueous solution, including, for example, a high surface area material such as graphene. In embodiments, the components of the device may be assembled in any manner, dimensions, geometry, and relationships one to another deemed useful for an application of interest and operable to dispose the biological components for exposure to light and ionic communication with the aqueous solution. For example, in embodiments, the biological components may be disposed in colloidal or other forms of suspension in the aqueous solution, or constrained to a substrate in ionic communication with the aqueous solution. In embodiments, the device may be used in applications where it is desired to lower the pH of a solution, and/or for production and storage of hydrogen.

In embodiments, also provided is a method, including reducing the pH of an aqueous solution by exposing biological components in ionic communication therewith to light. In embodiments, a method may further include supplying electrons to reduce the H+ ions present in the solution. In embodiments, a method may further include extracting, receiving, transferring, and/or storing the atomic or molecular hydrogen produced thereby.

Example 1

A biohybrid device 12 was constructed as shown schematically in FIG. 12 by adsorbing RC− light antenna structures 101, 102 onto a glass coverslip 118, oriented with their light-emitting baseplates 102 toward the coverslip, and mounting the (inverted) glass coverslip onto a glass slide 120 having a raised ring on its surface (121, FIG. 11) to form a well.

RC− light antenna structures were prepared from chlorosomes obtained from the bacteria, *Chloroflexus aurantiacus* (*C. aurantiacus*), strain J-10-fl, American Type Culture Collection (ATCC, 10801 University Boulevard, Manassas, Va. 20110-2209 U.S.A) designation number 29366, deposited July, 1976.

Figure 3:
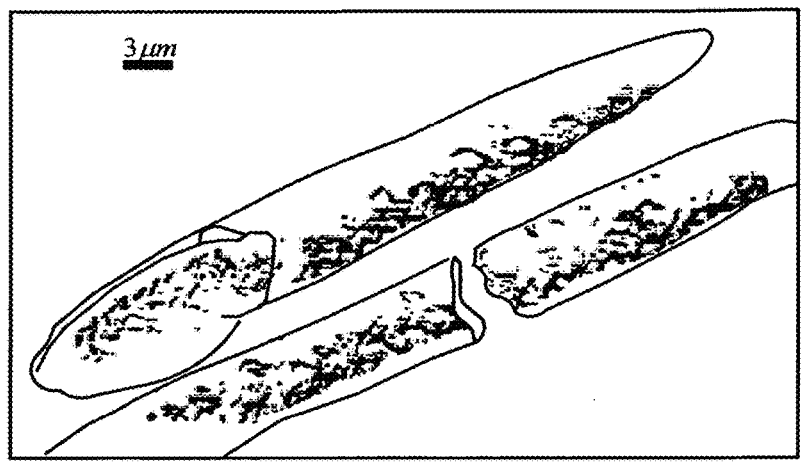
FIG. 3. is an image of *C. aurantiacus* by a scanning electron microscope.
Figure 4:
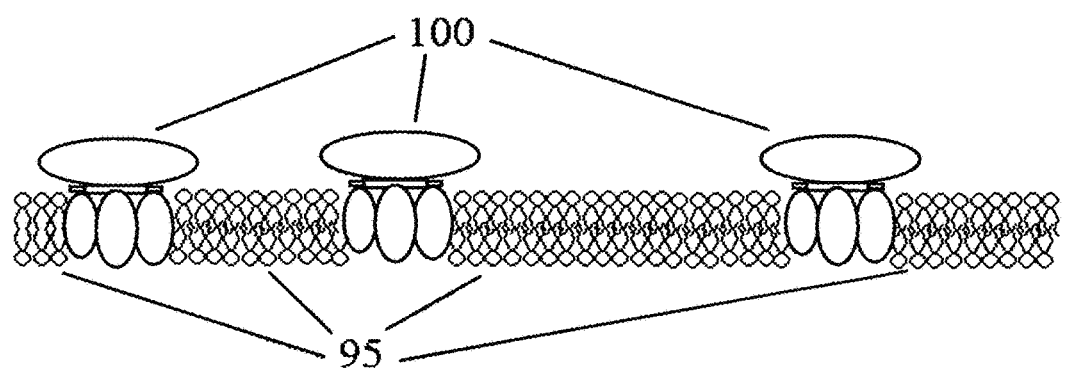
FIG. 4 is a cartoon schematic rendering of chlorosomes of *C. aurantiacus* in place in a cytoplasmic membrane.
Figure 5:
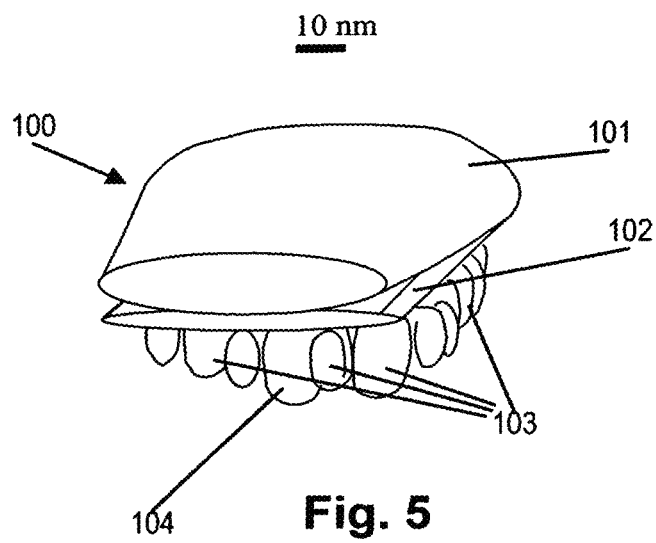
FIG. 5 is a diagrammatic (cartoon) illustration of a chlorosome of the bacterium *C. aurantiacus* with its four major subunits.

As currently understood and depicted schematically in FIGS. 4 and 5, chlorosomes 100 of the *C. aurantiacus* bacterium reside in cytoplasmic membrane, each chlorosome including two major supra-molecular pigment-protein subunits, the bacteriochlorophyll (Bchl) c 101, and the supra-molecular baseplate complex 102, which are associated with B808/866 supra-molecular complex 103 and reaction center (RC) 104. The B808/866 complex 103 contains 10-20 Bchl a molecules. The Bchl c sub-unit 101 is a lipid sack 101 containing bacteriochlorophyll (Bchl) c; as shown in FIG. 7, these are organized in units of approximately 10,000 molecules that form rod-like structures 115. (Inventors are not aware of any high resolution structures of *C. aurantiacus* chlorosomes. FIG. 3 shows a freeze fracture SEM image of *C. aurantiacus* in which small ovals, which are the cell's chlorosomes, can be resolved. The structural depiction shown in FIGS. 4-6 is due to Blankenship, et al.)

Figure 6:
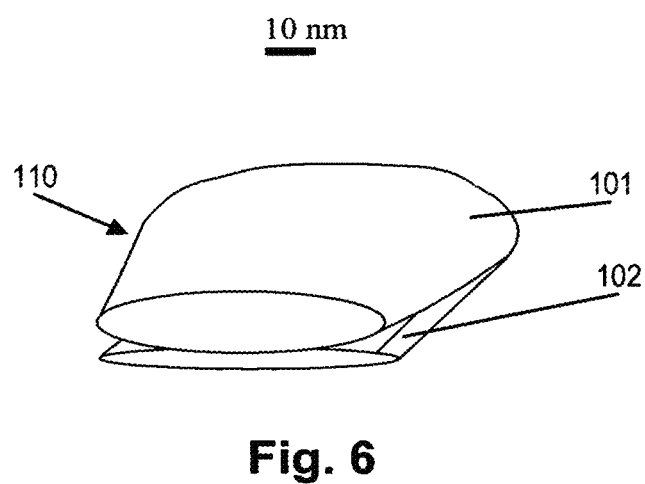
FIG. 6 is a diagrammatic (cartoon) illustration of the chlorosome of the bacterium *C. aurantiacus* of FIG. 5, but with two of its four subunits, the B808/866 protein light harvesting apparati and a reaction center removed.
Figure 7:
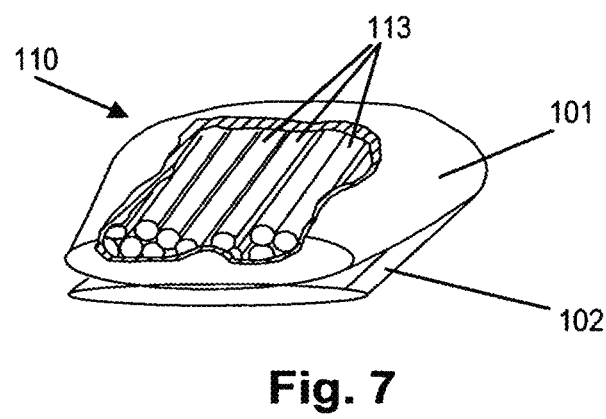
FIG. 7 is a diagrammatic (cartoon) illustration of the chlorosome of FIG. 6 with parts broken away for clarity showing contained rod-like structures of Bchl c.

The isolation procedure described below results in the removal of the B808/866 complexes 103 and the reaction centers, as well as other debris and material not contributing to the light absorption, Stokes shift, and re-emission, leaving RC− light antenna structures as depicted in FIG. 6, in which the subunits 101, 102 remain.

Figure 8:
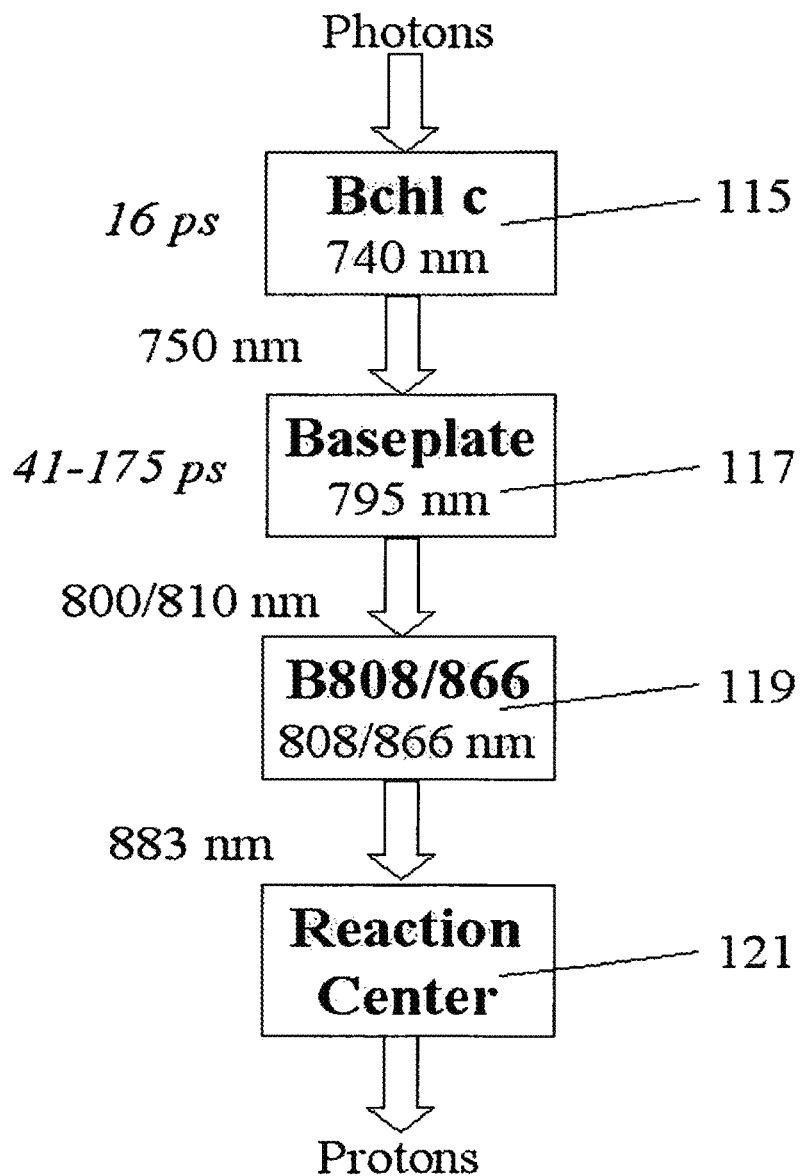
FIG. 8 is a functional block diagram in the form of a flow chart of optical interactions of the components of the chlorosome shown in FIG. 5.
Figure 9:
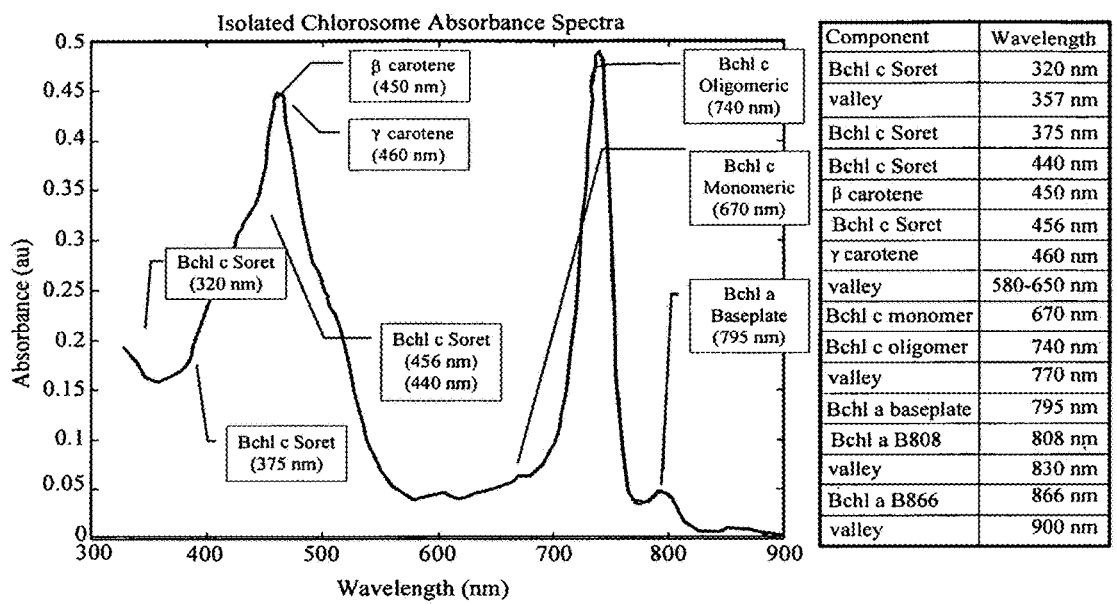
FIG. 9 is a plot of absorbance spectra data for a *C. aurantiacus* chlorosome.
Figure 10:
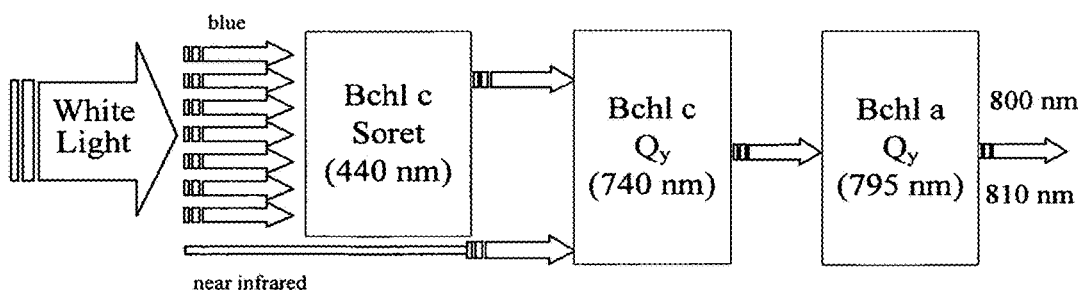
FIG. 10 is a diagrammatic block diagram in the form of a flow chart indicating the optical interaction of the parts of the chlorosome of FIG. 6.

In general, chlorosomes absorb visible and near infrared light, and deliver Stokes-shifted light to the reaction center. As depicted in FIG. 8, the molecules of the Bchl c subunit 115 transduce photonic energy associated with 740 to 750 nm light in approximately 16 ps with very little loss and pass photonic energy at 750 nm to the membrane of the baseplate 117. The baseplate comprises approximately 500 molecules of Bchl a, and transduces the photonic energy to 795 nm to 800/810 nm in 41-175 ps. The B808/866 complex 119 contains 10-20 Bchl a molecules, which absorb at 808 and 866 nm and transfer at 883 nm in approximately 250 ps to the reaction center (RC) 121. Finally, a special pair of Bchl a molecules of the reaction center converts the light energy into chemical energy to emit protons. FIG. 9 shows an absorbance spectrum of isolated chlorosomes in Tris buffer, and shows the absorbance peak at 740-750 nm attributable to the Bchl c rods and a peak at ~795 nm associated with the Bchl a baseplate. In addition absorption of light in the blue region by the cartenoids is evident and blue secondary absorbance peaks from the Bchl c and a (designated as Soret peaks) occur. As shown in FIG. 10, the Bchl c Soret absorbance peak corresponds to light at ~440 nm that is absorbed, transduced, and passed to the baseplate at ~795 nm.

*C. aurantiacus* cells were grown in 'D' media, under 6000 lux 50° C. in a one liter bottle. The 'D' mixture is as follows (all chemicals from Sigma): A mixture of 50.0 ml of the medium D stock is added to distilled water with 2.0 g Difco Yeast Extract, 1.0 g Glycylglycine (freebase) adjusting the pH to 8.2. This mixture is then autoclaved for 0.5 hr at 450° C. The medium D stock is prepared by mixing 40.0 ml of Nitch's Solution to 80.0 ml of the $FeCl_3$ solution in 3.5 l of distilled water with the following traces: 8.0 g Nitrilotriacetic acid, 4.8 g of$CaSO_4.2H_2O$, 8.0 g $MgSO_4.7H_2O$, 0.64 g NaCl, 8.24 g $KNO_3$, 55.12 g $NaNO_3$, and 8.88 g $Na_2HPO_4$. The Nitch's solution is made by placing 0.5 ml concentrated $H_2SO_4$, 2.28 g $MnSO_4$. $H_2O$, 0.5 g $ZnSO_4.7H_2O$, 0.50 g $H_3BO_3$, 0.025 g $CuSO_4.7H_2O$, 0.025 g $Na_2MoO_4.2H_2O$, and 0.045 g $CoCl_2.6H_2O$ into 1 liter of distilled water. This should be stored refrigerated. The $FeCl_3$ solution is prepared by adding 0.2905 g of $FeCl_3$ (or 0.4842 g $FeCl_3.6H_2O$) to 1 liter distilled water and should also be refrigerated.

RC− chlorosome isolation (Gerola, 1986) starts with cells concentrated (600 ml) by centrifugation at 3,600×g for 60 min. 2M NaSCN with 10 mM ascorbic acid in 10 mM Pi buffer (6.5 ml monobasic: 43.5 ml dibasic phosphate buffer per liter) was added to the weighed pellet in 4 ml/g amounts. Cells were homogenized 10× in a cell disruptor/homogenizer (Fisher Scientific). Disruption of cells was performed by (one) pass in a 4° C. stored French Press (ThermoSpectronic) cell with 20,000 psi. DNAse I (Sigma) was added and the solution was incubated for 30 min at room temperature. The solution was passed through the cell two more times.

Cell debris was removed by pelleting at 3,600×g for 1 hr. A continuous sucrose gradient was established by placing 2.0 ml of 40% sucrose in the NaSCN buffer in a tube and layering on 3.0 ml of a 10% sucrose solution. The tubes were placed, horizontally, into a dark, 5° C. storage until use (48 hrs later). The addition of 1.2 ml chlorosome solution to the top and ultracentifugation at 144,000×g for 18 hrs was started. Bands were collected by removal of the top band (by color), then removal by 1 ml at a time until the pellet was reached. The pellet was collected by addition of 1 ml to the tube and slight sonication to homogenize the pellet).

The device is shown schematically in FIG. 12. RC− chlorosomes were applied to a borosilicate coverglass (Fisher Scientific No. 12-541A) whose hydrophobicity was verified by contact angle goniometry (critical surface tension ~12 dynes/cm, a surface tension of 32 dynes/cm, and a contact angle (for DI water) of 41°). 20 µl of sample, at various dilutions in Tris buffer determined as described in Example 2, was applied to a hydrophobic coverglass and incubated in a laminar flow hood, in the dark, for at least 10 minutes. This gives the chlorosomes (or controls) enough time to physically adsorb onto the borosilicate glass surface. As shown in FIGS. 11 and 12, the exposed bases 102 of the chlorosomes 110, being hydrophobic, adhere to the surface of the plate 118.

As illustrated schematically in FIG. 11, the coverglass 118 was inverted and placed on top of a fluorescent microwell slide (Fisher Scientific No. 12-568-20), centered on the frosted ring (1 cm in diameter). The frosted ring was just sufficiently high above the surface of the slide 120 that a drop of the liquid suspension containing the chlorosomes was retained. The cover glass 118 was rested on the ring 131 and when the suspending liquid had evaporated leaving the chlorosomes adherent to the hydrophobic borosilicate cover glass surface as shown, an epoxy seal 121 was applied using a 2-part (optical grade) epoxy. The samples were then placed in a microslide holder and stored overnight (at least 24 hours) in the dark at room temperature. Further storage should be done at 5° C. in the dark. (An alternative procedure may be employed, wherein evaporation under vacuum is performed overnight and then the sample is sealed onto a fluorescent microwell slide; however, the method disclosed above is preferred since it ensures a hydrated sample and diffusion of the chlorosomes onto the glass surface.) Use of the Fisher microwell slides, which have two frosted rings/ wells, facilitates testing since one of the wells may be provided with suspending liquid only, or with RC+ chlorosomes or non-force-adapted chlorosomes, so as to provide a control.

Example 2

Devices according to Example 1 were prepared wherein the percent coverage of chlorosomes of the well surface was predetermined at several distinct values. Percent coverage was determined by estimating chlorosomes counts in the volume of solution applied to the well based on chlorosomes counts in calibrated volumes at known dilutions, and determining the surface coverage assuming adsorption in a single layer based on the measured average size of the chlorosomes. RC− chlorosome sizes were estimated by atomic force microscopy imaging, by transmission electron microscopy, by dynamic light scattering, and by field emission scanning electron microscopy (FESEM), using the methods described below. Estimated sizes are shown in Table F; estimated hydrodynamic radii ranged from 15.53 nm to 19.54 nm, varying according to the growth conditions applied to the organisms from which the chlorosomes were extracted. Chlorosome counts at various dilutions are shown in Table G.

TABLE F

Calculated chlorosomes dimensions due to growth conditions.

| Hydrodynamic radius | Intensity (lux) | Length (nm) | Width (nm) | Height (nm) |
|---|---|---|---|---|
| 15.53 | 100-6,000 | 100 | 30 | 10 |
| 15.33 | 2,000 | 98.66 | 29.60 | 9.87 |
| 18.11 | 4,000 | 116.55 | 34.96 | 11.65 |
| 19.54 | 6,000 | 125.75 | 37.72 | 12.57 |

TABLE G

Chlorosome counts by dilution.

| Dilution Surface | Count/$\mu m^2$ | Count/ml |
|---|---|---|
| 1:1 | — | $9.06 \times 10^{11}$ |
| 1:50 | 9.0 | $1.81 \times 10^{10}$ |
| 1:100 | 4.8 | $9.66 \times 10^9$ |
| 1:1000 | .57 | $1.15 \times 10^9$ |
| 1:10000 | .041 | $8.25 \times 10^7$ |

Atomic Force Microscopy (AFM) was performed by evaporating a 100 µl sample of chlorosomes (overnight in desiccant jar) onto a standard borosilicate coverglass. A Digital Instruments' Nanoscope III Multimode AFM was used in Tapping Mode (TMAFM) to image the chlorosomes at various dilutions. The dilutions' absorbance spectra were taken prior to imaging. Prior to running the AFM experiments, a known liquid volume (400 µl) was taken from solution containing RC– chlorosomes in DI water previously characterized via absorbance spectra (ABS 0.01 @740 nm) and was evaporated onto a clean, optically clear glass disk with known surface area (113.1 mm). The disks were made hydrophobic to enhance RC– attachment and orientation due to theoretical studies performed by using a molecular modeling algorithm (Chou, 1977) that suggested that the baseplate region attached to the reaction center may be hydrophobic in nature. Tapping mode AFM experiments were conducted utilizing a small scan head (D head) to scan 1 $\mu m^2$ surface areas on both the control disks (no RC– chlorosomes deposited) and test disks (RC– chlorosomes deposited).

Transmission Electron Microscopy (TEM) was performed by taking isolated chlorosomes and evaporating a 0.5 µl drop onto a bacitracin treated Formvar coated grid (300 mesh). Negative stains of uranyl acetate were used to enhance the images. Images were taken at the Life Science EM Facility at 25,000× magnification. Images were saved in jpeg format, inserted into MATLAB and data (size and counts) were taken. Calculations were then scaled to predict how many chlorosomes were in a 1 ml sample for each of three dilutions. Absorbance spectroscopy of these dilutions was also performed to correlate absorbance spectra to count for the given population using a Beckman DU-65 photo spectrometer.

Dynamic light scattering was performed by injecting 20.0 µl of each sample via a gas-tight syringe into the quartz cuvette and readings were taken at 2 acq/sec. Data filtering was performed to minimize dust events but capture the quickly diffusing small particles. The Dynamics V6 software developed the autocorrelation curves and produced the polydisperse plots of Rh versus % mass for each sample.

Field Emission Scanning Electron Microscopy (FESEM) was performed at the Center for Solid State Electronics Research Center at Arizona State University on a Hitachi 4700 FESEM. A hemocytometer technique was employed as an initial method that could be correlated to the others. Another technique used computer aided image processing to allow the chlorosomes surface to be assigned a '1' or 'white' pixel value and the background a '0' or 'black'. Accounting for surface area (number of pixels) per chlorosome, histograms were made and counts were calculated via computer. The final technique was a modified ASTM method in which the surface is traversed from left to right, and top to bottom, counting chlorosomes until 100 is reached. Then the number of pictures required to reach 100 chlorosomes and the surface area of each picture were accounted for and a final count of chlorosomes/ml was calculated. Here, five concentrations (plus a distilled water control) were imaged using all three techniques and counts were correlated to ABS spectra. Stubs were prepared by evaporating 100 µl of the dilution onto a hydrophobic borosilicate glass disk, attaching the disk to a stub via tape and carbon coating the samples for a period of 10 minutes. The chlorosomes were diluted with Tris buffer at pH 8.0 and 10 mM NaCl, by addition of 0.788 g Trizma HCl into 500 ml of DI water, under constant stirring. Meanwhile, 0.605 g of Trizma Base was added into 500 ml of DI water under constant stirring. Both solutions were mixed together and 0.9 g NaCl was added while mixture was stirred thus making 1 liter of 10 mM Trizma buffer, pH 8.0 with 20 mM NaCl.

In the AFM and FESEM studies, the images were taken and saved in jpeg format for processing in MATLAB as was done in the TEM images. Size was verified but in these techniques, counting was the main objective. The same process of taking the counts in an area and re-calculating the count per ml was performed on many dilutions to enable a more accurate count (and correlation to absorbance data).

Example 3

Light absorption and emission properties of the chlorosomes were measured and characterized using a Beckman DU-65 photospectrometer (for absorbance or percent transmittance). Dilutions were made to obtain a measurable sample and 1 ml sample was placed into a polystyrene (UV) micro-cuvette for absorbance or percent transmittance spectral readings. Sample blanks of pure buffer were used to subtract out potential spectral interference from buffers. Buffer spectra were gathered as well in case of major interference in results. Emission spectra were gathered by either (full spectra) a PTI spectrofluorometer, or a modified detector/filter device in a Shimadzu RF-1501 spectrofluorometer. In all instruments, 1.0 ml volumes in micro-cuvettes were used. Plots of data were then analyzed by use of MATLAB software and plotting programs. This testing was performed in order to assess quality control by comparing spectral data (on absorbance) and relative output (emission). Samples were also studied under laser scanning confocal microscopy (instrument from LEICA) to investigate orientation, and function (stability) was observed by absorbance spectroscopy of the sample afterwards.

Ranges of dilutions were made by serial dilution of the stock chlorosome sample. Each dilution was placed into a standard cuvette (using a blank of Tris buffer) and full (400-900 nm) absorbance readings were gathered (via an RS232C port) onto computer and analyzed and plotted in MATLAB. At this point, selection of a non-pigment wavelength (650 nm in the case of the chlorosomes) was made to use in correlating absorbance to the previous counts made on each dilution and then plotted. This wavelength was selected for its non-photosynthetic (non-optically active) properties and consistent nature between different growth conditions during the counting experiments. Hence, a calibration curve was made between counting and absorbance for a series of dilutions of chlorosomes.

Figure 18:
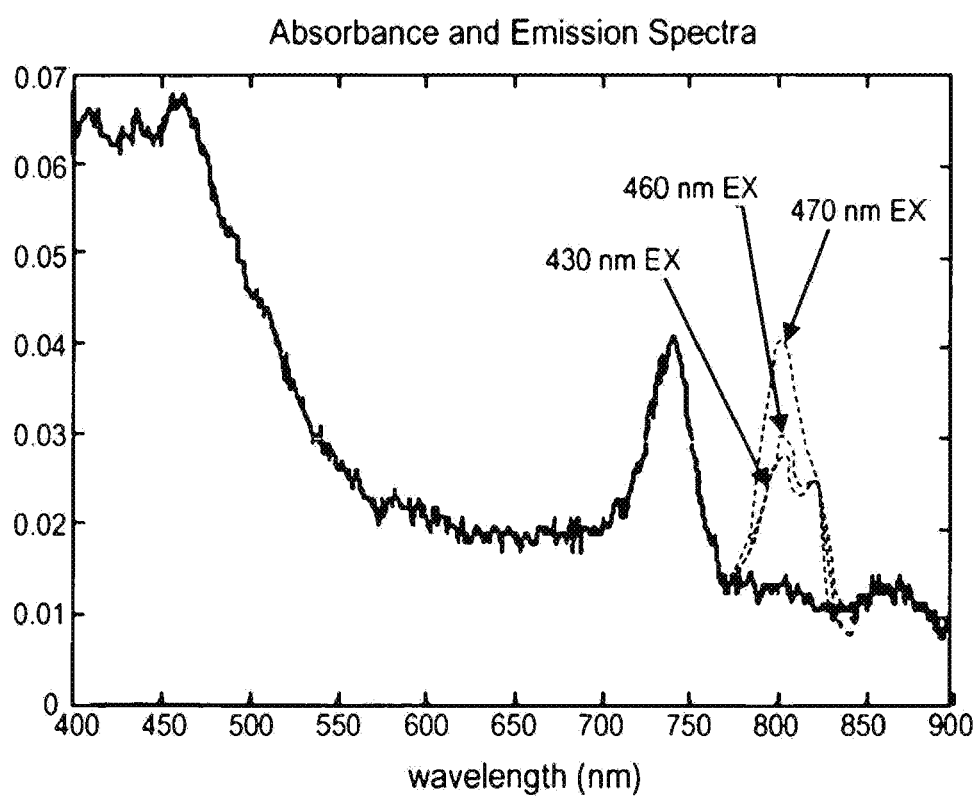
FIG. 18 is a plot of absorbance and emission spectra of chlorosomes of *C. aurantiacus*.

As shown in FIG. 18, when excited with 430 nm, 460 nm and 470 nm, which is exactly where the silicon photovoltaic cells is less sensitive, the RC− chlorosomes emit at about 810 nm where the silicon photovoltaic cell is sensitive. In FIG. 18, the peaks indicated as "430 nm EX", "460 nm EX", and "470 nm EX" correspond, respectively, to the emission spectra produced in response to excitation at 430 nm, 460 nm, and 470 nm. There is, therefore, a spectral enhancement by the addition of the biological component that is similar to that shown generally in FIG. 18.

Example 4

Devices (shown in cross section in FIG. 12) fabricated as described in Example 1 were evaluated by measuring the response of a photovoltaic cell 125 in a device as shown schematically in FIG. 11, wherein a microwell slide was interposed between a light source and the light-sensitive surface of the photovoltaic cell, and comparing results for slide wells having RC− chlorosomes applied with identical control wells having no chlorosomes applied or having RC+ chlorosomes applied.

As shown in FIG. 11, on or closely spaced above the coverglass plate 118 a commercially available silicon photovoltaic cell (Edmond Optics NTS3-371) was supported. Illumination of the chlorosomes and the photovoltaic cell 125 by an LED 127 produced a voltage across the output of the photovoltaic cell 125 as can be observed by a multi meter 129. The RC chlorosomes and the light receiving surface of the photovoltaic cells were no more than a millimeter apart. The construction of the off-the-shelf photovoltaic cell placed the light receiving surface 133 of the silicon semiconductor in a metal housing or can 135, to be exposed through a glass closure 137. Characteristics of an exemplary device 12 are shown in Table H.

TABLE H

Device characteristics

| | |
|---|---|
| Size: | 10 × 30 × 10 nm |
| Approx Rh: | 33 nm (calculated), 41 nm (DLS) |
| Energy Transfer: | |
| Stokes Shift: | 470-800/810 nm |
| Δλ | 320 nm |
| QE | 69-92% QE |
| Delay Time: | 50 ps-1 ns |
| Orientation Control: | Yes |
| Number of particles: | $4 \times 10^7$ -$8 \times 10^9$ chlorosomes |
| Number of molecules: | $4 \times 10^{15}$-$8 \times 10^{17}$ |

In an exemplary device as shown schematically in FIG. 11, the components were interfaced (mechanically) by a self-built optical chamber made from acrylic sheet. The microslide 120 port was milled into one piece, and holes were drilled for a fiber optic bundle (not shown) and the SiPV detector 125. Accessory ports/chambers (not shown) were made to fit 25 mm filters such as additive (or subtractive) and NDF for wavelength and intensity control, respectively. The whole apparatus was black felted to reduce external light leakage. Power was supplied using a standard variable power supply (for the LED) and the SiPV was monitored utilizing a digital multimeter (DMM).

In this arrangement, device parameters such as maximum output, time-response (or rise time), spectral sensitivity, intensity sensitivity, temperature sensitivity, and device lifetime were tested. Maximum output was monitored by allowing the device sufficient time to go from 0 millivolts to maximum for that particular LED intensity. The difference was recorded and compared to when no sample is introduced. This ratio was defined as normalized relative output. Response time is defined as the time required going from 0 to 90% of the final value during a switching on stage.

This was performed by timing a device versus the standard SiPV detector (no device attached). Spectral sensitivity was performed by replacing the LED with various colored LED's that covered the visible spectrum as well as into the near infrared (NIR). Voltages were recorded, and normalized relative outputs were made on the final device. All devices were tested using 470 nm, 735 nm, 880 nm, and white LED's (full spectra). Intensity sensitivity was verified using the blue (470 nm) LED since this was the wavelength of choice for enhancement. The devices (ranging from low to high percent coverages) were tested under LED illumination and ratios of output voltages were made versus the same detector under the same illumination with no chlorosomes present as a control. The percent enhancement signifies ratio of the measured output of the hybrid well device to that of the control configuration. The rise time (the time it takes to get from 10% to 90% final voltage) was also measured and compared between the hybrid well devices to the stand-alone detector. This was accomplished with a stopwatch and DMM. White light LED (visible light) stimulation of a series of percent coverages were conducted and compared to monochromatic results.

Figure 29:
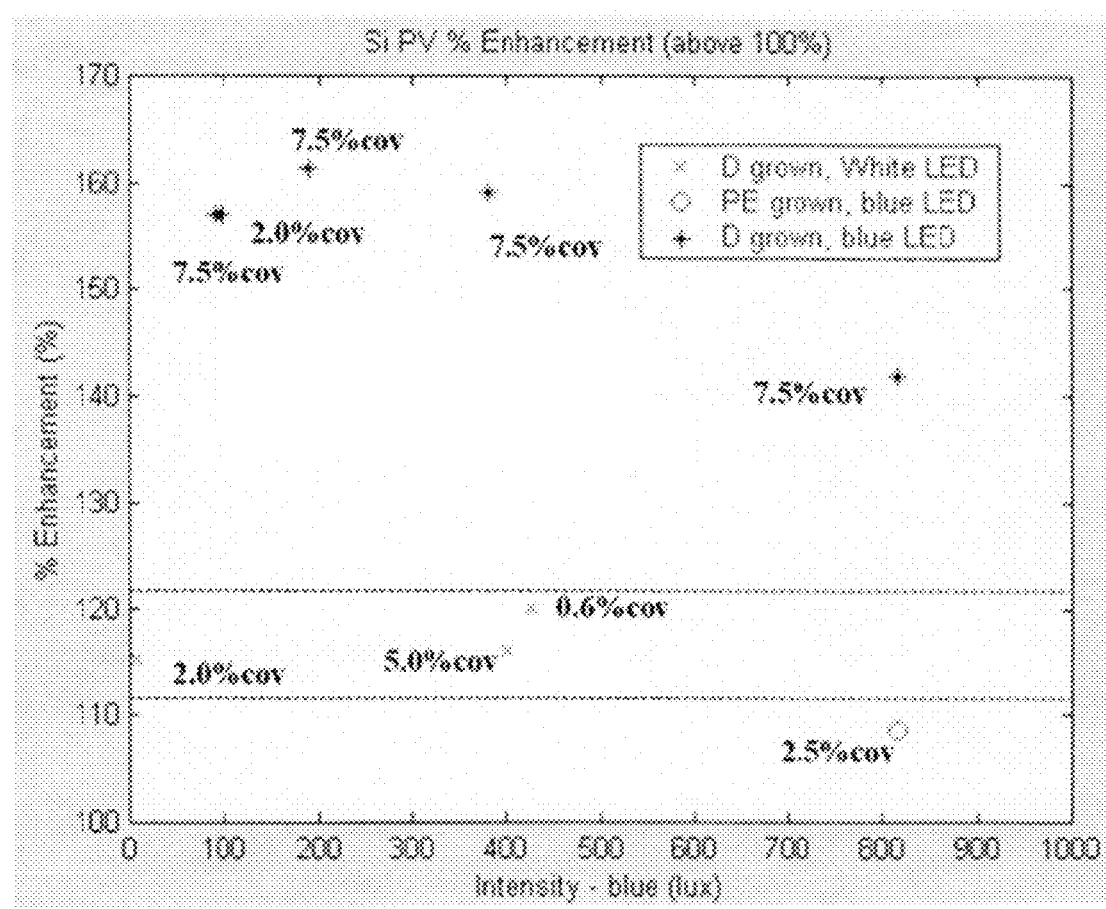
FIG. 29 is a graph indicating the percent enhancement of a photovoltaic device obtained using various biohybrid devices according to the disclosure hereof at various light intensities.

By way of example, an embodiment of the device according to Example 1, using white light (at 34.5% blue) at 1600 lux (approximately 552 lux blue) resulted in a 120% enhancement. As shown in FIG. 29, other devices fabricated as described in Example 1 produced percent enhancements ranging as high as approximately 160%, with results depending on the percent coverage, intensity of the LED illumination, the environmental conditions under which the organisms from which the chlorosomes were extracted were grown, and other factors.

Example 5

Experiments were conducted demonstrating that the relative abundance of pigment proteins in chlorosome-derived light antenna structures can be altered by force-adaptation under selected growth conditions of temperature, light intensity, and media volume (a measure of food abundance), and that these factors do not necessarily act independently in producing the adaptive response. From a population of *C. aurantiacus* 27 identical subpopulations were obtained and grown under specified values of three environmental conditions: temperature, light intensity, and media volume. Three values of each condition were tested as shown in Table J.

TABLE J

Low, Centerpoint, and High Factor Levels for DOE Experiment

| Factor | Low (−) | Center | High (+) |
|---|---|---|---|
| A = Temp | 36° C. | 48° C. | 60° C. |
| B = Intensity | 50 lumen | 270 lumen | 490 lumen |
| C = Media | 5 ml | 7.5 ml | 10 l |

Figure 22:
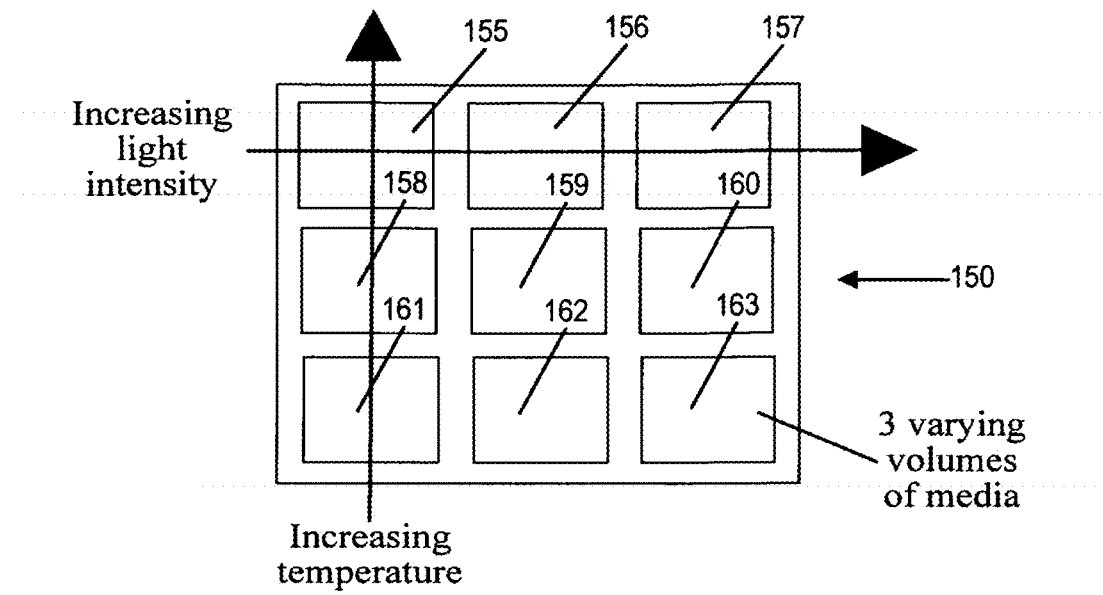
FIG. 22 is a diagrammatic illustration of a multiple input, multiple output environmental chamber having nine individual compartments.
Figure 23:
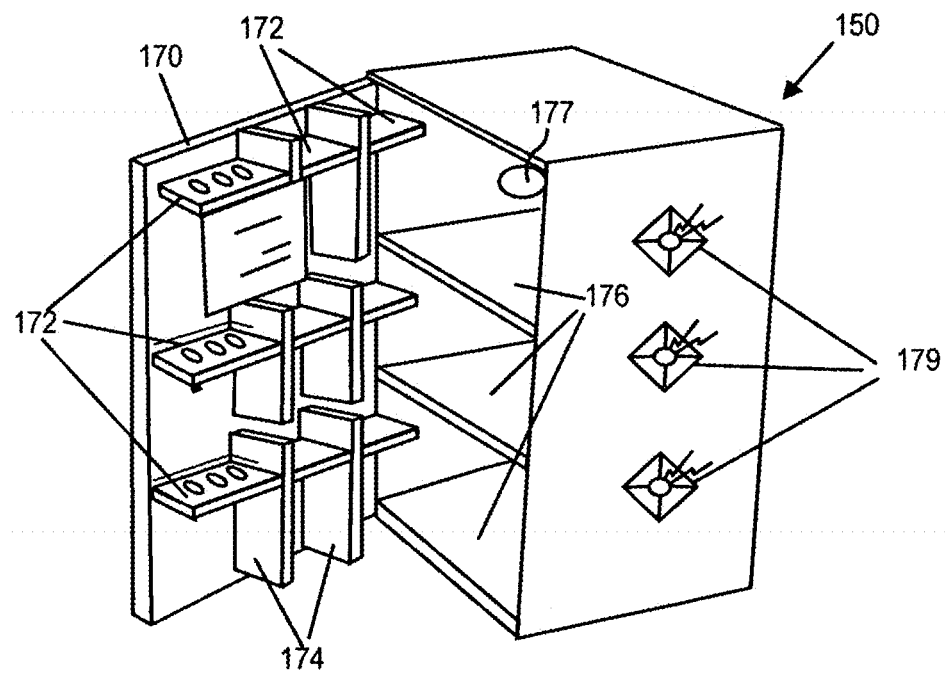
FIG. 23 is a perspective view of an environmental chamber like that diagrammatically illustrated in FIG. 22.

A multiple input, multiple output environmental chamber 150 (MIMO/EC) was constructed as diagrammed in FIGS. 22 and 23. Nine compartments 155 through 163 were provided. On its door 170 multiple shelves 172 are supported and have openings to retain culture containing test tubes or containers. Vertical dividers 174 separate the compartments 155-163. Horizontal dividers 176 separate the compartments vertically. Light bulbs, one of which is shown at 177 provide illumination. A series of fans 179 regulate temperature. Light intensity increased from left to right across the three columns of compartments and temperature increased from bottom to top across the three rows of compartments. Within the compartments three differing volumes of media were contained. Consequently, 27 combinations of variables were able to be tested. Ordinarily in biology research is conducted by the "OFAT" (one factor at a time) method. Here, the DOE approach permitted the three factors to be tested simultaneously at three levels with three replicates and an additional three centerpoints.

The original population from which the subpopulations were obtained was grown under the centerpoint conditions (48° C., 270 lumen, 7.5 ml, see Table J) for 14 days. The subpopulations were then grown under the specified combinations of environmental conditions and samples were extracted and evaluated from each at predetermined intervals as shown in Table K. Evaluation consisted of measuring the ratios of absorbance by the chlorosomes at 740 nm versus 808 nm ($R_1$), and 740 nm versus 866 nm ($R_2$). These ratios provide a measure of the relative abundance of bacteriochlorophyll (Bchl) c, which has an absorption peak at ~740 nm, and the B808/866 complexes, which absorb at 808 and 866 nm.

Representative results are shown in Table K. The "condition" in Table K refers to the three environmental conditions (temperature, light intensity, and media volume, respectively), with "+" corresponding to the high values shown in Table J, "−" corresponding to the low values, and "0" corresponding to the centerpoint values.

The force-adapted changes in absorption ratios are readily seen in Table K; for example, the "+−−" subpopulation (high temperature, low intensity, low media volume) at first appears to have greatly reduced absorption ratios as compared to the centerpoint ("000"), but after the second transfer has adapted to the changed conditions and produces quite high ratios. In the first two transfers, the culture appeared to be dying, but by the third transfer, cells have adapted to the different environment and grown.

The factorial design was chosen to quantify the relative importance of interaction between light intensity, temperature, and volume of media. The approach used was Design of Experiments (DOE). This method allows for data to be gathered in a way to avoid error by establishing an experiment protocol and quantifying error in a mathematical way. The regression method that was used was the analysis of variance (ANOVA) technique. This tool (DOE) allows for data to be gathered at normal conditions (centerpoint) and at extremes (above and below the centerpoint). Analysis is based on quantifying effect and probability of effect of a factor or interaction on the output variable. The relationship between the environmental condition variables and the $R_1$ and $R_2$ ratios was analyzed by ANOVA with the results shown in Tables L and M. Interaction between factors was determined from the ANOVA as well as the interaction graphs provided by the software.

TABLE K

DOE experiment calculated data for pigment-protein growth/development ratios over a period of 6 transfers (3 weeks approximately).

| Condition | Ratio | Nov. 18, 1997 | Nov. 21, 1997 | Nov. 25, 1997 | Nov. 28, 1997 | Dec. 2, 1997 | Dec. 9, 1997 |
|---|---|---|---|---|---|---|---|
| −−− | 740/808 | 1.3182 | 1.2 | 1.1111 | 1.2174 | 1.25 | 1.0526 |
|  | 740/866 | 1.45 | 1.3333 | 1.1111 | 1.4 | 2 | 1.3333 |
| −−+ | 740/808 | 1.2381 | 1.1071 | 1.16 | 1.28 | 1.2308 | 1.1667 |
|  | 740/866 | 1.3929 | 1.1273 | 1.2889 | 1.4545 | 1.4545 | 1.25 |
| −+− | 740/808 | 1.1579 | 1.0345 | 0.9231 | 1.1842 | 1.0526 | 1.017 |
|  | 740/866 | 1.2571 | 1.0526 | 0.8571 | 1.2857 | 1.0909 | 1.3 |
| −++ | 740/808 | 1.2353 | 1.375 | 1.2027 | 1.1667 | 1.2 | 1.4 |
|  | 740/866 | 1.377 | 1.5068 | 1.3692 | 1.3462 | 1.3548 | 1.4848 |
| +−− | 740/808 | 1.3333 | 1.2222 | 2.0732 | 2.1458 | 1.88 | 1.125 |
|  | 740/866 | 1.4545 | 1.375 | 2.2667 | 2.4235 | 2.0435 | 1.1538 |
| +−+ | 740/808 | 1.6 | 1 | 1 | 2.3368 | 1.7412 | 1.9759 |
|  | 740/866 | 2 | 1 | 1 | 2.6118 | 1.9221 | 2.2162 |
| ++− | 740/808 | 1.2857 | 1.0952 | 1.1579 | 1.2917 | 1.2687 | 1.25 |
|  | 740/866 | 1.4062 | 1.2778 | 1.2941 | 1.4531 | 1.4167 | 1.3514 |
| +++ | 740/808 | 1.1111 | 1 | 1 | 1.3049 | 1.2273 | 1.3929 |
|  | 740/866 | 1.3333 | 1 | 1 | 1.4079 | 1.35 | 1.56 |
| 000 | 740/808 | 1.7105 | 1.7901 | 1.7901 | 1.5854 | 1.686 | 1.5224 |
|  | 740/866 | 1.8571 | 1.9079 | 1.9595 | 1.6667 | 1.7262 | 1.619 |

TABLE L

ANOVA Table for $R_1$. Note DF represents degrees of freedom and CE is coefficient estimate. An appropriate prob > |t| cutoff was chosen to be 0.01 for this output variable; therefore A, B, C, and AC have an effect on this output.

| Factor | CE | DF | Error | Prob > |t| |
|---|---|---|---|---|
| Intercept | 1.23 | 1 | $9.913 \times 10^{-3}$ |  |
| A-Temperature | −.032 | 1 | $9.913 \times 10^{-3}$ | .0041 |
| B-Light Intensity | −.037 | 1 | $9.913 \times 10^{-3}$ | .0013 |
| C-% Volume | −.044 | 1 | $9.913 \times 10^{-3}$ | .0003 |
| AB | .027 | 1 | $9.913 \times 10^{-3}$ | .0118 |
| AC | −.056 | 1 | $9.913 \times 10^{-3}$ | <.0001 |
| BC | .015 | 1 | $9.913 \times 10^{-3}$ | .1372 |
| ABC | −.021 | 1 | $9.913 \times 10^{-3}$ | .0502 |
| Centerpoint | .41 | 1 | .024 | <.0001 |

TABLE M

ANOVA Table for R2 ratio. Note DF represents degrees of freedom. An appropriate prob > |t| cutoff was chosen to be 0.1 for this output variable therefore A, B, C, and AC have an effect on this output.

| Factor | Coefficient Estimate | DF | Error | Prob > |t| |
|---|---|---|---|---|
| Intercept | 1.23 | 1 | .047 |  |
| A-Temperature | −.11 | 1 | .047 | .0321 |
| B-Light Intensity | .032 | 1 | .047 | .5080 |

TABLE M-continued

ANOVA Table for R2 ratio. Note DF represents degrees of freedom. An appropriate prob > |t| cutoff was chosen to be 0.1 for this output variable therefore A, B, C, and AC have an effect on this output.

| Factor | Coefficient Estimate | DF | Error | Prob > |t| |
|---|---|---|---|---|
| C-% Volume | .006 | 1 | .047 | .8990 |
| AB | .049 | 1 | .047 | .3050 |
| AC | −.035 | 1 | .047 | .4651 |
| BC | −.036 | 1 | .047 | .4516 |
| ABC | −.077 | 1 | .047 | .1181 |
| Centerpoint | .51 | 1 | .11 | .0002 |

Figure 13A:
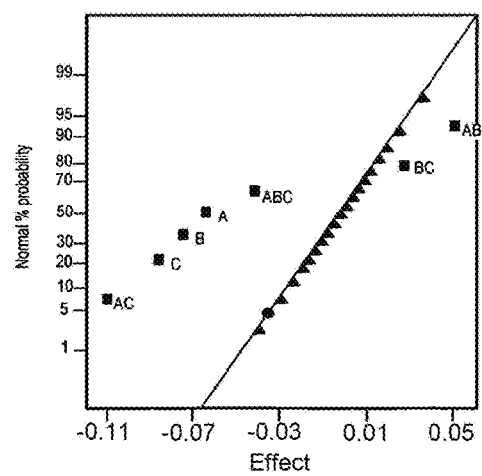
FIG. 13$a$ is a normal percentage probability plot and FIG. 13$b$ is the interaction plot between temperature and percent volume for a design of experiments analysis where the output variable to be studied was the ratio $R_1$ of absorbance at 740 nm to absorbance at 808 nm.
Figure 13B:
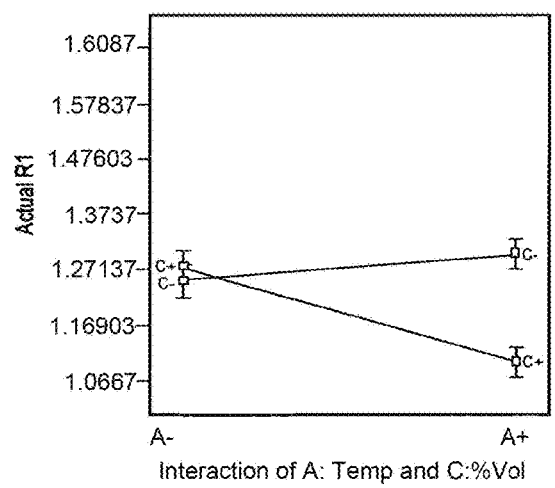
Figure 14A:
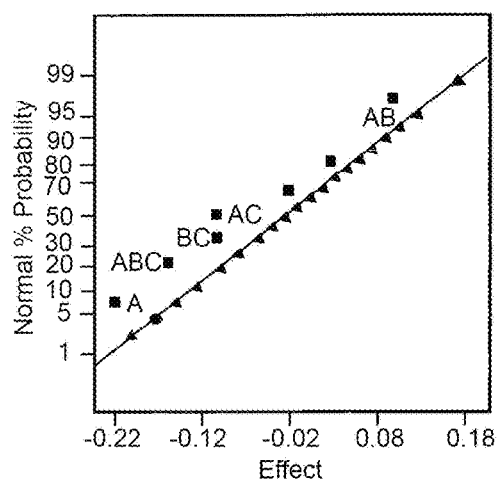
FIG. 14$a$ is the normal percent probability plot and FIG. 14$b$ the interaction plot between temperature and percent volume media to air for a design of experiments analysis where the output variable studied is the ratio $R_2$ of absorbance at 740 nm to absorbance at 366 nm.
Figure 14B:
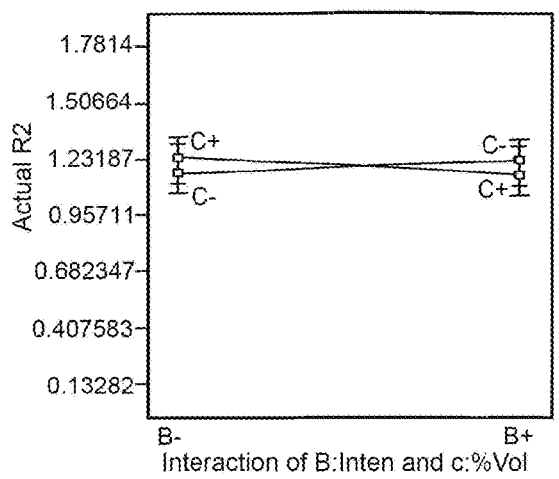

The $R_1$ ratio showed a strong dependence on each individual factor and on the interaction between Temperature and % Volume. All other interactions were insignificant when compared to these four factors/interactions. This can be seen in the ANOVA analysis shown in Table L. The normal % probability plot and interaction plot (between Temp and % Vol) can be found in FIGS. 13a and 13b. As FIG. 13b shows, changes in % volume correspond to a large change in $R_1$ ratio at high temperature, and negligible change at low temperature, demonstrating the non-independence of these inputs. The $R_2$ ratio showed strong effects due to only temperature. All other factors and interactions were insignificant when compared to temperature (see Table M). The normal % probability plot and interaction plot (between Temp and % Vol) can be found in FIGS. 13a and 13b. As shown in FIG. 14a, the results are so close to the linear line that they are deemed insignificant except for temperature. Even the interaction plots (FIG. 14b) showed slight interactions (lines cross but the error bars overlap). The highest level possible for the $R_2$ ratio would be with bacteria grown under low temperature.

It is interesting to note from the results that the response variables ($R_1$ and $R_2$) are not dependent upon the same factors. $R_1$ is sensitive to temperature, light intensity, and % volume, and the interaction of temperature and % volume. However, the $R_2$ ratio is dependent upon only the temperature during growth. This ratio was long believed to be only dependent upon light intensity but temperature was found more significant in these experiments. This may be due to the fact that the real dependent output is the $R_1$ ratio. If the bacteria are grown under those conditions and $R_1$ changes, $R_2$ must change as well but not vice-versa.

It is also possible that the temperature affects only the 866 nm molecules and light never changes growth (within limits selected in this study). Another, stronger argument is that the natural funnel-like energy transfer in the chlorosome (from 740 to 795 to 808 to 866 nm molecules) protects the molecules further down the chain (like the 866 Bchl a) from being sensitive to factors such as light. At the same time, these molecules are still protein based and very dependent upon temperature effects.

Example 6

Biohybrid devices were fabricated according to the procedures described in Examples 1 and 4, utilizing RC− light antenna structures obtained from *C. aurantiacus* that were force-adapted according to the disclosure hereof to produce enhanced device performance. MIMO/EC experiments were performed as described in Example 5, wherein light intensity during growth, temperature during growth, and growth time (days) were chosen as the conditions to be varied (see FIG. 20). Given the desired purpose of the forced adaptation, which was to optimize the percent enhancement of the response of a photovoltaic cell to white light having a substantial blue content, a figure of merit was devised relating predicted device performance to the ratio of absorbance by the light antenna structures at 740 nm to that at 460 nm (each adjusted by subtracting 688 nm absorbance). The rationale for this figure of merit is that 740 nm absorbance provides a measure of the abundance of Bchl c, which participates directly in the light funneling/Stokes shifting process, relative to that of carotenoids, which absorb at 460 nm and detract from the light funneling/Stokes shift on account of quenching. The figure of merit expression used (calibrated from experimental results) was:

$$\text{FoM} = 3.4469 \times ((\text{Abs740 nm} - \text{Abs688})/(\text{Abs460 nm} - \text{Abs688 nm})) - 0.8361$$

(Because cellular membrane components have an absorbance of 650-700 nm, the concentration of cells in each sample can be determined from the absorbance data in this region. By normalizing the data, it is possible to extrapolate the Bchl c absorbance for individual cells.)

Based on MIMO/EC experiments, an objective function was fitted from which FoM could be predicted from temperature (T), intensity (L), and growth days (G):

$$\text{FoM} = 0.84 - 0.0001306 \cdot L - 0.001923 \cdot T - 0.054 \cdot G + 0.000004446 \cdot L \cdot T + 0.00001575 \cdot L \cdot G + 0.001108 \cdot T \cdot G - 0.0000007194 \cdot T \cdot L \cdot G$$

Figure 20:
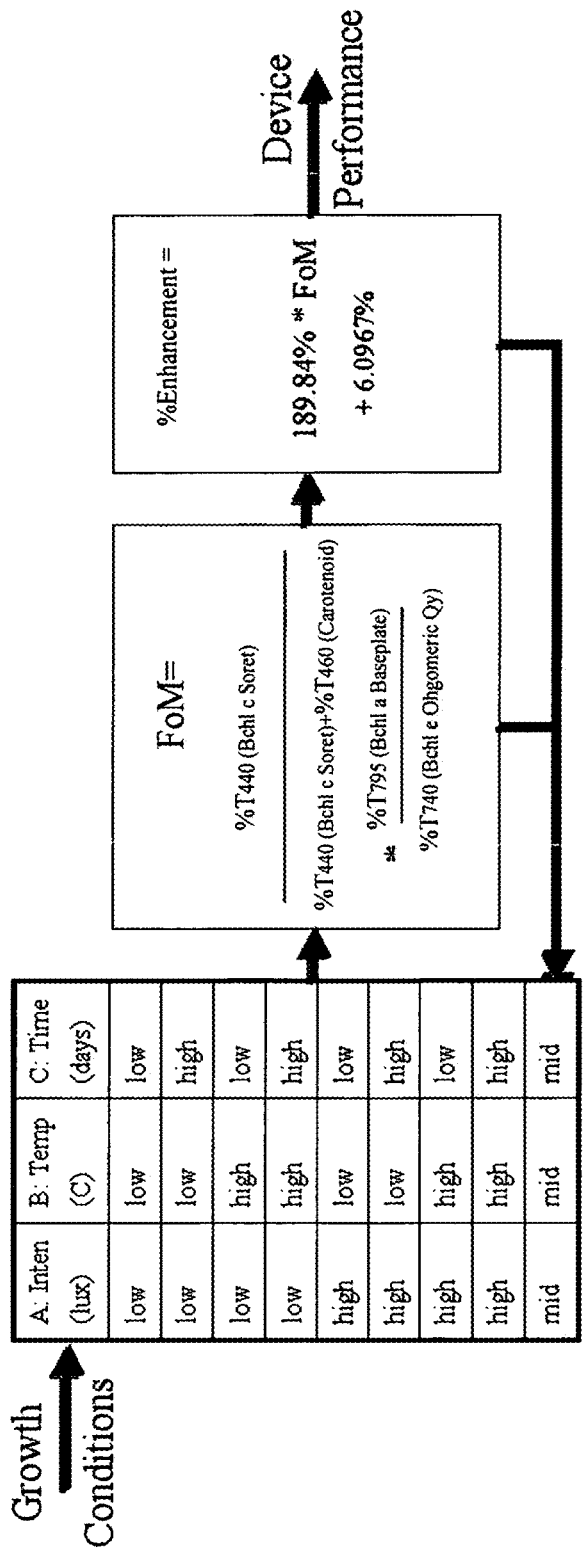
FIG. 20 is a functional block diagram that illustrates the use of a figure of merit in the development of a biological hybrid device with feedback from the Figure of Merit determination through a DOE or the like development program and feedback from the device performance.

For example, this function predicts a FoM of 0.82 for growth at 55 C under light at 50 lux for 14 days; this was the highest FoM found obtainable under the experimental conditions used. An expression was obtained relating the figure of merit to percent enhancement of the device, as shown in FIG. 20, as follows:

$$\text{Pct Enhancement} = 189.84 \cdot \text{FoM} + 6.0967$$

According to the foregoing expression, an FoM of 0.82 predicts percent enhancement of the device of 161.8%, which is very close to the actual maximum device enhancement obtained.

Table N shows figure of merit values for several representative force-adapted light antenna structures as determined from the absorbance ratios indicated, and the corresponding device percent enhancement.

TABLE N

Selected hybrid device characteristics. Ratio R is ratio of absorbances (740 nm-688 nm)/(460-699 nm). FoM is light antenna structure figure of merit. Hybrid device performance is ratio of device output (V) to device output under same light conditions without light antenna structures.

| CFX Test System | Chlorosome count | % Surf. Cover (Chlorosomes) | Light Intensity (Blue Led) [lux] | R | FoM | Hybrid Device Perf. |
|---|---|---|---|---|---|---|
| Hybrid Device #10 | 5.23 × 10⁸ | 2.0 | 98 | 0.4735 | 0.795 | 1.571 |

TABLE N-continued

Selected hybrid device characteristics. Ratio R is ratio of absorbances (740 nm-688 nm)/(460-699 nm). FoM is light antenna structure figure of merit. Hybrid device performance is ratio of device output (V) to device output under same light conditions without light antenna structures.

| CFX Test System | Chlorosome count | % Surf. Cover (Chlorosomes) | Light Intensity (Blue Led) [lux] | R | FoM | Hybrid Device Perf. |
|---|---|---|---|---|---|---|
| Hybrid Device # 23 | $6.54 \times 10^8$ | 2.5 | 100 | 0.3824 | 0.482 | 0.976 |
| Hybrid Device # 24 | $1.308 \times 10^9$ | 5.0 | 400 | 0.3977 | 0.5347 | 1.076 |
| Hybrid Device # 28 | $1.963 \times 10^9$ | 7.5 | 190 | 0.4808 | 0.8210 | 1.614 |

Example 7

In force-adapting organisms and/or components and in performing experiments to determine optimal environmental conditions for doing so, selection of suitable ranges of environmental values depends in part upon the susceptibility of the organisms and/or components to degradation, instability, inconsistency, or loss of function under extreme or damaging conditions. In particular, inconsistent results initially plagued experiments leading to the development of the hybrid device. As noted, C. aurantiacus is self-adapting. This meant that chlorosomes taken from the same growth of cells could not necessarily be relied upon to behave consistently. It was in part to overcome this lack of consistency that force-adapted C. aurantiacus were produced having the performance desired. Because of the number of environmental variables involved in the growth of the cells and their substituent chlorosomes, a design of experiment (DoE) technique was employed to arrive at chlorosomes that performed well and consistently. Thus, another useful application of the force-adaptation methods, apparatus, compositions, and concepts disclosed herein is in engineering light antenna structures for improved stability and consistency.

Choice of the ranges of environmental condition values used in the previous examples and in other force-adaptation and MIMO/EC experiments were informed by performing a number of experiments to measure the effect of particular values on stability, degradation, and consistency. In this example the techniques used for doing so are disclosed. It will be apparent to persons of skill in the art that such experiments may readily be modified for use with other organisms and/or biological components.

Isolated chlorosomes were first tested for stability in storage under two conditions. A 'fresh' sample was maintained for use in 7° C. freezer and a long-term (or later called 'frozen') sample was placed in liquid nitrogen (LN2). Initial degradation was noted in the samples and could be clearly seen (at the monomeric 670 nm absorbance peak) in the absorbance spectra of the 'fresh' sample. Emission spectra were even gathered to determine whether a decrease in emission occurred.

A series of experiments were designed and run with chlorosomes, with and without reaction centers, in solution, to test for intensity-related photodegradation. Samples were diluted to 1:100 of the original stock into Tris buffer. 2 ml each were separated out for 6 different light conditions. Concentrations were matched between all samples using absorbance readings. Light intensity was varied by the use of filters, light with no filter, or no light, such that percent transmissions were 0% T, 14% T, 36% T, 53% T, 68% T, and 100% T and measured (photometrically). The light source was a standard 100-watt white light bulb. Degradation was quantified by noting a percent decrease in the 740 nm absorbance. The samples were continuously illuminated and at specific time intervals, absorbance readings were taken. Degradation of the 740 Bchl c $Q_y$ band was measured by (1) peak height from start to finish and by (2) integration of the area under the $Q_y$ band. Times were marked when 5, 10, and 15% degradation of the peak were attained. A control sample (buffer) was also held under the same illumination and used as the blank in the photospectrometer.

Experiments were performed to relate intensity-induced photo-degradation to concentration. Various concentrations of chlorosomes (in 2 ml) were degraded by a similar white light (at fixed intensity). From these sets of experiments minimum photostress terms were calculated to determine a 0% degradation intensity (and time). Again, the 740 nm peak height provided a measure (by absorbance spectra) of photo degradation over time.

Another mode of destruction of the photo-stability of the chlorosomes could be simple denaturation (by acidity) by the buffer. Therefore, buffers (with a varying pH) were made from pH 2.0 to 12.0 and 1 ml of each was added to 1 ml of a chlorosome stock solution. Absorbance spectra as well as $R_h$ (hydrodynamic radius) were measured for each sample. The $R_h$ was measured by testing 20 Ill of the sample in the DLS system.

Heat (or temperature) induced photodegradation or denaturation was also explored and tested. Starting at room temperature, a water bath holding a vial of chlorosomes was brought to near boiling over a period of hours. During the experiment, absorbance readings were taken at about every 5-10° C. and degradation was calculated as mentioned previously.

Another mode of destruction of photo-stability was tested by increasing the concentration of the chlorosomes in solution to determine whether concentration aggregation could be attained. This was accomplished by use of concentration filters and measured by $R_h$. 15 ml of sample was concentrated down to differing volumes and the filtrate (buffer) was removed leaving a more concentrated sample. Then 20 µl of sample was removed for DLS measurements after absorbance spectra were taken to ensure viable sample and perform chlorosome counting.

An experiment to evaluate another mode of destruction of photo-stability entailed the addition of a competitor for absorbance of blue light. Carotenoid solutions from the isolation procedure were reintroduced into the chlorosome sample (by dilution) and emission measurements were taken. Side control experiments were performed by addition of buffer alone. Stimulation was applied using the RF-1501 Shimadzu spectrofluorometer and emission was measured on a photodiode after passage through an 800 nm interference filter (so that scatter and excitation energies could be removed). This also allowed for ratios of the Bchl c to a, Soret, and carotenoid peak to be calculated and compared for potential enhancement calculations for the hybrid well experiments.

Stability was verified by absorbance spectroscopy (400-900 nm) and degradation was recorded. Temperature of operation was also investigated and degradation was also monitored so that an operational range of temperatures could be established. In these experiments, data was also obtained to establish device lifetimes under such 'operational' conditions. The lifetime was determined by determining the conditions leading to device degradation and the time required to reach that point.

Other tests included data gathered from solution effect studies only. Temperature effects were determined by the previous experiment in which the chlorosomes' photostability to temperature changes was determined. Being in a bulk system in a water bath controlled environment fitted the design parameters of the hybrid well experiments and throughout testing, no experiments were conducted outside the 25-100° C. range. A series of hybrid devices were constructed and tested (positively) over a large period of time (and intensities). Further experimentation was conducted on these samples throughout the research endeavor until no (positive) responses were seen. Afterwards, the absorbance spectra of a few high percent coverages were measured using a home-built slide holder in the DU-65 Beckman Photo spectrometer in order to check the status (photostability) of the chlorosomes.

Example 8

In performing experiments of the kind described in foregoing examples, it is important to control and hold constant various factors that, if allowed to vary, might introduce error. A number of the important factors are listed in Table P. Production of force-adapted light antenna structures from photosynthetic organisms potentially affects growth of the bacteria, and may cause alteration of the chlorosomes, which can be induced by the growth period factors such as, for example, intensity of light source, light type and wavelength (incandescent, LED, fluorescent); media (pH, temperature, components or strength); number of days allowed for growth (before isolation or media exchange); bottle-fill volume; and temperature. Some of these factors directly influence important design characteristics such as figure of merit (FoM), chlorosome size, and photostability, and may have indirect effects such as by altering the function and/or relative abundance of quenchers.

TABLE P

Factors influencing performance of biohybrid device.

| Growth | Isolation | Sample Fab | Sample Run |
|---|---|---|---|
| Intensity | Procedure | Fab conditions Temperature Incubation time Light ON/OFF laminar hood | Light Source type LED Light bulb W/wout F.O. |
| Media | Buffer Type Molarity | Buffer Type Molarity | Light Intensity $V_{applied}$ NDF used |

TABLE P-continued

Factors influencing performance of biohybrid device.

| Growth | Isolation | Sample Fab | Sample Run |
|---|---|---|---|
| pH | Ionic Strength pH Temperature Aggregated? | Ionic Strength pH Temperature Sealing method | Measure tech. Stim. Time Light wavelength $V_{applied}$ LED |
| Light type Incandescent LED Fluorescent | Type (RC±) | Post fab storage Temperature Dark # days | Holder Sample holder LED + NDF SiPV + LPF |
| Days of growth Bottle Volume Temperature | Purity | % coverage Volume Droplet placed On coverslip In Well | Intensity control Detector DMM used 9 V (new) High Imped. |
| Wavelength | | Coverslip hydrophobicity | Orientation Facing SiPV Facing LED |
| | | Concentration | Red LPF used Voltage Applied NDF used Room lights ON/OFF Stimulation time |

Processing of the chlorosome requires isolation of the chlorosomes from the whole cell walls. This is done using a procedure well-documented in the literature although certain factors do arise in the process. There are different procedures used to isolate chlorosomes without the reaction centers (RC−) versus those with (RC+). The solvents, agents, and buffer types used in the procedure are also very important and factors such as (the type, molarity, ionic strength, pH, and strength) all come into play. These factors will affect the state of aggregation and purity (and successful use) of the isolated chlorosomes.

Manufacture of the chlorosome layer is the step where (in the foregoing examples), by means of immobilization by physical adsorption, a monolayer (or percent thereof) is deposited onto the surface of a substrate (here, borosilicate glass). Important factors for successful devices include: the fabrication conditions (temperature, incubation time, light ON/OFF, assembly in the laminar flow hood); sealing method; concentration, volume, and % coverage (and hence interparticle distances); droplet placement (on the coverslip or in the well); and coverslip hydrophobicity, all of which relate to chlorosome orientation (facing SiPV or LED).

FIG. 1 is a conceptual block diagram that indicates the design and development of a hybrid device of the nature of the enhanced photovoltaic cell described above. At each stage of development multiple variables entered the design process. This is tabulated, as well, in Table 2. From this it will be seen that a robust program such as the design of experiments program that permits the assessment of multiple variables and their interaction is an enabling design tool in arriving at a final product that meets the objectives of high performance, robustness, scalability, energy interactivity and adaptability.

In the case of the enhanced hybrid photovoltaic device many pertinent issues arise at each stage of design. At the product stage, the device needs to be tested using an appropriate light source and wavelength, such as a 470 nm LED or an incandescent light bulb with a correct interference filter yielding 470 nm wavelength. Intensity is a variable. The use of suitable light waveguides or fiber optics may be a variable to consider. Stimulation time must be taken into account since it and intensity will correlate to a certain photostress that the device will be able to handle or not handle if irreversible damage is to be avoided. Controlled environments and appropriate measurement devices are to be chosen.

Example 9

Based on the chlorosome functioning as conceptually diagrammed in the block diagram of FIG. 21a, the following improved Figure of Merit was devised.

$$FoM = \frac{\%T_{440(Bchl\ c\ Soret)}}{\%T_{440(Bchl\ c\ Soret)} + \%T_{460(Carotenoid)}} * \frac{\%T_{795(Bchl\ a\ Baseplate)}}{\%T_{740(Bchl\ c\ Oligomeric\ Qy)}}.$$

This FoM takes into account the total transmittance of the Bchl c Soret at 440 nm as compared to the total Soret and carotenoid 460 nm transmittance and the baseplate Bchl a transmittance at 795 nm as compared to the Bchl c oligomeric transmission at 740 nm. Engineering to a figure of merit in an exemplary embodiment of the biohybrid device of Examples 1 and 5 was calculated to yield 160% of the $V_{out}$ response of the original silicon photovoltaic cell at a figure of merit of 1.0. The actual improved output was measured at 157%.

Example 10

The DOE approach used involves seven steps in order to perform the experiment. The first step involves defining the problem statement. Here it was desired to determine which factors could increase the pigment protein content of the chlorosomes. Next, the factors that might be expected to influence pigment protein content had to be chosen. Levels and/or ranges of these factors were then established. The next step is to identify the output variable(s) to be studied. Since the change in pigment protein content was desired to be analyzed, ratios of relevant absorbances were chosen. Once the choice of factors and levels was made, a $2^3$ factorial approach was chosen, using three replicates and five centerpoints. Experiments were run at the end of a three day growth period and data was gathered. Since replicates were used the data analysis did not include determination normal % distribution plot and the analysis was based on the ANOVA tables.

Example 11

Figure 15A:
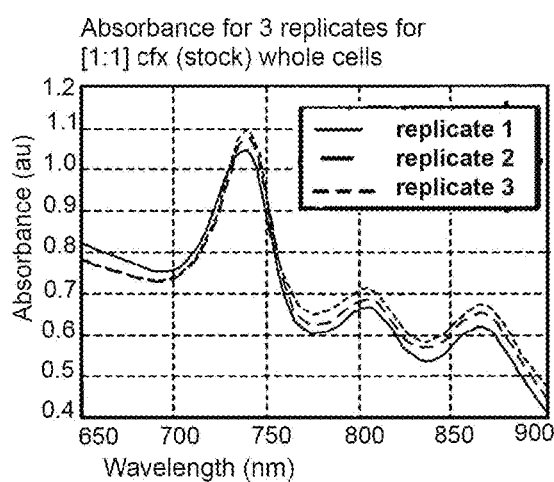
FIG. 15a is a plot of three replicates of a full spectra of *C. aurantiacus* at one dilution and FIG. 15b plots full spectra of absorbance of *C. aurantiacus* at multiple concentrations.
Figure 15B:
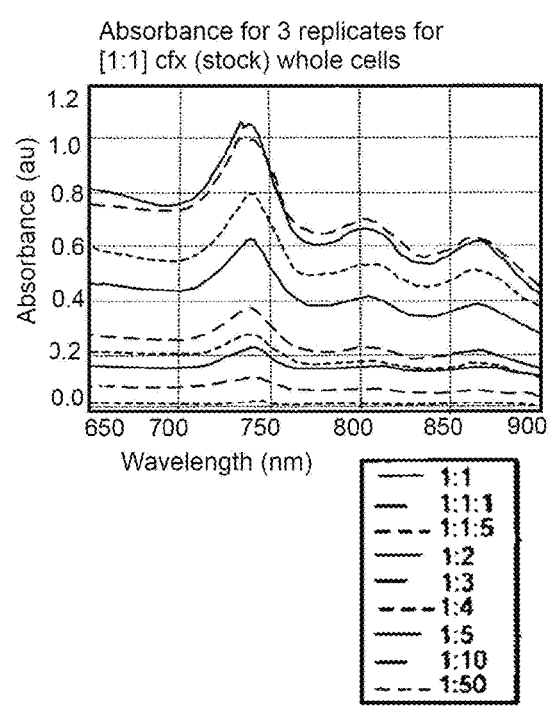
Figure 16A:
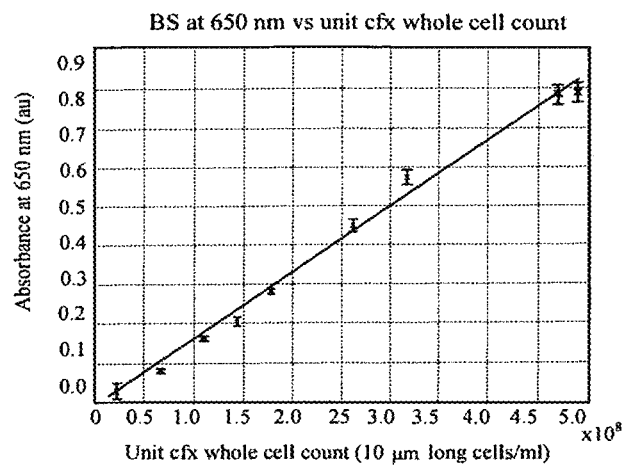
FIG. 16a is a plot of correlation between absorbance at 650 nm wavelength and cell count for *C. aurantiacus
Figure 16B:
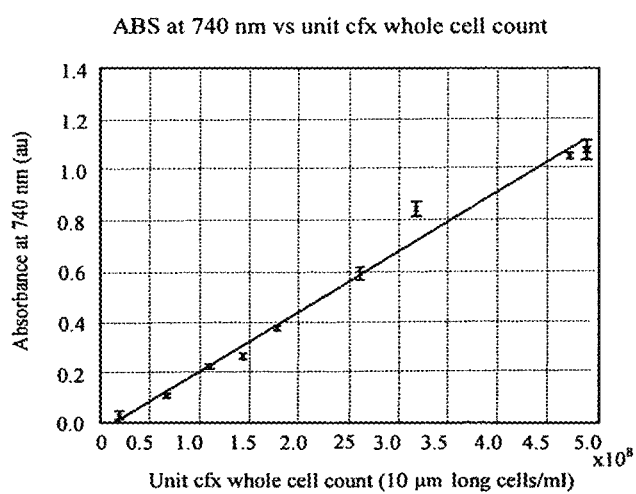
* and FIG. 16b is a plot of correlation between absorbance at 740 nm wavelength and cell count.

A method was developed to establish a faster process to count whole cells. A modified hemocytometry counting technique was used to count whole cell *C. aurantiacus* concentrations (per unit length of 10 μm), and absorbance data was gathered as three replicates of: 1:1, 1:1.1, 1:1.5, 1:2, 1:3, 1:4, 1:5, 1:10, and 1:50 dilutions were made. Full spectra (absorbance) data was gathered for each dilution, as in FIG. 15a. Each replicate was run to minimize instrument and operator error (FIG. 15b) and peak data was gathered and averaged at 650, 740, 808, and 866 nm. The samples were then counted on an optical microscope using a standard red blood cell counting technique and a hemocytometer. In this fashion, curves were developed for absorbance at 650 and 740 nm and cellular counts with error bars as shown in FIGS. 16a and 16b.

Example 12

Figure 19:
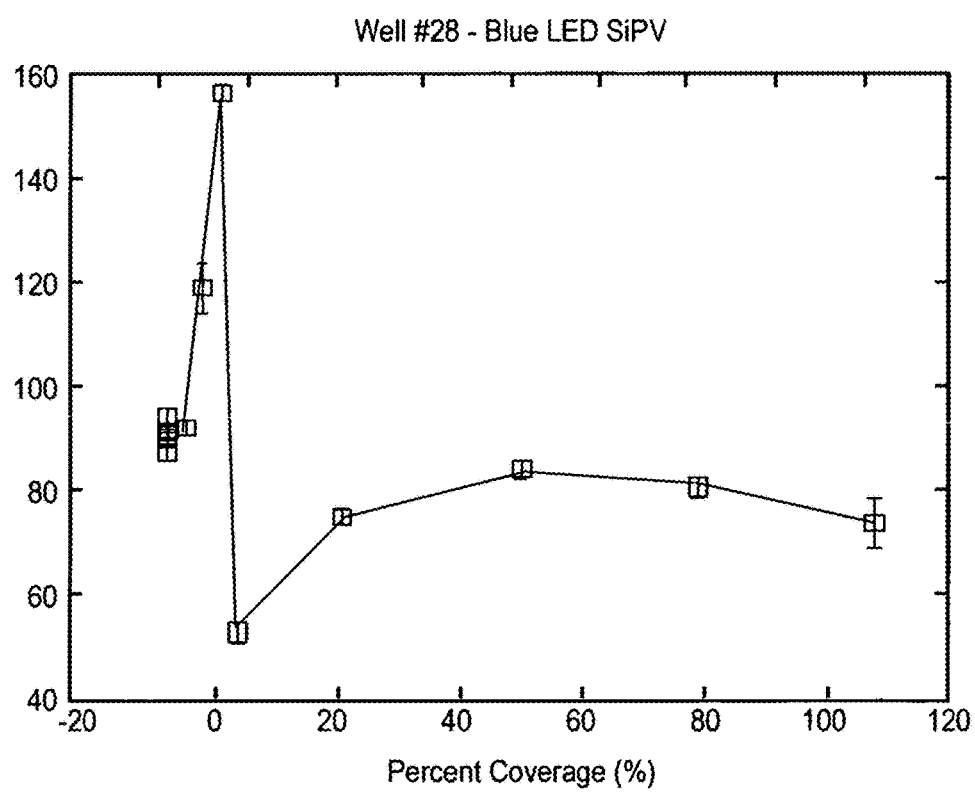
FIG. 19 is a plot of percent enhancement of a silicon photovoltaic (SiPV) device for percent coverage by chlorosomes of *C. aurantiacus*.

For the purposes of characterization and conformity in preparing the hybrid devices contemplated, determining the quantity of chlorosomes coating the cover glass hydrophobic surface was important. In particular, in various embodiments employing the chlorosomes of *C. aurantiacus* to enhance SiPV performance as disclosed herein, chlorosome percent coverage of the SiPV's light receiving surface (or the overlying borosilicate glass) is a significant factor as demonstrated by the FIG. 19 plot of percent enhancement against percent coverage; for the particular embodiment to which FIG. 19 relates, coverage should be in the 4 to 7% range and preferably about 4%. To arrive at percent coverage, accurate counting of the chlorosomes is required and can be estimated by measuring 650 nm absorbance.

Figure 17:
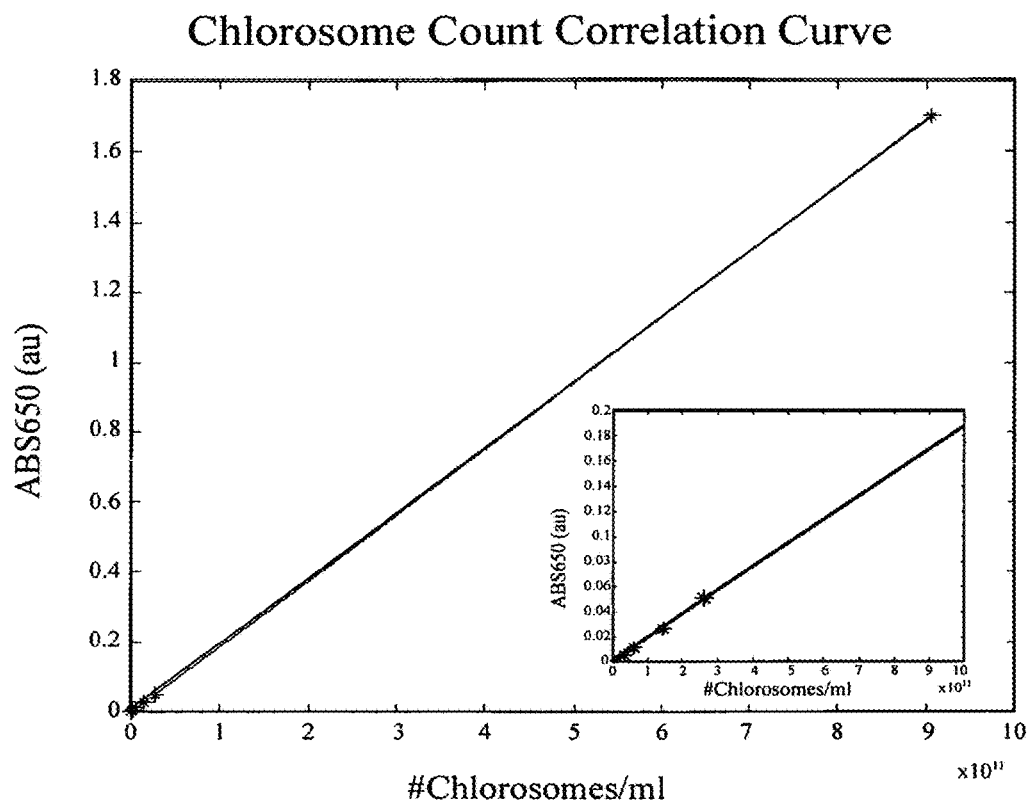
FIG. 17 is a plot of correlation between absorbance at 650 nm wavelength and number of RC– chlorosomes of *C. aurantiacus* and a zoomed-in-plot of the first four data points in that correlation showing close linearity between the two variables.

Absorbance of light was correlated to the density of chlorosomes as illustrated in FIG. 17. The calibration plot of FIG. 17 plots chlorosome count against chlorosome absorbance at the 650 nm wavelength. The 650 nm wavelength is chosen rather than a wavelength where absorbance of the chlorosome exhibits a peak because the absorbance at those wavelengths exhibiting a peak in the absorbance spectrum vary from one chlorosome to another depending, inter alia, on environmental factors effecting the growth of the bacterium from which the chlorosome was taken. The 650 nm wavelength absorbance, then, is linearly related to chlorosome count.

Example 13

Figure 31:
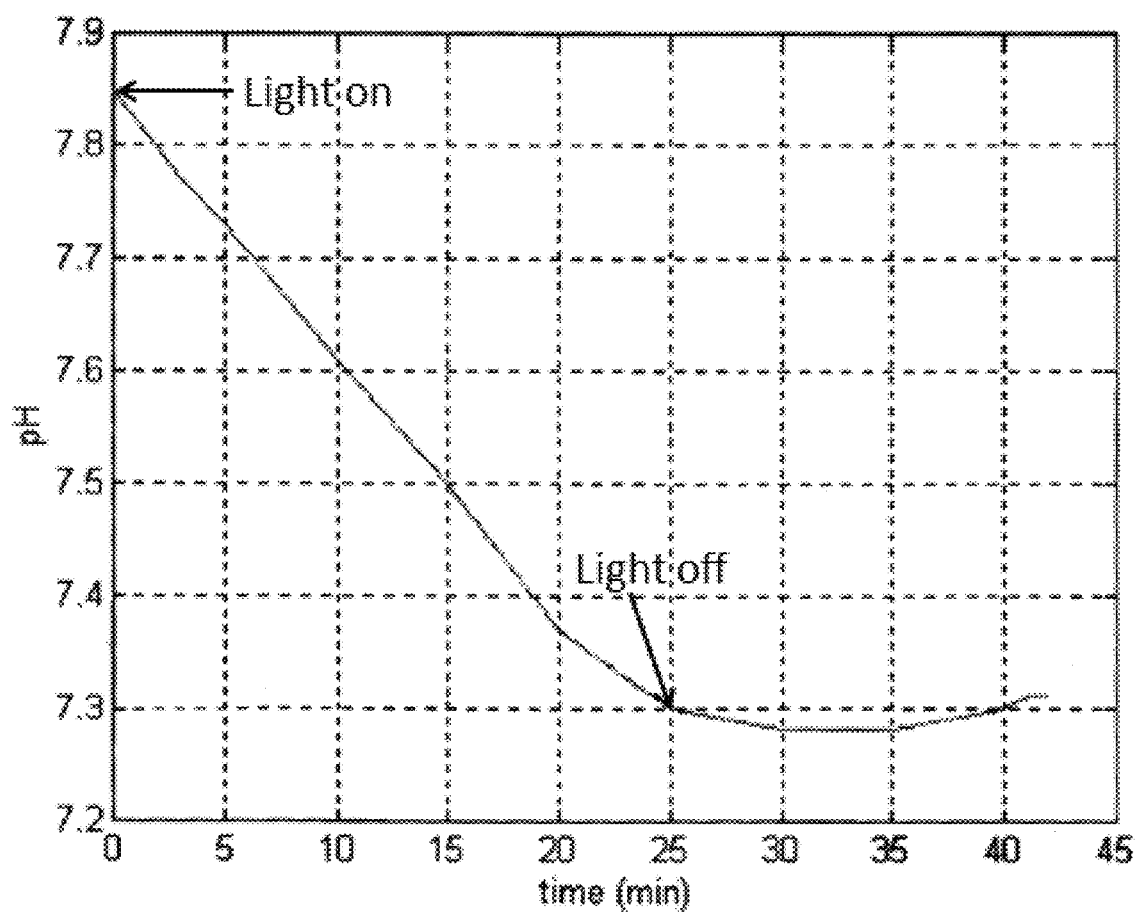
FIG. 31 is a graph showing reduction of pH upon exposure of biological components to light.

RC+ structures comprising light antenna structures coupled with reaction centers were extracted from cultured *Chloroflexus aurantiacus* and suspended at a concentration of ~1×10$^{11}$ units per ml in normal saline with NaOH added to adjust initial pH to 7.65 to match pH of solution to that of the RC+ preparation. The suspension was exposed to white light at 8,340 lux at room temperature (~23-25 C) and remained at room temperature throughout the experiment. As shown in FIG. 31, the pH was observed by pH meter to decline to 7.30 over a period of 25 minutes, whereupon the light exposure was terminated, after which the pH leveled off. The experiment was ended at 42 minutes, at a pH of 7.31.

RC+ structures comprising light antenna structures coupled with reaction centers extracted from cultured *Chloroflexus aurantiacus* were suspended in an aqueous Tris buffer solution at an initial pH of 7.66 at a concentration of ~1.5×10$^{11}$ units per ml. The preparation was exposed to infrared light with blue filter at intensities ranging from 1290 to 1320 lux at room temperature (~23-25 C). As shown in Table Q, the pH was observed by pH meter to decline to 7.26 in 10 minutes and to 6.99 over 60 minutes, whereupon the light exposure was terminated, after which the pH rebounded to 7.15 at 64 minutes and the experiment was ended. (In other experiments, the pH was observed to return to its starting value of about 7.65 after 50 minutes with no light exposure.) The temperature rise of the suspension upon exposure to light, such as seen with the infrared exposure as shown in Table Q, on analysis was not found to be a cause of the pH decrease. In other experiments pH decreases well below 7 were observed.

TABLE Q pH response of RC+ baseplate- light antenna structures to infrared exposure.

| Time (min) | Light intensity (lux) | pH | Temp (° F.) |
|---|---|---|---|
| 0 (light on) | 1320 | 7.60 | 26.0 |
| 5 | 1290 | 7.40 | 33.3 |
| 10 | 1300 | 7.26 | 36.2 |

TABLE Q-continued pH response of RC+ baseplate- light antenna structures to infrared exposure.

| Time (min) | Light intensity (lux) | pH | Temp (° F.) |
|---|---|---|---|
| 15 | 1300 | 7.17 | 37.9 |
| 20 | 1290 | 7.11 | 39.7 |
| 25 | 1290 | 7.07 | 40.7 |
| 30 | 1300 | 7.04 | 41.6 |
| 40 | 1290 | 7.01 | 42.7 |
| 50 | 1290 | 7.00 | 43.3 |
| 60 | 1290 | 6.99 | 43.8 |
| 61 (light off) | 0000 | 7.02 | 42.9 |
| 64 | 0000 | 7.15 | 38.6 |

Interpretation and Scope

Designation of the present application as a continuation-in-part of its parent application(s) as set forth above, and as required by U.S. Patent and Trademark Office rules and procedures, is not to be construed as an admission or acknowledgement that the present application contains any new matter in addition to the matter of its parent application(s).

It is intended that this specification be interpreted in accordance with the normal principles of English grammar and that words and phrases be given their ordinary English meaning as understood by persons of skill in the pertinent arts except as otherwise explicitly stated. If a word, term, or phrase is intended to be further characterized, specified, or narrowed in some way, then additional adjectives, modifiers, or descriptive text have been included in accordance with the normal principles of English grammar. It is intended that the meanings of words, terms, or phrases should not be modified or characterized in a manner differing from their ordinary English meaning as understood by persons of skill in the relevant arts except on the basis of adjectives, modifiers, or descriptive text that is explicitly present.

Except as otherwise explicitly stated, terms used in this specification, including terms used in the claims and drawings, are intended as "open" terms. That is, for example, the word "including" should be interpreted to mean "including but not limited to," the word "having" should be interpreted to mean "having at least," the word "includes" should be interpreted to mean "includes but is not limited to," the phrases "for example" or "including by way of example" should be interpreted as signifying that the example(s) given are non-exhaustive and other examples could be given, and other similar words and phrases should be given similar non-exclusive meanings.

In the written description and appended claims, the indefinite articles "a" and/or "an" are intended to mean "at least one" or "one or more" except where expressly stated otherwise or where the enabling disclosure requires otherwise. The word "or" as used herein is intended to mean "and/or", except where it is expressly accompanied by the word "either", as in "either A or B". Applicants are aware of the provisions of 35 U.S.C. §112, ¶6. The use of the words "function," "means" or "step" in the written description, drawings, or claims herein is not intended to invoke the provisions of 35 U.S.C. §112, ¶6, to define the invention. To the contrary, if the provisions of 35 U.S.C. §112, ¶6 are sought to be invoked, the claims will expressly include one of the exact phrases "means for performing the function of" or "step for performing the function of". Moreover, even if the provisions of 35 U.S.C. §112, ¶6 are explicitly invoked to define a claimed invention, it is intended that the claims not be limited only to the specific structure, material or acts that are described in the preferred embodiments, but in addition, extend to any and all structures, materials or acts that perform the claimed function as described in alternative embodiments or forms of the invention, or that are well known present or later-developed equivalent structures, material or acts for performing the claimed function.

In the foregoing description, various details, specific aspects, embodiments, and examples have been described in order to illustrate and explain the subject matter, to provide a thorough understanding of the various aspects, to enable persons skilled in the pertinent arts to practice the described subject matter, and to disclose the best mode of doing so known to applicants. These details, specific aspects, embodiments, and examples are not intended to be limiting; rather, it will be apparent to persons of skill in the relevant arts that, based upon the teachings herein, various changes, substitutions, modifications, rearrangements, may be made and various aspects, components, or steps may be omitted or added, without departing from the subject matter described herein and its broader aspects. Except as otherwise expressly stated or where aspects or features are inherently mutually exclusive, aspects and features of any embodiment described herein may be combined with aspects and features of any one or more other embodiments. The appended claims are intended to encompass within their scope any and all changes, substitutions, modifications, rearrangements, combinations of aspects or features, additions, and omissions that are within the spirit and scope of the subject matter as described herein and/or within the knowledge of a person of skill in the art. The scope of the invention is defined by the claims, and is not limited by or to the particular embodiments or aspects chosen for detailed exposition in the foregoing description, but rather extends to all embodiments or aspects as defined by the claims, as well as any equivalents of such embodiments or aspects, whether currently known or developed in the future.

So as to reduce the complexity and length of the detailed description, and to provide background in certain areas of technology, each of the materials identified in the "REFERENCES" section below is expressly incorporated by reference. Applicants believe that the subject matter incorporated is "non-essential" in accordance with 37 CFR 1.57, because it is referred to for purposes of indicating the background of the invention or illustrating the state of the art. However, if the Examiner concludes that any of the incorporated material constitutes "essential material" within the meaning of 37 CFR 1.57(c)(1)-(3), applicants will amend the specification to expressly recite the essential material that is incorporated by reference as allowed by the applicable rules.

REFERENCES

Books:
Chlorophylls, Hogo Scheer, CRC, 1991.
Light-Harvesting Antennas in Photosynthesis, B R Green and W W Parson, eds. Kluwer Academic Publishing (Dordrecht: Kluwer), 1991.
Photosynthesis: Photobiochemistry and Photobiophysics, Bacon Ke, Springer, 2001
Oxygenic Photosynthesis: The Light Reactions, Donald R. Ort, Charles F. Yocum, Iris F. Heichel, Springer, 1996.
Chemicals from Microalgae, Zvi Cohen, CRC, 1999
Physicochemical & Environmental Plant Physiology, Park S. Nobel, Academic Press, 2005
Molecular Biology of Membranes: Structure and Function, Howard R. Petty, 1993

Structure of Phototrophic Prokaryotes, John F. Stolz, CRC 1990

Blankenship, R. E. (2002). Molecular Mechanisms of Photosynthesis, Blackwell Science Journals:

Yamnaka, G., et al., Molecular Architecture of a Light-harvesting Antenna Isolation and Characterization of Phycobilisome Subassembly Particles, J Biol. Chem., 257(8): 4077-4086, 1982.

Lundell, D and A N Glazer, Molecular Architecture of a Light-harvesting Antenna Structure of the 18 s Core-rod Subassembly of the Synechococcus 6301 Phycobilisome, J Biol Chem., 258: 994-901, 1983.

Montano G A, Wu H-M, Lin S, Brune D C and Blankenship R E (2003) Isolation and characterization of the B798 baseplate light-harvesting complex from the chlorosomes of Chloroflexus aurantiacus. Biochemistry 42: 10246-10251.

Simidjiev, I., et al., Isolation of Lamellar Aggregates of the Light-Harvesting Chlorophyll a/b Protein Complex of Photosystem II with Long-Range Chiral Order and Structural Flexibility Montano, G A, Bowen B P, LaBelle J T, Woodbury N W, Pizziconi V B and Blankenship R E (2003) Characterization of Chlorobium tepidum chlorosomes. A calculation of bacteriochlorophyll c per chlorosome and oligomer modeling. Biophys. J. 85: 2560-2565.

Blankenship R E and Matsuura K (2003). Antenna complexes from green photosynthetic bacteria. In: Light-Harvesting Antennas, B R Green and W W Parson, eds. Kluwer Academic Publishing (Dordrecht: Kluwer), 195-217. 1991.

Hu, D. and Blankenship, R. E. (2002) Rapid one step purification of the BChl-a containing FMO-protein from the green sulfur bacterium Chlorobium tepidum using a high efficiency immunomatrix, Photosynth. Res., 71, 149-154

Frigaard, N-U, et al., Isolation and characterization of carotenosomes from a bacteriochlorophyll c-less mutant of Chlorobium tepidum, Photosynthesis Research, 86:101-111, 2005.

Qian, P., et al., Isolation and Purification of the Reaction Center (RC) and the Core (RC–LH1) Complex from Rhodobium marinum: the LH1 Ring of the Detergent-Solubilized Core Complex Contains 32 Bacteriochlorophylls, Plant Cell Physiology, 41 (12): 1347-1353, 2000.

Cogdell, R. G., J. Durant, J. Valentine, J. G. Lindsay, and K. Schmidt. 1983. The isolation and partial characterisation of the light-harvesting pigment-protein complement of Rps. acidophile. Biochim. Biophys. Acta. 722:427-455.

Cogdell, R. J., and A. M. Hawthornthwaite. 1993. Preparation, purification and crystallization of purple bacterial antenna complexes. In The Photosynthetic Reaction Center, Vol. 1. J. R. Norris and J. Deisenhofer, editors. Academic Press, New York. 23-42.

Clayton, R. K., and B. J. Clayton. 1981. B850 pigment-protein complex of Rhodopseudomonas sphaeroides: extinction coefficients, circular dichroism, and the reversible binding of bacteriochlorophyll. Proc. Natl. Acad. Sci. U.S.A. 78:5583-5587.

Cogdell, R. J., and A. R. Crofts. 1990b. Analysis of the pigment content of an antenna pigment/protein complex from three strains of Rhodopseudomonas sphaeroides. Biochim. Biophys. Acta. 502:409-416.

Cogdell, R. J., A. M. Hawthornthwaite, M. B. Evans, L. A. Ferguson, C. Kerfeld, J. P. Thornber, F. van Mourik, and R. van Grondelle. 1990a. Isolation and characterisation of an unusual antenna complex from the marine purple sulphur photosynthetic bacterium Chromatium purpuratum BW5500. Biochim. Biophys. Acta. 1019:239-244.

Cogdell, R. J., and J. P. Thurber. 1979. The preparation and characterization of different types of light-harvesting pigment-protein complexes from some purple bacteria. In The CIBA Foundation Symposium 61 (new series) on Chlorophyll Organisation and Energy Transfer in Photosynthesis.

G. Wolstenholme and D. Fitzsimons, editors. Elsevier, Amsterdam. 61-79.

Evans, M. B., A. M. Hawthornthwaite, and R. J. Cogdell. 1990. Isolation and characterization of the different B800-850 light harvesting complexes from low- and high-light grown cells of Rhodopseudomonas cryptolactis. Biochim. Biophys. Acta. 1016:71-76.

Yokthongwattana, K., et al., Isolation and characterization of a xanthophyll-rich fraction from the thylakoid membrane of Dunaliella salina (green algae), Photochem. Photobiol. Sci., 4:10288-1034, 2005.

Marquardt, J., et al., Isolation and Characterization of Biliprotein Aggregates of Acaryochlris marina, a Prochloron-like prokaryote containing mainly chlorophyll d, FEBS Letters, 410:428-432, 1997.

Adam G. Koziol, Tudor Borza, Ken-Ichiro Ishida, Patrick Keeling, Robert W. Lee, and Dion O. Dumford, Tracing the Evolution of the Light-Harvesting Antennae in Chlorophyll a/b-Containing Organisms, Plant Physiology, April 2007, Vol. 143, pp. 1802-1816, www.plantphysiol.org, 2007 American Society of Plant Biologists X. Hu, et al., Predicting the structure of the light-harvesting complex II of Rhodospirillum molischianum, Protein Sci., 1995 4: 1670-1682.

N Nagata, R Tanaka, S Satoh, J Minagawa, A Tanaka, Isolation and characterization of a gene for chlorophyllide a oxygenase from Prochlorothrix hollandica, Endocytobiosis Cell Res., 15: 321-327, 2004.

Andreucii, F., et al., Isolation of phosphorylated and dephosphorylated forms of the CP43 internal antenna of photo system II in Hordeum vulgare L. Journal of Experimental Botany 2005 56(414): 1239-1244.

Andrew N. Webber, Rapid Isolation and Purification of Photo system I Chlorophyll-Binding Protein From Chlamydomonas reinhardtii, Photosynthesis Research Protocols, Methods in Molecular Biology, Volume: 274: 19-28, 2004.

B R Green and D G Dumford, The Chlorophyll-Carotenoid Proteins of Oxygenic Photosynthesis, Annual Review of Plant Physiology and Plant Molecular Biology, Vol. 47: 685-714, 1996. Observation of the Energy-Level Structure of the Low-Light Adapted B800 LH4 Complex by Single-Molecule Spectroscopy, Biophysical Journal, 87: 3413-3420, 2004

Zhang, S-J, et al., Energy Transfer among Chlorophylls in Trimeric Light-harvesting Complex II of Bryopsis corticulans, Acta Biochimica et Biophysica Sinica 38(5): 310-317, 2006.

Planck, Tracy, et al., Subunit Interactions and Protein Stability in the Cyanobacterial Light-Harvesting Proteins, Journal of Bacteriology, 177(12): 6798-6803, 1995.

Bibby, T. S., et al., Low-light adapted Prochlorococcus species possess specific antennae for each photo system, Nature, 424: 1051-1054, 2003

Reports:

Structure, Function and Reconstitution of Chlorosome Antennas from Green Photosynthetic Bacteria, Robert E.

Blankenship, Final Report DE-FG03-01ER15214, DOE, September 2001-August 2004

Theses:

Hu, D. (2001) Investigation of the Fenna-Matthews-Olson protein from photosynthetic green sulfur bacteria. Ph.D. Dissertation, Arizona State University, Tempe, Ariz.

LaBelle, JT, Design Feasibility of a Nanoscale Biophotonic Hybrid Device, PhD Dissertation, Arizona State University, 2001.

We claim:

1. A method of producing a force-adapted population comprising organisms expressing force-adaptively optimized extractable biological components for a biohybrid device, the method comprising:
    (a) providing a physically segregated population of organisms expressing an extractable biological component having a characteristic desired to be optimized for enhanced biohybrid device performance;
    (b) physically segregating the population into a plurality of sub-populations;
    (c) selecting one or more environmental variables each representing the value of a controllable environmental condition;
    (d) evaluating a measure of the characteristic desired to be optimized in each sub-population after subjecting each sub-population during growth to controllable environmental conditions at pre-specified values of each of the selected environmental variables, each sub-population being subjected to a different selection of such values, wherein evaluating a measure of the characteristic desired to be optimized comprises measuring or observing at least one physical or chemical property relating to the characteristic;
    (e) determining from the evaluation a relation between the measure of the characteristic desired to be optimized and the values of each of the selected environmental variables corresponding thereto;
    (f) from the relation, determining values of the selected environmental variables corresponding to a desired value of a measure of a characteristic desired to be optimized;
    (g) growing a segregated population of the organisms while subjecting the population to controllable environmental conditions at the values of the environmental variables so determined, to produce at least one force-adapted organism wherein the characteristic desired to be optimized is altered in comparison to naturally occurring organisms of the same species;
    (h) extracting from the at least one force-adapted organism a plurality of extractable biological components each comprising a light antenna structure, and
    (i) disposing the extractable biological components in an apparatus wherein the extractable biological components are constrained to a substrate wherein the apparatus is configured to permit exposure of the light antenna structures to light.

2. The method of claim 1, in which the characteristic desired to be optimized comprises the emission by the biological component of Stokes-shifted light in response to exposure of the biological component to light.

3. The method of claim 1, in which the characteristic desired to be optimized comprises the production by the biological component of hydrogen ions in response to exposure of the biological component to light.

4. The method of claim 1, wherein the substrate comprises graphene.

5. The method of claim 1, wherein the light antenna structures are reaction center minus (RC−) light antenna structures.

6. The method of claim 1 wherein the plurality of light antenna structures comprises light antenna structures obtained from a genetic sequence cloned or derived from organisms of a force-adapted population.

7. The method of claim 1, wherein the substrate comprises a film or sheet.

8. The method of claim 1, wherein the substrate comprises a liquid, gel, matrix, or suspension in which the light antenna structures are suspended.

9. The method of claim 1, wherein the light antenna structures are disposed and configured to produce hydrogen (H+) ions upon exposure of the light antenna structures to light and release the hydrogen ions into an aqueous solution.

10. The method of claim 1, wherein the light antenna structures are RC+ light antenna structures.

* * * * *